United States Patent
Jarczowski et al.

(10) Patent No.: US 10,435,704 B2
(45) Date of Patent: Oct. 8, 2019

(54) METHOD OF CO-EXPRESSING A GLYCOPROTEIN AND A SINGLE-SUBUNIT OLICOSACCHARYLTRANSFERASE IN A PLANT

(71) Applicant: Icon Genetics GmbH, Munich (DE)

(72) Inventors: Franziska Jarczowski, Seegebiet (DE); Romy Kandzia, Halle (DE); Frank Thieme, Halle (DE); Victor Klimyuk, Leipzig (DE); Yuri Gleba, Berlin (DE)

(73) Assignee: Icon Genetics GmbH, München (DE)

( * ) Notice: Subject to any disclaimer, the term of this patent is extended or adjusted under 35 U.S.C. 154(b) by 0 days.

(21) Appl. No.: 14/895,350

(22) PCT Filed: Jun. 3, 2014

(86) PCT No.: PCT/EP2014/001500
§ 371 (c)(1),
(2) Date: Dec. 2, 2015

(87) PCT Pub. No.: WO2014/195011
PCT Pub. Date: Dec. 11, 2014

(65) Prior Publication Data
US 2016/0115498 A1   Apr. 28, 2016

(30) Foreign Application Priority Data
Jun. 4, 2013   (EP) .................................... 13002866

(51) Int. Cl.
| | |
|---|---|
| *C12N 15/82* | (2006.01) |
| *C07K 16/28* | (2006.01) |
| *C07K 16/32* | (2006.01) |
| *C12N 9/10* | (2006.01) |

(52) U.S. Cl.
CPC ...... *C12N 15/8257* (2013.01); *C07K 16/2887* (2013.01); *C07K 16/32* (2013.01); *C12N 9/1051* (2013.01); *C12N 15/8258* (2013.01); *C12Y 204/01* (2013.01); *C07K 2317/41* (2013.01)

(58) Field of Classification Search
None
See application file for complete search history.

(56) References Cited

U.S. PATENT DOCUMENTS

2012/0328626 A1   12/2012 Sethuraman

FOREIGN PATENT DOCUMENTS

| WO | 2009126816 | 10/2009 | |
|---|---|---|---|
| WO | WO 2010/049177 A1 * | 5/2010 | ........... C07K 14/395 |

OTHER PUBLICATIONS

Fischer et al. Molecular farming of pharmaceutical proteins. (2000) Transgenic Research; vol. 9; pp. 279-299.*
International Search Report for PCT/EP2014/001500, EPO, dated Nov. 12, 2014.
Giritch et al., "Rapid high-yield expression of full-size IgG antibodies in plants coinfected with noncompeting viral vectors", Proceedings of the National Academy of Sciences, Oct. 3, 2006,vol. 103, No. 40, pp. 14701-14706.
Masuda et al., "Mutational deglycosylation of the Fc portion of immunoglobulin G causes-sulfation of tyrosine adjacently preceding the orginially glycosylated site" Febs Letters, Jul. 2, 2010, vol. 584, No. 15, pp. 3474-3479.
Reddy et al., "Glycosylation of the overlapping sequons in yeast external invertase: effect of amino acid variation on site selectivity in vivo and in vitro" Glycobiology, Jun. 1, 1999, vol. 9, No. 6, pp. 547-555.
Chuang et al. "Computational prediction of N-linked glycosylation incorporating structural properties and patterns", Bioinformatics, Sep. 1, 2012, vol. 28, No. 17, pp. 2249-2255.
Phuc Vinh Nguyen Lam et al. "Structure-based Comparative Analysis and Prediction of N-linked Glycosylation Sites in Evolutionarily Distant Eukaryotes" Genomics, Proteomics & Bioinformatics, Apr. 1, 2013, vol. 11, No. 2, pp. 96-104.
Trkola et al., "Human momclonal antibody 2G12 defines a distinctive neutralization epitope on the gp 120 glycoprotein of human immunodeficincy virus type 1" Journal of Virology, The American Society for Mircrobiology, Feb. 1, 1996, vol. 70, No. 2, pp. 1100-1108.
Saint-Jore-Dupas et al., "From planta to pharma with glycosylation in the toolbox", Trends in Biotechnology, Jul. 1, 2007, vol. 25, No. 7, pp. 317-323.
Strasser et al. "Generation of glyco-engineered Nicotiana benthamiana for the production of monclonal antibodies with homogeneous human-like N-glycan structure" Plant Biotechnology Journal, May 1, 2008, vol. 6, No. 4, pp. 392-402.
Schähs et al. "Production of a monoclonal antibody in plants with a humanized N-glycosylation pattern" Plant Biotechnology Journal, Sep. 1, 2007, vol. 5, No. 5, pp. 657-663.

* cited by examiner

*Primary Examiner* — Cathy Kingdon Worley
(74) *Attorney, Agent, or Firm* — David M. Saravitz; Williams Mullen

(57) ABSTRACT

A process of producing a recombinant glycoprotein in a plant, in cells of a plant, or in plant cells is provided. The process comprises expressing in said plant, in cells of said plant or in said plant cells a nucleic acid sequence encoding a polypeptide having an N-glycosylation site and co-expressing a nucleic acid sequence encoding a heterologous single-subunit oligosaccharyltransferase.

1 Claim, 24 Drawing Sheets

Specification includes a Sequence Listing.

```
ASTKGPSVFPLAPSSKSTSGGTAALGCLVKDYFPEPVTVSWNSGALTSGVHTFPAVLQSS  177
GLYSLSSVVTVPSSSLGTQTYICNVNHKPSNTKVDKKVEPKSCDKTHTCPPCPAPELLGG  237
PSVFLFPPKPKDTLMISRTPEVTCVVVDVSHEDPEVKFNWYVDGVEVHNAKTKPREEQYN  297
STYRVVSVLTVLHQDWLNGKEYKCKVSNKALPAPIEKTISKAKGQPREPQVYTLPPSRDE  357
LTKNQVSLTCLVKGFYPSDIAVEWESNGQPENNYKTTPPVLDSDGSFFLYSKLTVDKSRW  417
QQGNVFSCSVMHEALHNHYTQKSLSLSPGK                                447

Single Mutations: E293R, E294Y, Y296F, Y296E, Y300T, Y300G

Triple mutation: E294 + Y296T + Y300T

N - glycosylation site
```

Fig. 1A

MGKRKGNSLGDSGSAATASREASAQAEDAASQTKTASPPAKVILLPKTLIDEKDFIGIFPFPFWPVHFVLTVVA
LPVLAASCFQAFTVRMISVQIYGYLIHEFDPWPNYRAAEYMSTHGWSAFFSWFDYMSWYPLGRPVGSTTYPGLQ
LTAVAIHRALAAAGMPMSLNNVCVLMPAWFGAIATATLAFCTYEASGSTVAAAAALSFSIIPAHLMRSMAGEF
DNECIAVAAMLLTFYCWVRSLRTRSSWPIGVLTGVAYGYMAAAWGGYIFVLMVAMHAGISSMVDWARNTYNPS
LLRAYTLFYVVGTAIAVCVPPVGMSPFFKSLEQLGALLVLVFLCGLQVCEVLRAPAGVEVRSPANFKIRVRVFSV
MAGVAALAISVLAPTGYFGPLSVRVRALFVEHTRTGNPLVDSVAEHQPASPEAMWAFLHVCGVTWGLGSIVLAV
STPVHYSPSKVFWLLNSGAVYYFSTRMARLLLLSGPAACLSTGIFVGTILEAAVQLSFWDSDATKAKKQQKQAQ
RHQRGAGKGSGRDDAKNATTARAFCDVFAGSSLAWGHRMVLSIAMWALVTTAVSFFSSEFASHSTKFAEQSSN
PMIVFAAVVQNRATGKPMNLLVDDYLKAYEWLRDSTPEDARVLAWDYGYQITGNRTSLADGNTWNHEHIAT
IGKMLTSPVVEAHSLVRHMADYVLIWAGOSGDLMKSPHMARIGNSVYHDICPDDPLCQQFGFHRNDYSRPTPMM
RASLLYNLHEAGKRKGVKVNPSLFQEVYSSKYGLVRIFKVMNVSAESKKWVADPANRVCHPPGSWICPGQYPPA
KEIQEMLAHRVPFDQVTNADRKNMVGSYQEEYMRRMRESENRRGSHHHHHH

Fig. 1B

MGKRKGNSLGDSGSAATASREASAQAEDAASQTKTASPPAKVILLPKTLTDEKDFIGIFPFFWPVHFVLTVVALFV
LAASCFQAFTVRMISVQIYGYLIHEFDPWFNYRAAFYMSTHGWSAFFSWFDYMSWYPLGRPVGSTTYPGLQLTAVAI
HRALAAAGMPMSLNMVCVLMPAWFGAIATATLAFCTYEASGSTVAAAAAALSFSIIPAHLMRSMAGEFDNECIAVAA
MLLTFYCWVRSLRTRSSWPIGVLTGVAYGVMAAAWGGYIFVLNMVAMHAGISSMVDWARNTYNPSLLRAYTLFYVVG
TAIAVCVPPVGMSPFKSLEQLGALLVLVFLCGLQVCEVLRAPAGVEVRSRANFKIRVRVFSVMAGVAALAISVLAPT
GYFGPLSVRVRALFVEHTRTGNPLVDSVAEHQPASPEAMWAFLHVCGVTWGLGSSIVLAVSTFVHYSPSKVFWLLNSG
AVYYFSTRMARLILLSGPAACLSTGIFVGTILEAAVQLSFWDSDATKAKKQOKQAQRHQRGAGKGSGRDDAKNATTA
RAFCDVFAGSSLAWGHRMVLSIAMWALVTTAVSFPSSEFASHSTKFAEQSSNPMIVFAAVVQNRATGKPMNLLVDD
YLKAYEWLRDSTPEDARVLAWDYGYQTTGIGNRTSLADGNTWNHEHIATIGKMLTSPVVEAHSLVRHMADYVLIWA
GQSGDLMKSPHMARIGNSVYHDICPDDPLCQQFGFHRNDYSRPTPMRASLLYNLHEAGKRKGVKVNPSLFQEVYSS
KYGLVRIFKVMNVSAESKKWVADPANRVCHPPGSWICPGQYPPAKEIQEMLAHRVPFDQVTNADRKNNVGSYQEEYM
RRMRESENRR

Fig. 2C

MGKRKGNSLGDSGSAATASREASAQAEDAASQTKTASPPAKVLLPKILTDEKDFIGIFPFPFWPVHFVLTVVALFV
LAASCFQAFTVRMISVQIYGYLIHEFDPWFNVRAAFYMSTHGWSAFFSWFDYMSWYPLGRPVGSTTYPGLQTAVAI
HRALAAAGMPMSLNNVCVLMPAWFGAIATATLAFCTYEASGSTVAAAAALSFSIIPAHLMRSMAGEFDNECIAVAA
MLLTFYCWVRSLRTRSSWPIGVLTGVAYGYMAAAWGGYIFVLNMVAMHAGISSMVDWARNTYNPSLIRAYTLFYVG
TAIAVCVPPVGMSPFKSLEQLGALLVLVFLCGLQVCEVLRARAGVEVRSRANFKIRVRVFSVMAGVAALAISVLAPT
GYFGPLSVRVRALFVEHTRTGNPLVDSVAEHQPASPEAMWAFLHVCGVTWCLGSIVLAVSTFVHYSPSKVFWLLNSG
AVYYFSTRMARLLLLSGPAACLSTGIFVGTILEAAVQLSFWDSDATKAKKQQKQAQRHQRGAGKGSGRDDAKNATTA
RAFCDVFAGSSLAWGHRMVLSTAMWALVTTAVSFFSSEPASHSTKFAEQSSNPMIVFAAVQNRATGKPMNLLVDD
YLKAYEWLRDSTPEDARVLAWWDYGYQITGIGNRTSLADGNTWNHEHIATIGKMLTSPVVEAHSLVRHMADYVLIWA
GQSGDLMKSPHMARIGNSVYHDICPDDPLCQQFGFHRNDYSRPTPMRASLLYNLHEAGKRKGVKVNPSLFQEVYSS
KYGLVRIFKVMNVSAESKKWVADPANRVCHPPGSWICPGQYPPAKEIQEMLAHRVPFDQVTNADRKNNVGSYQEEYM
RRMRESENRRGSGHHHHHH

Fig. 2 D

Variable region of Trastuzumab Kappa light chain:

```
D   I   Q   M   T   Q   S   P   S   S   L   S   A   S   V   G   D   R   V   T   I   T   C   R   A   S   Q   D   V   N
GATATACAGATGACACAGACTCAATCAATCCACCATCTTCACTTAGTGCTAGTGTTGGAGATAGAGTGACCATCACATGCAGAGCCAGTCAAGATGTGAAT
T   A   V   A   W   Y   Q   Q   K   P   G   K   A   P   K   L   L   I   Y   S   A   S   F   L   Y   S   G   V   P   S
ACAGCTGTAGCATGGTATCAGCAGAAACCTGGTAAAGCTCCGAAGTTGCTCATCTATTCTGCGAGTTTCCTATACTCTGGTGTTCCATCC
R   F   S   G   S   R   S   G   T   D   F   T   L   T   I   S   S   L   Q   P   E   D   F   A   T   Y   Y   C   Q   Q
AGGTTTTCTGGGTCTAGAAGCTGGAACTGACTTCACTCTGACCATTAGCTCTTTACAACCTGAAGATTTTGCCACTTACTATTGCCAGCAA
H   Y   T   T   P   P   T   F   G   Q   G   T   K   V   E   I   K
CATTACACTACACCACCTACCTTTGGACAGGGCACAAAGGTCGAGATTAAG
```

Generic Kappa constant region:

```
R   T   V   A   A   P   S   V   F   I   F   P   P   S   D   E   Q   L   K   S   G   T   A   S   V   V   C   L   L   N
cgaacagttgctgctgccccctagtgttttcatcttcccccatccgatgaacaattgaaatctggaactgcatccgtagtgtgcttgttgaac
N   F   Y   P   R   E   A   K   V   Q   W   K   V   D   N   A   L   Q   S   G   N   S   Q   E   S   V   T   E   Q   D
aatttctaccctagagaagctaaggttcaatggaaagtcgataatgcactacagtctggtaattcacaagagtcgttactgaacaagac
S   K   D   S   T   Y   S   L   S   S   T   L   T   L   S   K   A   D   Y   E   K   H   K   V   Y   A   C   E   V   T
tctaaggactctacttacagtctcttctccaactctaacctaagcagattacgaaaagcataagtctatgtctgttgtgaagttaca
H   Q   G   L   S   S   P   V   T   K   S   F   N   R   G   E   C
catcaaggattgagttcaccagttcacaagttctttaacgtggtgagtgt
```

Variable region of Rituximab Kappa light chain:

```
 Q  I  V  L  S  Q  S  P  A  I  L  S  A  S  P  G  E  K  V  T  M  T  C  R  A  S  S  S  V  S
CAGATAGTGCTTAGCAGTCAGTCACCAGCAATTTTGTCTGCATCACCTGGTGAGAAAGTTACGATGACTTGTAGAAGCTCCAGTGTCC
 Y  I  H  W  F  Q  Q  K  P  G  S  S  P  K  P  W  I  Y  A  T  S  N  L  A  S  G  V  P  V  R
TACATCCATTGGTTCCAACAGAAACCAGGCAGTTCCTCCTAAACCCTGGATTTATGCCACATCTAACTTAGCTTCTGGTGTACCTGTCAGG
 F  S  G  S  G  S  G  T  S  Y  S  L  T  I  S  R  V  E  A  E  D  A  A  T  Y  Y  C  Q  Q  W
TTTAGTGGCTCTGGAAGTGGAACAAGCTATTCACTGACCATATCTCGTGTTGAAGCGGAAGATGCAGCTACCTACTATTGCCAACAGTGG
 T  S  N  P  P  T  F  G  G  G  T  K  L  E  I  K
ACTTCCAATCCACCGACTTCGGAGGAGGTACTAAGCTCGAGATTAAG
```

Generic Kappa constant region:

```
 R  T  V  A  A  P  S  V  F  I  F  P  P  S  D  E  Q  L  K  S  G  T  A  S  V  V  C  L  L  N
cgaacagttgctgcctccctagtgtcttcatttttccccccatccgatgaacaattgaaatctggaactgcatccgtagtatgcttgttgaac
 N  F  Y  P  R  E  A  K  V  Q  W  K  V  D  N  A  L  Q  S  G  N  S  Q  E  S  V  T  E  Q  D
aattctacccctagagaagaagtaaagttcaatgggaaagttcgataatgcactacagtctggtaattcacaagagtctgtaactgaacaagac
 S  K  D  S  T  Y  S  L  S  S  T  L  T  L  S  K  A  D  Y  E  K  H  K  V  Y  A  C  E  V  T
tctaaggactccacttactcactttcctcctccaactcttaccctatccaaggcagattacgaaaagcataagtctatgcttgtgaagttaca
 H  Q  G  L  S  S  P  V  T  K  S  F  N  R  G  E  C
catcaaggattgagtcaccagttcaccaagagtttaaccgtggtgagtgt
```

METHOD OF CO-EXPRESSING A GLYCOPROTEIN AND A SINGLE-SUBUNIT OLICOSACCHARYLTRANSFERASE IN A PLANT

CROSS REFERENCE TO RELATED APPLICATIONS

This application is the U.S. National Stage of International Application PCT/EP2014/001500, filed Jun. 3, 2014, which designates the U.S. and was published by the International Bureau in English on Dec. 11, 2014, and which claims the benefit of European Patent Application No. 13 002 866.5, filed Jun. 4, 2013; all of which are hereby incorporated herein in their entirety by reference.

FIELD OF THE INVENTION

The present invention relates to a process of producing a recombinant glycoprotein in a plant, cells of a plant, or in plant cells, wherein the glycoprotein has a high N-glycan occupancy at an N-glycosylation site. The invention also relate so methods for modulating occupancy of N-glycans at N-glycosylation sites of recombinant glycoproteins in plants, specifically IgG monoclonal antibodies. The invention also provides recombinant glycoprotein having particular amino acid residues nearby N-glycosylation sites of consensus sequence Asn-X-Ser/Thr.

BACKGROUND OF THE INVENTION

It is known that N-glycosylation plays an important role in determining the biological activity and pharmacokinetic properties of many biopharmaceuticals. N-glycosylation of immunoglobulin G (IgG) at asparagine residue 297 plays a critical role in antibody stability and immune cell-mediated Fc effector function. For example, the presence of glycan as well as glycan structure itself at this conserved glycosylation site of the IgG Fc domain is crucial for promoting interaction between mAb and the Fc Receptor (FcR). It was shown that different forms of glycosylation (e.g. different glycan structures) define different effects, some are beneficial, while others are detrimental for biological and pharmacokinetic properties of mAbs. For example, defucosylated glycosylated therapeutic mAbs like Herceptin manufactured in CHO-cells (Shields, R. L., et al., 2002, *J. Biol. Chem.*, 277: 26733-26740) or defucosylated anti-CD30 mAbs expressed in the small aquatic plant *Lemna minor* (Cox, K. M. et al., 2006, *Nat. Biotechnol.*, 24:1591-1597) were shown to be ca 30-50-fold more active in the efficacy of Fc-gamma receptor IIIa (FcγRIIIa) mediated ADCC than their counterparts with alpha-1,6 (CHO cells) or alpha-1,3-linked (*lemna*) fucose residues. Similar results were reported for rituximab and other mAbs produced in animal and plant cells (Shinkawa, T. et al., 2003, *J. Biol. Chem.*, 278: 3466-3473; Niwa, R., et al., 2004, *Cancer Res.*, 64:2127-2133; Zeitlin, L., et al., 2011, *Proc. Natl. Acad. Sci. USA*, 108:20690-20694; Gasdaska, J R. et al., 2012, *Mol. Immunol.*, 50:134-141).

Glycan absence at glycosylation sites of the Fc region has a detrimental effect on biological activities and pharmacokinetic properties of recombinant mAb. Removing the N-glycan severely impairs ADCC and CDC of CHO-cell produced mAbs (Jefferis R., 2007, *Expert Opin Biol Ther.*, 7:1401-13). Aglycosylated cetuximab (an Epidermal Growth Factor Receptor inhibitor used for the treatment of metastatic colorectal cancer and head and neck cancer) did not bind to FcγRI or FcγRIIIa nor has it ADCC activity even at high effector-target cell ratios (Patel, D., et al., 2010, *Hum Antibodies*, 19:89-99). Structural studies suggested that the N-glycan might exert its effects predominantly through stabilisation of the conformation of the Fc domain (Mimura, Y. et al., 2000, *Mol Immunol.*, 37:697-706; Sondermann, P., et al., 2000, *Nature*, 406:267-273; Mimura, Y. et al., 2001, *J Biol Chem.*, 276:45539-45547). A recent detailed study demonstrated that hemi-glycosylation does not impact Fab-mediated antigen binding, nor does it impact neonatal Fc receptor binding. But hemi-glycosylated mAb-X has slightly decreased thermal stability in the CH2 domain and, more importantly, the hemi-glycosylated form shows significantly decreased binding affinity towards all Fc gamma receptors (FcγRs) including the high-affinity FcγRI, and the low-affinity FcγRIIA, FcγRIIB, FcγRIIIA and FcγRIIIB (Ha, S., et al., 2011, *Glycobiology*, 21:1087-1091). In the case mentioned above, the decreased binding affinities of hemi-glycosylated mAb-X to FcγRs result in a 3.5-fold decrease in antibody-dependent cell cytotoxicity (ADCC) in comparison to its fully glycosylated counterpart. As ADCC often plays an important role in therapeutic antibody efficacy, it is expected that glycosylation status will not only affect the antibody quality but also may impact the biological function of the product.

Commercially available therapeutic antibodies exhibit 99-100% Fc glycosylation site occupancy, while monoclonal antibody samples derived from transgenic plants may often contain significant amounts of aglycosylated variants (Karnoup, A. S., Kuppannan, K. & Young, S. A. 2007, *J. Chromatogr. B, Analyt. Technol. Biomed. Life Sci.*, 859:178-191; Giorno, C., 2010, "Glycoengineering of monoclonal antibodies", PhD Thesis, University Konstanz). Our internal data also revealed that plant-produced mAbs often contain up to 30% of aglycosylated N-glycosylation sites in the Fc domain. Such data in comparison with CHO-cell-produced mAbs indicate higher heterogeneity of the final plant-produced product and might have detrimental effect on biological activity and pharmaco-kinetik characteristics of plant-produced mAbs.

However, efficient interaction with Fc receptors of effector cells for triggering a patient's immune system via enhanced ADCC and CDC might not be crucial for some therapeutic mAbs including the ones for treating cancers. Effector cell activation might not be necessary for mAbs that are to be used as modulators (agonists or antagonists) of signal transduction. Also, because of glycosylation of Fc is necessary for maintaining monoclonal antibody conformation and stability (Zheng, K., Bantoq, C. & Bayer, R. 2011, *Mabs*, 3:568-576; Mimura, Y. et al., 2000, *Mol Immunol.*, 37:697-706; Sondermann, P., et al., 2000, *Nature*, 406:267-273; Mimura, Y. et al., 2001, *J Biol Chem.*, 276:45539-45547), complete removal of glycosilation sites e.g. by site-directed mutagenesis may not be an optimal solution.

The modulation of glycosylation site occupancy in the Fc region of IgG antibodies may be useful in cases where combination therapy is used with the help of antibody cocktails targeting immune activating and suppressing molecules (Kojima, T., et al., 2010, *J. Immunol.*, 184:5493-5501), or, for example, in sequential treatment of HER2-positive cancers with tumor-targeting antibody trastuzumab, followed by treatment with a second antibody-agonist (anti-CD137) that activates the host innate immune system (Kohrt, H. E. et al., 2012, *J. Clin. Invest.*, 122:1066-1075).

Therefore, it is an object of this invention to provide a process for modulating the occupancy of N-glycosylation sites in the Fc region of plant-expressed immunoglobulins and in other plant-expressed glycoproteins by glycans. It is also an object to provide a process of modulating the occupancy of N-glycosylation sites in the Fc region of plant-expressed immunoglobulins and in other plant-expressed glycoproteins to different levels, such as to more than 90% or almost 100% or to 50% or less by glycans. It is another object to provide recombinant glycoproteins such as immunoglobulins (notably IgGs) expressed in plants and having a desired glycan occupancy at N-glycosylation sites, notably at the N-glycosylation site in the Fc region of IgGs.

SUMMARY OF THE INVENTION

These objects are achieved by:
(1) A process of producing a recombinant glycoprotein in a plant, in cells of a plant, or in plant cells, comprising expressing in said plant, in cells of said plant or in said plant cells a nucleic acid encoding a polypeptide, said polypeptide having an N-glycosylation site of consensus sequence Asn-X-Ser or Asn-X-Thr, X being any standard amino acid residue, wherein, if the Asn residue of said N-glycosylation site is assigned amino acid sequence position 0,
   (a) the amino acid residue at position +3 is selected from Thr, Ser, Gly, Leu, Ile, Val and Met; or
   (b) the amino acid residue at position −1 is selected from Glu and Asp;
whereby said recombinant glycoprotein can be produced.
(2) The process according to item 1, comprising expressing in said plant, in said cells of a plant or in said plant cells a nucleic acid encoding a polypeptide comprising an IgG heavy chain constant segment CH2 having an N-glycosylation site of consensus sequence Asn-X-Ser or Asn-X-Thr, X being any standard amino acid residue, wherein, if the Asn residue of said N-glycosylation site is assigned amino acid sequence position 0,
   (a) the amino acid residue at position +3 is selected from Thr, Ser, Gly, Leu, Ile, Val and Met; or
   (b) the amino acid residue at position −1 is selected from Glu and Asp.
(3) The process according to item 1 or 2, wherein said expressed polypeptide is post-translationally N-glycosylated at said N-glycosylation site in cells of the plant to form a recombinant glycoprotein.
(4) The process according to item 3, wherein the N-glycosylation at said N-glycosylation site is performed by the native glycosylation machinery of a plant to attach a plant-type N-glycans to the N-glycosylation site, or the plant or plant cells have a genetically-engineered N-glycosylation machinery such as for producing human-type or humanized N-glycans on the N-glycosylation.
(5) The process according to any one of items 1 to 4, wherein said polypeptide encoded by said nucleic acid comprises an IgG heavy chain constant region, preferably said polypeptide is or comprises an immunoglobulin G (IgG) heavy chain.
(6) The process according to any one of items 1 to 5, wherein said polypeptide encoded by said nucleic acid is a human immunoglobulin G (IgG) heavy chain except for the amino acid residue at position +3 or position −1 as defined in item 1.
(7) The process according to any one of items 1 to 6, further comprising isoating and/or purifying said recombinant glycoprotein from said plant or said plant cells.
(8) A process of modulating the glycosylation occupancy of an N-glycosylation site in a polypeptide upon expression in a plant or in plant cells, said polypeptide comprising an IgG heavy chain constant segment CH2 having said N-glycosylation site having consensus sequence Asn-X-Ser or Asn-X-Thr, X being any standard amino acid residue,
   said process comprising substituting, in a nucleic acid sequence encoding said polypeptide, the codon coding for the tyr or phe residue at position +3 counted from position 0 of the Asn residue of said N-glycosylation site by a codon coding for an amino acid residue selected from Thr, Ser, Gly, Leu, Ile, Val and Met, and
   expressing the nucleic acid sequence having the substitution made in the previous step in said plant or in said plant cells.
(9) A process of modulating the glycosylation occupancy of an N-glycosylation site in a polypeptide upon expression in a plant or in plant cells, said polypeptide comprising an IgG heavy chain constant segment CH2 having said N-glycosylation site having consensus sequence Asn-X-Ser or Asn-X-Thr, X being any standard amino acid residue,
   said process comprising substituting, in a nucleic acid sequence encoding said polypeptide, the codon coding for the tyr or phe residue at position −1 counted from position 0 of the Asn residue of said N-glycosylation site by a codon coding for an amino acid residue selected from Glu and Asp, and
   expressing the nucleic acid sequence having the substitution made in the previous step in said plant or in said plant cells.
(10) The process according to any one of items 1 to 9, wherein said plant is a higher plant, preferably a dicot plant, more preferably a Solanacea plant, more preferably a *Nicotiana* plant and most preferably *Nicotiana benthamiana*; and said plant cells are cells from a higher plant, preferably a dicot plant, more preferably a Solanacea plant, more preferably a *Nicotiana* plant and most preferably *Nicotiana benthamiana*.
(11) The process according to any one of items 1 to 10, further comprising co-expressing a second nucleic acid sequence in said plant, plant cells or cells of a plant, encoding a heterologous single-subunit oligosaccharyltransferase.
(12) The method of item 11, wherein the heterologous single-subunit oligosaccharyltransferase is the *Leishmania* STT3A protein, STT3B protein, STT3C protein, STT3D protein or combinations thereof.
(13) The process according to item 11 or 12, wherein said nucleic acid sequence encoding a polypeptide and said second nucleic acid sequence are both expressed transiently in said plant, preferably by *Agrobacterium*-mediated transfection.
(14) The process according to any one of items 11 to 13, wherein said nucleic acid sequence encoding a polypeptide and said second nucleic acid sequence are expressed in a plant by co-transfecting said plant with a first *Agrobacterium* containing a first DNA molecule comprising a T-DNA comprising a nucleic acid construct containing a DNA sequence of interest encoding a polypeptide having an N-glycosylation site, and transfecting said plant with a second *Agrobacterium* containing a second DNA molecule comprising a T-DNA comprising a nucleic acid construct containing a second DNA sequence encoding a heterologous single-subunit oligosaccharyltransferase; and expressing the first and the second DNA sequence to produce a glycosylated form of said polypeptide as said glycoprotein.
(15) The process according to any one of the preceding items, wherein the glycoprotein comprises two different polypeptide chains (is a heterodimeric or heterooligomeric glycoprotein), said process comprising expressing a nucleic acid sequence of interest encoding a polypeptide of a first subunit, said polypeptide having an N-glycosylation site of consensus sequence Asn-X-Ser or Asn-X-Thr, X being any standard amino acid residue, wherein if the Asn residue of said N-glycosylation site is assigned amino acid sequence position 0, the amino acid residues at position +3 or −1 may be as defined above; and expressing a nucleic acid sequence encoding another polypeptide of another subunit of the recombinant glycoprotein.

(16) A process of producing a recombinant glycoprotein in a plant, in cells of a plant, or in plant cells, comprising expressing in said plant, in cells of said plant or in said plant cells a nucleic acid sequence encoding a polypeptide having an N-glycosylation site and co-expressing a nucleic acid sequence encoding a heterologous single-subunit oligosaccharyltransferase.

(17) A process of producing a recombinant glycoprotein in a plant, comprising transfecting said plant with a first *Agrobacterium* containing a first DNA molecule comprising a T-DNA comprising a nucleic acid construct containing a DNA sequence of interest encoding a polypeptide having an N-glycosylation site, and transfecting said plant with a second *Agrobacterium* containing a second DNA molecule comprising a T-DNA comprising a nucleic acid construct containing a second DNA sequence encoding a heterologous single-subunit oligosaccharyltransferase; and expressing the first and the second DNA sequence to produce the a glycosylated form of said polypeptide as said glycoprotein.

(18) The process according to item 16 or 17, wherein the single-subunit oligosaccharyltransferase is the *Leishmania* STT3A protein, STT3B protein, STT3C protein, STT3D protein or combinations thereof.

(19) Recombinant glycoprotein comprising a polypeptide comprising an IgG heavy chain constant segment CH2 with a glycosylated N-glycosylation site of consensus sequence Asn-X-Ser or Asn-X-Thr, X being any standard amino acid residue, wherein if the Asn residue of said N-glycosylation site is assigned amino acid sequence position 0,
 (a) the amino acid residue at position +3 is selected from Thr, Ser, Gly, Leu, Ile, Val and Met; or
 (b) the amino acid residue at position −1 is selected from Glu and Asp.

(20) The recombinant glycoprotein according to item 19, wherein said recombinant glycoprotein is a glycoprotein expressed in a plant or in plant cells.

(21) The recombinant glycoprotein according to item 19 or 20, wherein said recombinant glycoprotein of item (a) has a glycosylation occupancy at said N-glycosylation site of at least 85%, more preferably at least 90%; or wherein said glycoprotein of item (b) has a glycosylation occupancy at said N-glycosylation site of at most 65%, preferably at most 55%.

(22) The recombinant glycoprotein according to any one of items 19 to 21, wherein said polypeptide comprises an IgG heavy chain constant region, preferably said polypeptide comprises an IgG heavy chain including variable and constant regions.

(23) The recombinant glycoprotein according to any one of items 19 to 22, wherein said polypeptide is a human IgG heavy chain except for the amino acid residue at position +3 or position −1 as defined in item 1.

(24) The recombinant glycoprotein according to item 22 or 23, wherein said polypeptide encodes a human IgG heavy chain of any one of types G1, G2, G3 and G4.

(25) The recombinant glycoprotein according to any one of items 19 to 24, wherein said polypeptide comprises a heavy chain region comprising
 (i) the amino acid sequence of SEQ ID NO: 1 except for the amino acid residue at position +3 or position −1 as defined in item 1;
 (ii) an amino acid sequence having a sequence identity of at least 95%, preferably at least 97% to the amino acid sequence of SEQ ID NO: 1 and having the amino acid residue at position +3 or position −1 as defined in item 1;
 (iii) an amino acid sequence having from 1 to 10, preferably from 1 to 5 amino acid substitutions, additions, and/or deletions to the amino acid sequence of SEQ ID NO: 1 but having the amino acid residue at position +3 or position −1 as defined in item 1.

(26) The recombinant glycoprotein according to any one of items 19 to 25, which is an IgG antibody or an Fc fragment of an IgG antibody.

(27) The recombinant glycoprotein according to item 19, which is an IgG antibody having a variable domain having affinity to CD20 or Her2/Neu.

(28) Pharmaceutical composition comprising the recombinant glycoprotein as defined in any one of items 19 to 27 and a pharmaceutically acceptable carrier.

(29) The recombinant glycoprotein according to any one of items 19 to 27 for use in therapy, such as for therapy of Her2/Neu positive cancer.

(30) Method of treating a patient suffering from Her2/Neu positive cancer, comprising administering to said patient an effective amount of said recombinant glycoprotein as defined in item 27.

(31) Nucleic acid encoding a polypeptide comprising an IgG heavy chain constant segment CH2 with an N-glycosylation site of consensus sequence Asn-X-Ser, X being any standard amino acid residue, wherein if the Asn residue of said N-glycosylation site is assigned amino acid sequence position 0,
 (a) the amino acid residue at position +3 is selected from Thr, Ser, Gly, Leu, Ile, Val and Met; or
 (b) the amino acid residue at position −1 is selected from Glu and Asp.

(32) The isolated nucleic acid of item 31, encoding a human IgG heavy chain constant region except for the amino acid residue at position +3 or −1 as defined in item 1.

(33) Nucleic acid construct comprising a plant-active promoter and operably linked thereto the nucleic acid as defined in item 31 or 32.

(34) Vector comprising the nucleic acid construct of item 33.

(35) Plant or plant cell comprising a nucleic acid construct of item 33 or the vector of item 34.

(36) The plant or plant cell according to item 35, further comprising a nucleic acid sequence encoding a heterologous single-subunit oligosaccharyltransferase.

(37) Plant or plant cell comprising a nucleic acid sequence encoding a heterologous single-subunit oligosaccharyltransferase.

(38) *Agrobacterium* mixture containing a first *Agrobacterium* containing a first DNA molecule comprising a T-DNA comprising a nucleic acid construct containing a DNA sequence of interest encoding a polypeptide having an N-glycosylation site, and a second *Agrobacterium* containing a second DNA molecule comprising a T-DNA comprising a nucleic acid construct containing a second DNA sequence encoding a heterologous single-subunit oligosaccharyltransferase.

(39) Recombinant glycoprotein comprising a polypeptide that is an IgG heavy chain, said polypeptide comprising an IgG heavy chain constant segment CH2 with a glycosylated N-glycosylation site of consensus sequence Asn-X-Ser or Asn-X-Thr, X being any standard amino acid residue, wherein if the Asn residue of said N-glycosylation site is assigned amino acid sequence position 0,
 (a) the amino acid residue at position +3 is selected from Thr, Ser, Gly, Leu, Ile, Val and Met; or
 (b) the amino acid residue at position −1 is selected from Glu and Asp.

(40) Process of producing a recombinant glycoprotein in a plant or plant cells, comprising expressing in said plant or said plant cells a nucleic acid sequence encoding a polypeptide comprising an IgG heavy chain constant segment CH2 having an N-glycosylation site of consensus sequence Asn-X-Ser or Asn-X-Thr, X being any standard amino acid residue, wherein, if the Asn residue of said N-glycosylation site is assigned amino acid sequence position 0,
 (a) the amino acid residue at position +3 is selected from Thr, Ser, Gly, Leu, Ile, Val and Met; or
 (b) the amino acid residue at position −1 is selected from Glu and Asp.

(41) A recombinant glycoprotein comprising a polypeptide comprising an IgG heavy chain constant segment CH2 with a glycosylated N-glycosylation site of consensus sequence Asn-X-Ser or Asn-X-Thr, X being any standard amino acid residue, wherein if the Asn residue of said N-glycosylation site is assigned amino acid sequence position 0,
 (a) the amino acid residue at position +3 is selected from Thr, Ser, Gly, Leu, Ile, Val and Met; or
 (b) the amino acid residue at position −1 is selected from Glu and Asp.

(42) A process of producing a recombinant glycoprotein in a plant, in cells of a plant, or in plant cells, comprising mutating a nucleic acid encoding a polypeptide having an N-glycosylation site of consensus sequence Asn-X-Ser or Asn-X-Thr, X being any standard amino acid residue, such that, if the Asn residue of said N-glycosylation site is assigned amino acid sequence position 0, the amino acid residue at position +3 and/or −1 is as defined in item (a) or (b) below, and expressing in said plant, in cells of said plant or in said plant cells the obtained (mutated) nucleic acid, thereby producing said recombinant glycoprotein;
 (a) the amino acid residue at position +3 is selected from Thr, Ser, Gly, Leu, Ile, Val and Met, whereby Thr is preferred; or
 (b) the amino acid residue at position −1 is selected from Glu and Asp.

Mammalian proteins that are expressed in plants sometimes have a glycosylation occupancy at N-glycosylation sites lower than those obtained by expression in animal expression systems. The inventors have surprisingly found that the glycan occupancy at N-glycosylation sites of proteins expressed in plants can be modified by suitably selecting the amino acid residue at position −1 or +3 counted from the Asn residue of the N-glycosylation site of the conventional consensus sequence Asn-X-Ser/Thr, if the Asn residue is assigned position 0. Preferably, a high or increased glycosylation occupancy at N-glycosylation sites upon expression in plants can be achieved by placing any of the following amino acid residues at position +3: Thr, Ser, Gly, Leu, Ile, Val and Met. A low or reduced glycosylation occupancy at N-glycosylation sites upon expression in plants can be achieved by placing any of the following amino acid residues at position −1: Glu and Asp. Thus, the invention allows modifying the glycosylation occupancy at N-glycosylation sites or proteins upon expression in plants. The invention also allows producing a recombinant glycoprotein in a plant or in plant cells having a desired glycosylation occupancy at N-glycosylation sites. The invention also provides recombinant glycoproteins having the amino acid substitution indicated above at one or more N-glycosylation sites of consensus sequence Asn-X-Ser/Thr.

The inventors have further found that the glycosylation occupancy at N-glycosylation sites of a glycoprotein expressed in a plant or in plant cells can be increased by co-expressing in the plant or in the plant cells a heterologous single-subunit oligosaccharyltransferase. This embodiment can be employed in combination with the amino acid exchanges at positions +3 and −1 defined above or independent therefrom.

BRIEF DESCRIPTION OF THE FIGURES

FIG. 1: A. Sequence of Immunoglobulin Gamma 1 heavy chain constant region (SEQ ID NO: 1). The positions are numbered according to the EU index as in Kabat (Kabat, E. A. et al., 1991, Sequences of Proteins of Immunological Interest, (DHHS, Washington, D.C.), 5th edition). N-glycosylation site (shown in bold, underlined). The amino acid residue Asn at position 300 is the N-glycosylation site of consensus sequence Asn-X-Ser/Thr the glycosylation occupancy of which is modulated in the presence invention. Amino acid positions for amino acid substitutions made and described in the Examples are shown in italics and bold. Position 300 in the numbering shown is amino acid position +3 used in the invention for increasing the glycosylation occupancy at the N-glycosylation site. Position 296 in the numbering shown is amino acid position −1 used in the invention for decreasing the glycosylation occupancy at the N-glycosylation site. B Amino acid sequence (SEQ ID NO: 2) of the cloned, His-tagged version of *Leishmania major* STT3-D gene (LmJF35.1160, acc. no. E9AET9). Added amino acid residues are underlined.

FIG. 4: Amino acid sequences of variable (SEQ ID NO: 5) and generic constant Kappa light chain (SEQ ID NO: 6) regions of recombinant Trastuzumab and nucleic acid sequences coding therefor (SEQ ID NO: 3 and SEQ ID NO: 4, respectively).

FIG. 5: Amino acid sequences of variable (SEQ ID NO: 8) and constant heavy chain (SEQ ID NO: 10) regions of recombinant Trastuzumab IgG1 and nucleic acid sequences coding therefor (SEQ ID NO: 7 and SEQ ID NO: 9, respectively).

FIG. 6: Amino acid sequences of variable (SEQ ID NO: 12) and generic constant Kappa light chain (SEQ ID NO: 14) regions of recombinant Rituximab and nucleic acid sequences coding therefor (SEQ ID NO: 11 and SEQ ID NO: 13, respectively).

FIG. 7: Amino acid sequences of variable (SEQ ID NO: 16) and constant heavy chain (SEQ ID NO: 18) regions of recombinant Rituximab IgG1 and nucleic acid sequences coding therefor (SEQ ID NO: 15 and SEQ ID NO: 17, respectively).

DETAILED DESCRIPTION OF THE INVENTION

Figure 2:
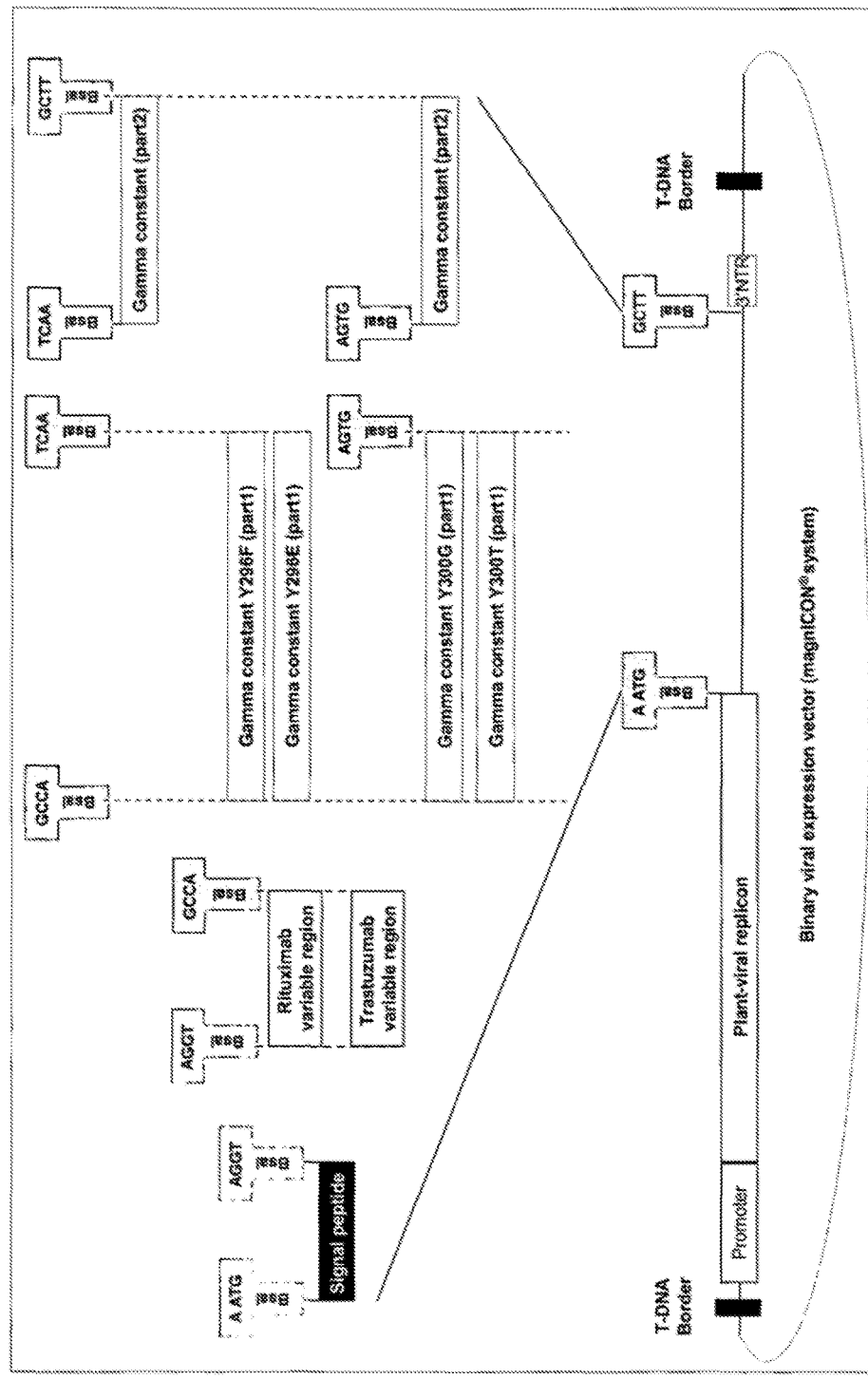
FIG. 2: A. Cloning scheme of Rituximab and Trastuzumab amino acid sequence-encoding nucleic acid modules for producing heavy IgG chains having glycosylation-modified constant regions. Type IIS restriction enzymes such as BsaI were used for seamless assembly of nucleic acid sequence modules. B. Cloning scheme of *Leishmania major* STT3-D (LmJF35.1160, acc. no. E9AET9) a *Zea mays* codon-optimized version with a C-terminal His-tag. Type IIS restriction enzymes such as BsaI were used for seamless assembly of nucleic acid sequence modules. C. Amino acid sequence of *Leishmania major* STT3-D (LmJF35.1160, acc. no. E9AET9), SEQ ID NO: 21. D. Amino acid sequence of the cloned, His-tagged version of *Leishmania major* STT3-D, SEQ ID NO: 22.
Figure 2:
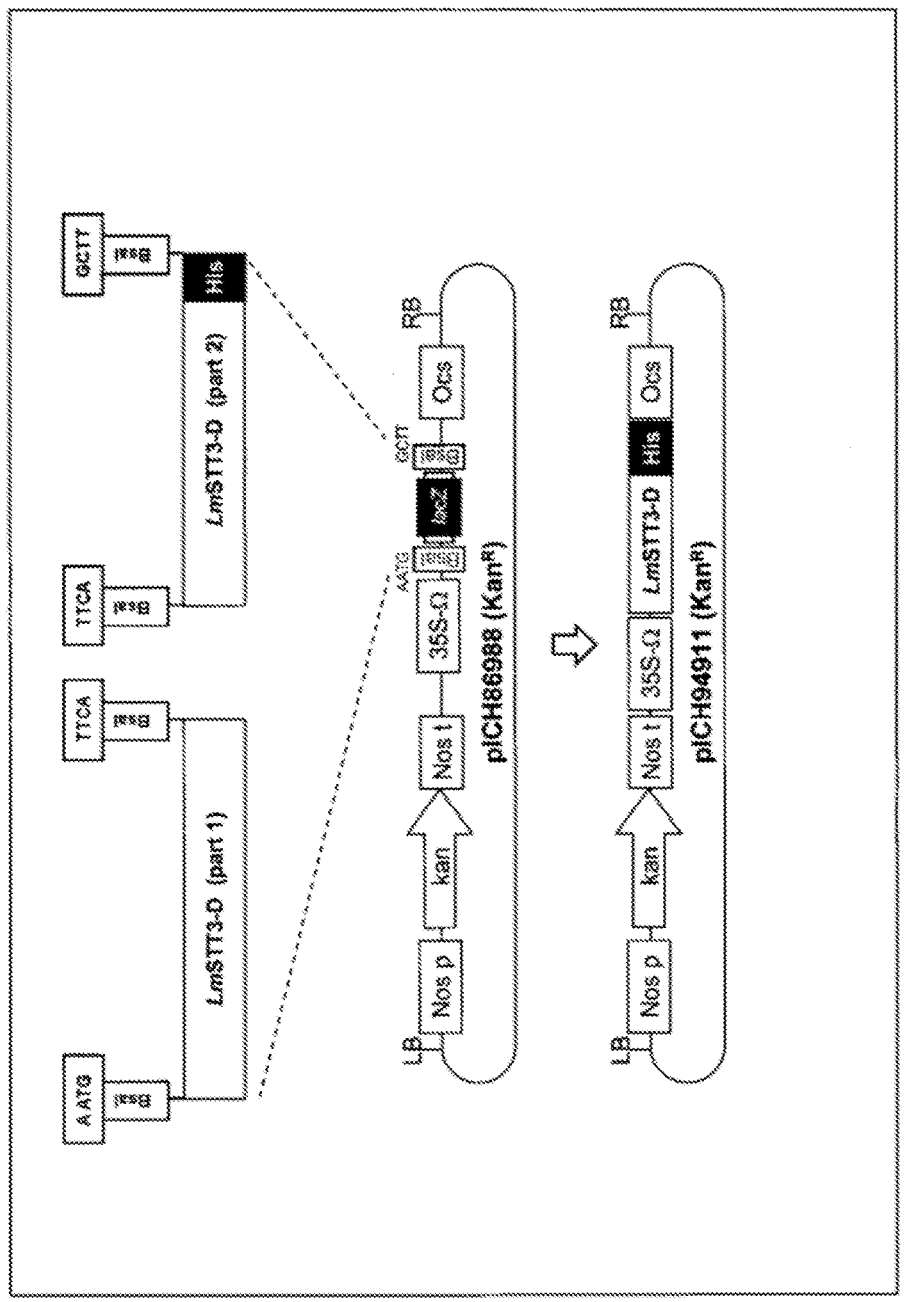

The processes of the invention allow production of a recombinant glycoprotein by expression in a plant or in plants cells. However, the recombinant glycoprotein of the invention is not limited to expression in a plant or in plant cells. Generally, many different expression systems that are based on different production hosts (bacteria, fungi, animal, insect and plant cells) and expression vectors designed either for stable transgenic or transient expression can be used for producing the recombinant glycoprotein. Such systems are generally known to the skilled person and described in the literature (for review see: Huang, C. J., Lin, H. & Yang, X. 2012, J. Ind. Microbiol. Biotechnol., 39:383-399; Hou, J., Tyo, K. E., Liu, Z. et al., 2012, FEMS Yeast Res., 12:491-510; Martinez, J. L, Liu, L., Petranovic, D. et al., 2012, Curr. Opin. Biotechnol., April 12. [Epub ahead of print]; Su, X., Schmitz, G., Zhang, M. et al., 2012, Adv App/Microbiol., 81:1-61; Ghaderi, D., Zhang, M., Hurtado-Ziola, N.& Varki, A. 2012, Biotechnol. Genet. Eng. Rev., 28:147-175; Egelkrout, E., Rajan, V. & Howard, J. A., 2012, Plant Sci., 184:83-101). The choice of the expression system depends on various factors such as cost of materials or the speed and scale desired for the protein production.

In one embodiment, the recombinant glycoprotein is produced in a plant or in plant cells, as in the production process and modifying processes of the invention. Among plant expression systems, plant virus-based transient expression systems are advantageous in terms of speed or production, yield and universality with regard to production of different types of recombinant proteins including hetero-oligomeric proteins like monoclonal antibodies. Another advantage of plant expression systems is the ability to provide for the production of plant viral particles by allowing expression of plant viral coat protein or fusion proteins from the expression vector (Werner, S. et al., 2006, Proc. Natl. Acad. Sci. USA, 103:17678-17683; WO2007031339). Plant expression systems suitable for the present invention are described in numerous research articles, reviews and patent documents (e.g. Marillonnet, S., Thoeringer, C., Kandzia, R. et al., 2005, Nat. Biotechnol., 23:718-723; Giritch, A., Marillonnet, S., Engler, C., et al., 2006, Proc. Natl. Acad. Sci. USA, 103:14701-14706; Gleba, Y., Klimyuk, V. & Marillonnet, S. 2007, Curr. Opin. Biotechnol., 18:134-141; Klimyuk, V., Pogue, G., Herz, S. et al., 2012, Curr Top Microbiol Immunol., April 15; WO2005049839; WO2006079546). WO2005049839 contains detailed information of possible plant viral expression vectors including sequence information thereof. The design of viral vectors, cloning strategy and expression of recombinant proteins including immunoglobulins is described in detail in W0002006079546 and herein in Example 1. Cloning of a nuceic acid sequence encoding a polypeptide to be expressed is part of the general knowledge of the skilled person. A particularly convenient cloning strategy is modular cloning for seamless stitching together different DNA fragments, which was established in our laboratory (Engler, C., Kandzia, R. & Marillonnet, S., 2008, *PLoS One*, 3:e3647; Weber E., Engler, C., Guetzner, R. et al., 2011, *PLoS One*, 6:e16765; Engler, C. & Marillonnet, S. 2011, *Methods Mol Biol.*, 729:167-81; Thieme, F., Engler, C., Kandzia, R. et al., 2011, *PLoS One*, 6:e20556). This system is simple, reliable, convenient to use and allows fast construct engineering of any complexity. A general scheme of seamless assembly of a binary vector comprising in T-DNA a construct comprising a nucleic acid sequence encoding IgG1 heavy chains for rituximab or trastuzumab from four gene modules and a viral vector are shown in FIG. 2A. Seamless assembly of heavy chain modules is provided by a type IIS restriction endonuclease. In this case, BsaI was used. The polypeptide to be expressed may be provided with an N-terminal signal peptide by placing a coding sequence coding for a signal peptide at the 5' end of the nucleic acid sequence encoding the polypeptide. Heavy chains of IgG of interest and different Fc mutant variants were assembled using this strategy and cloned into appropriate viral vectors in the Examples below. For expressing antibodies, a nucleic acid sequence encoding the heavy chain (HC) may be cloned in a TMV-based vector, and a nucleic acid sequence encoding the light chain (LC) may be cloned in a PVX-based vector (see FIG. 3). In the Examples below, binary vectors were used that can be transformed into plant cells using *Agrobacterium*. Other transformation methods may also be used. The final expression vectors may be tested for the expression in plants.

Expressing the nucleic acid sequence (a polynucleotide) encoding the polypeptide of the invention in a plant or in plant cells generally comprises transforming the plant or the plant cells with a nucleic acid molecule (also referred to herein as "vector") comprising a nucleic acid construct containing the nucleic acid sequence. The nucleic acid sequence encoding the polypeptide having the N-glycosylation site to be glycosylated is also referred to herein as "nucleic acid sequence of interest". If two or more different polypeptides each having an N-glycosylation site are to be expressed, e.g. for producing a heterodimeric or hetero-oligomeric glycoprotein, there are two or more different nucleic acid sequences of interest.

The nucleic acid molecule is generally a DNA molecule. In this case, the nucleic acid sequence of interest contained therein is a DNA. An example of the DNA molecule is a binary vector that may be transformed into plant cells by *Agrobacterium*-mediated transformation. Another example of a nucleic acid molecule is a DNA vector to be transformed by particle bombardment.

The polypeptide of the recombinant glycoprotein may be expressed in the processes of the invention in stably transformed transgenic plants or cells thereof. "Stably transformed" in the case of plant cells means that the nucleic acid sequence(s) of interest is (are) incorporated into chromosomal DNA such that it transferred to daughter cells. "Stably transformed" in the case of (whole) plants means that all somatic cells of the plant contain the nucleic acid sequence(s) of interest incorporated into chromosomal DNA such that it (they) can be inherited to progeny plants. Preferably, however, the recombinant glycoprotein is expressed by transient expression from transiently transfected plants. The term "transient" means that no selection methods are used for selecting cells or plants transfected with the nucleic acid molecule (vector) or with the nucleic acid construct from non-transfected cells or plants using, e.g. a selectable agent and a selectable marker gene capable of detoxifying the selectable agent. As a result, the transfected nucleic acid is generally not stably introduced into plant chromosomal DNA. Transient expression methods make use of the effect of transfection in the very plant cells transfected. Transient expression is preferred, as mentioned above, inter alia due to the speed of expression. Further, there is no need for a selectable marker gene for selecting plant cells or plants, whereby no antibiotic resistance gene or a herbicide resistance gene needs to be inserted into plants, and spread of such genes in the environment with these plants can also be avoided. In the case of transient transfection of plants by *Agrobacterium*-mediated transfection, T-DNA of the binary vector or Ti-plasmid is preferably free of a selectable marker gene such that no such marker gene is inserted into plant cells.

Various methods for introducing a nucleic acid molecule, such as a DNA molecule, into a plant or plant cells for transient expression are known. In the invention, agrobacteria are preferably used for transfecting plants with the nucleic acid molecule (vector) or nucleic acid construct e.g. by agroinfiltration. A system and method for large scale infiltration of plants using agrobacteria is described in WO2009095183. In another embodiment, plants or plant parts are sprayed with a suspension containing cells of an *Agrobacterium* strain, which is well suitable for large scale applications to many plants such as to plants on a farm field. Such spray transfection processes are described inter alia in WO2012/019660.

The *Agrobacterium* strain may belong to the species *Agrobacterium tumefaciens* or *Agrobacterium rhizogenes* that are commonly used for plant transformation and transfection and which are known to the skilled person from general knowledge. The *Agrobacterium* strain to be used in the processes of the invention comprises a DNA molecule (Ti-plasmid) as said nucleic acid molecule, comprising a nucleic acid construct containing a DNA sequence of interest. The DNA sequence of interest may encode the polypeptide of the invention or more than one polypeptide to be expressed. The nucleic acid construct is typically present in T-DNA of Ti-plasmids for introduction of the nucleic construct into plant cells by the secretory system of the *Agrobacterium* strain. On at least one side or on both sides, the nucleic acid construct is flanked by a T-DNA border sequence for allowing transfection of said plant(s) and introduction into cells of said plant of said nucleic acid construct. Preferably, said nucleic acid construct is present in T-DNA and flanked on both sides by T-DNA border sequences.

Preferably, the nucleic acid construct is present in T-DNA of a Ti-plasmid of the *Agrobacterium* strain. Ti-plasmids may contain a selectable marker outside of said T-DNA for allowing cloning and genetic engineering in bacteria. However, the T-DNA that is transferred into cells of said plant preferably does not contain a selectable marker that would, if present, allow selection of plant or plant cells containing said T-DNA. Examples of selectable marker genes that should, in this embodiment, not be present in T-DNA of the DNA molecule (Ti-plasmid) are an antibiotic resistance gene or a herbicide resistance gene. If the processes of the invention use transient transfection and expression of said nucleic acid sequence of interest (or said polypeptide), the processes do not comprise a step of selecting for plant cells having incorporated the nucleic acid molecule of the invention by using such antibiotic resistance gene or a herbicide resistance gene. Accordingly, no antibiotic resistance gene or a herbicide resistance gene needs to be incorporated into said plants, whereby the probability of spreading such genes in the environment is low in the processes of the invention.

As indicated above, for expression of hetero-oligomeric proteins such as antibodies as the glycoprotein of the invention, all subunits (polypeptide chains) may be expressed in the same cells of a plant or plant cells, preferably transiently. This may be done by co-transfecting a plant or plant cells with a mixture of agrobaceria, one for each subunit or polypeptide. Thus, the invention provides a process of producing a recombinant glycoprotein comprising two or more (preferably: two) different polypeptide chains in a plant such as an IgG antibody, the process comprising transfecting the plant with an *Agrobacterium* containing a DNA molecule comprising a T-DNA comprising a nucleic acid construct containing the DNA sequence of interest encoding a polypeptide of a first subunit of the glycoprotein, said polypeptide having an N-glycosylation site (as defined above with the amino acid residues at positions +3 and −1 as defined herein), and transfecting said plant with an *Agrobacterium* containing a (another) DNA molecule comprising a (another) T-DNA comprising a nucleic acid construct containing a (another) DNA sequence encoding the polypeptide of another subunit of the glycoprotein; and expressing the DNA sequences to produce the glycoprotein. The polypeptide of the another subunit may or may not contain an N-glycosylation site. If it has an N-glycosylation site, it may or may not have the amino acid residues at positions +3 and −1 as defined herein. Preferably, the polypeptide of the another subunit having an N-glycosylation site also has the amino acid residues at positions +3 and −1 as defined herein for achieving a high N-glycan occupancy at all N-glycosylation sites.

However, it is also possible to express the multiple polypeptides of multiple subunits of a hetero-oligomeric protein separately in different plants or plant cells. The separately expressed polypeptides, at least one of which is a produced according to the process of the invention, may be separately purified and reconstituted in vitro to form the recombinant hetero-oligomeric protein.

The nucleic acid construct comprises the nucleic acid sequence of interest such that the latter is expressible in plant cells. For this purpose, the nucleic acid sequence of interest may be, in said nucleic acid construct, under the control of a promoter active in plant cells. Examples of the nucleic acid sequence of interest are a DNA encoding a DNA viral replicon or an RNA viral replicon, or a gene to be expressed. The gene produces, upon expression in the plant, the polypeptide. Also the viral replicons may encode the polypeptide to be expressed in cells of the plant(s). The nucleic acid construct may comprise, in addition to the nucleic acid sequence, other sequences such as regulatory sequences for expression of the nucleic acid sequence of interest, such as a transcription promoter and terminator. The nucleic acid sequence may additionally encode a signal peptide to be expressed as an N-terminal signal peptide of the polypeptide. The nucleic acid construct may comprise a further gene to be expressed, e.g. a gene encoding a suppressor of gene silencing such as the P19 protein. Expression of such further gene may be under the control of the same or a different promoter as the promoter used for expressing the protein of the invention. *Agrobacterium*-mediated gene transfer and vectors therefor are known to the skilled person, e.g. from the references cited above or from text books on plant biotechnology such as Slater, Scott and Fowler, Plant Biotechnology, second edition, Oxford University Press, 2008.

As used herein, the term "promoter active in plant cells" means a DNA sequence that is capable of controlling (initiating) transcription in a plant cell. This includes any promoter of plant origin, but also any promoter of non-plant origin which is capable of directing transcription in a plant cell, i.e., certain promoters of viral or bacterial origin such as the cauliflower mosaic virus 35S promoter (CaMV35S promoter) (Harpster et al. (1988) *Mol Gen Genet.* 212(1): 182-90, the subterranean clover virus promoter No 4 or No 7 (WO9606932), or T-DNA gene promoters but also tissue-specific or organ-specific promoters including but not limited to seed-specific promoters (e.g., WO89/03887), organ-primordia specific promoters (An et al. (1996) *Plant Cell* 8(1):15-30), stem-specific promoters (Keller et al., (1988) *EMBO J.* 7(12): 3625-3633), leaf specific promoters (Hudspeth et al. (1989) *Plant Mol Biol.* 12: 579-589), mesophyl-specific promoters (such as the light-inducible Rubisco promoters), root-specific promoters (Keller et al. (1989) *Genes Dev.* 3: 1639-1646), tuber-specific promoters (Keil et al. (1989) *EMBO J.* 8(5): 1323-1330), vascular tissue specific promoters (Peleman et al. (1989) *Gene* 84: 359-369), stamen-selective promoters (WO 89/10396, WO 92/13956), dehiscence zone specific promoters (WO 97/13865) and the like. For transient expression, constitutive promoters are preferably used. However, constitutive promoters may be tissue-specific or organ-specific, in one embodiment they are not tissue-specific or organ-specific. Preferred promoters are those used in the Examples described below.

Protein glycosylation takes place in the ER and/or Golgi apparatus of eukaryotic cells. For targeting newly made polypeptides into these compartments, the polypeptide having the N-glycosylation site to be glycosylated should be provided with a suitable signal peptide at the N-terminus. Use of such signal peptides for ER and/or Golgi targeting are known. Suitable signal peptides are used for expression in plants of beta(1,4)-galactosyltransferase which is described in several publications that are cited below.

Herein, the term "construct" means a recombinant construct comprising a nucleotide sequence of interest. Preferably, the construct encodes at least the polypeptide having the N-glycosylation site having the amino acid residues at positions +3 and −1 according to the invention. Other nucleic acid sequences encoding further polypeptides may also be included in the same or other constructs.

In embodiments wherein strong expression of the polypeptide is desired, the nucleic acid construct may encode a viral vector that can replicate in plant cells to form replicons of the viral vector. In order to be replicating, the viral vector and the replicons contain an origin of replication that can be recognized by a nucleic acid polymerase present in plant cells, such as by the viral polymerase expressed from the replicon. The viral vectors may be RNA viral vectors, since they form RNA replicons. In case of RNA viral vectors, the replicons may be formed by transcription under the control of a promoter active in plant cells, from the DNA construct after the latter has been introduced into plant cell nuclei. In case of DNA replicons, DNA replicons may be formed by recombination between two recombination sites flanking the sequence encoding the viral relicon in the DNA construct, e.g. as described in WO00/17365 and WO 99/22003. If the replicon is encoded by the DNA construct, RNA replicons are preferred. Use of DNA and RNA viral vectors (DNA or RNA replicons) has been extensively described in the literature over the years. Some examples are the following patent publications: WO2008028661, WO2007137788, WO 2006003018, WO2005071090, WO2005049839, WO02097080, WO02088369, WO02068664. An example of DNA viral vectors are those based on geminiviruses. For the present invention, viral vectors or replicons based on plant RNA viruses, notably those based on plus-sense single-stranded RNA viruses may be used. Accordingly, the viral replicon may be a plus-sense single-stranded RNA replicon. Examples of such viral vectors those based on tobacco mosaic virus (TMV) and potex virus X (PVX). "Based on" means that the viral vector uses the replication system of these viruses. Potexvirus-based viral vectors and expression systems are described in EP2061890 or WO2008/028661. Many other plant viral replicons are described in the patent publications mentioned above.

Agrobacterium strains usable in the invention are those that are generally used in the art for transfecting or transforming plants. Generally, binary vector systems and binary strains are used, i.e. the vir genes required for transfer of T-DNA into plant cells on the one hand and the T-DNA on the other hand are on separate plasmids. Examples of usable Agrobacterium strains are given in the article of Hellens et al., Trends in Plant Science 5 (2000) 446-451 on binary Agrobacterium strains and vector systems. In the context of a binary Agrobacterium strain, the plasmid containing the vir genes is referred to as "vir plasmid" or "vir helper plasmid". The plasmid containing the T-DNA to be transfected is the so-called binary vector that is also referred to herein as "DNA molecule" or "vector". The term "strain" or "Agrobacterium strain" relates to components of the Agrobacterium other than the binary vector. Thus, herein, a binary Agrobacterium strain not containing a binary vector and after introduction of a binary vector are referred to by the same strain name.

Plants may be transiently transfected by providing parts of a plant with a suspension, preferably an aqueous suspension, containing cells of the Agrobacterium strain that comprises the nucleic acid molecule described above. The suspension of agrobacteria may be produced as follows. The DNA molecule or vector containing the nucleic acid construct may be transformed into the Agrobacterium strain, and transformed Agrobacterium cultures may be grown optionally under application of selective pressure for maintenance of said DNA molecule. In one method, the Agrobacterium strain to be used is then inoculated into a culture medium and grown to a high cell concentration. Larger cultures may be inoculated with small volumes of a highly concentrated culture medium for obtaining large amounts of the culture medium. Agrobacteria are generally grown up to a cell concentration corresponding to an OD at 600 nm of at least 1, typically of about 1.5. Such highly concentrated agrobacterial suspensions are then diluted to achieve the desired cell concentration for transfection. For diluting the highly concentrated agrobacterial suspensions, water is used. The water may contain a buffer or salts. The water may further contain a surfactant such as those described in WO2012/019660.

Preferred embodiments of the production process of the invention using Agrobacterium-based transient expression are, inter alia, the following two processes:

a process of producing a recombinant glycoprotein in a plant, comprising transfecting a plant or parts thereof with a suspension containing cells of an Agrobacterium strain comprising a nucleic acid molecule comprising a nucleic acid construct containing a nucleic acid sequence, said nucleic acid sequence encoding a polypeptide, said polypeptide having an N-glycosylation site of consensus sequence Asn-X-Ser/Thr, X being any standard amino acid residue, wherein, if the Asn residue of said N-glycosylation site is assigned amino acid sequence position 0, (a) the amino acid residue at position +3 is selected from Thr, Ser, Gly, Leu, Ile, Val and Met; or (b) the amino acid residue at position −1 is selected from Glu and Asp;

a process of producing a recombinant glycoprotein in a plant, comprising providing parts of said plant with an aqueous suspension containing cells of an Agrobacterium strain comprising a nucleic acid molecule comprising a nucleic acid construct containing a nucleic acid sequence, said nucleic acid sequence encoding a polypeptide comprising an IgG heavy chain constant segment CH2 having an N-glycosylation site of consensus sequence Asn-X-Ser/Thr, X being any standard amino acid residue, wherein, if the Asn residue of said N-glycosylation site is assigned amino acid sequence position 0, (a) the amino acid residue at position +3 is selected from Thr, Ser, Gly, Leu, Ile, Val and Met; or (b) the amino acid residue at position −1 is selected from Glu and Asp;

a process of producing a recombinant glycoprotein comprising two or more different polypeptide chains (subunits) in a plant such as an IgG antibody, comprising transfecting said plant with an Agrobacterium containing a DNA molecule comprising a T-DNA comprising a nucleic acid construct containing the DNA sequence of interest encoding a polypeptide of a first subunit of the glycoprotein, said polypeptide having an N-glycosylation site of consensus sequence Asn-X-Ser or Asn-X-Thr, X being any standard amino acid residue, wherein if the Asn residue of said N-glycosylation site is assigned amino acid sequence position 0, the amino acid residues at position +3 or −1 may be as defined above; and transfecting said plant with an Agrobacterium containing a DNA molecule comprising a T-DNA comprising a nucleic acid construct containing a DNA sequence encoding the polypeptide of another subunit of the glycoprotein; and expressing the DNA sequences to produce the glycoprotein.

The polypeptide to be expressed in the processes of the invention is generally heterologous to the plant in which (or in cells of which) it is expressed in the invention, i.e. the plant or its part does not produce the protein naturally. It is possible and desired to optimise codon usage of a nucleic acid sequence of interest encoding the polypeptide(s) for expression in plants, notably in the plant employed for expressing them. Codon optimisation is a standard method for increasing expression yields of proteins such as animal proteins in plants. Codon-optimised genes and nucleic acid sequences for expression in plants or in a plant of a particular genus or species can also be ordered from commercial sources such as Entelechon GmbH, Regensburg, Germany.

Plants or cells thereof that may be used for expressing the polypeptide and for producing the recombinant glycoprotein are not particularly limited. Preferred are multi-cellular plants, notably higher plants. Both monocot and dicot plants can be used. Plants that are not used for production of human food or animal feed are preferred. Examples are *Nicotiana* species such as *N. tabacum* and *N. benthamiana*. The latter is most preferred.

Regarding the glycans attached to the N-glycosylation site of the polypeptide, there are no particular limitations in the present invention. As described in more detail below, the types of glycans produced and attached depend on the organisms used for expressing the polypeptide. Also among plants, the glycans attached depend on whether a plant has a native or a genetically-engineered glycosylation system. Thus, herein, an N-glycosylation site of the polypeptide is considered N-glycosylated or having an N-linked glycan ("N-glycan"), if the N-glycosylation site carries any glycan of any size.

Plants naturally produce glycoproteins including glycoproteins having N-linked glycans. Thus, plants naturally have the necessary machinery for this type of post-translational modification. The N-glycosylation of the polypeptide expressed according to the invention to form the recombinant glycoprotein thus takes place in the plant cells where the polypeptide is expressed. Plants or cells thereof used for the processes of the invention may have the glycosylation machinery of a wild-type plant. In this case, N-glycans attached to the N-glycosylation site will be plant-type glycans. Plant-type glycans differ in some respects from those produced in animals cells. In plants, beta(1,2)-xylose and alfa(1,3)-fucose residues have been shown to be linked to the core Man3GlucNAc2-Asn of glycans, whereas they are not detected on mammalian glycans, where sialic acid residues and terminal beta(1,4)-galactosyl structures occur instead. The unique N-glycans added by plants may impact both immunogenicity and functional activity of the protein and, consequently, may represent a limitation for plants to be used as a protein production platform. Indeed, the immunogenicity of beta(1,2)-xylose residues and alfa(1,3)-fucose in mammals has been described (Bardor et al., 2003, Glycobiology 13: 427). The enzyme that catalyses the transfer of xylose from UDP-xylose to the core β-linked mannose of protein-bound N-glycans is beta(1,2)-xylosyltransferase ("XylT", EC 2.4.2.38). The beta-1,2-xylosyltransferase is an enzyme unique to plants and some non-vertebrate animal species and does not occur in human beings or in other vertebrates. WO2007107296 describes the identification and cloning of beta-1,2-xylosyltransferases from the genus *Nicotiana* such as *Nicotiana benthamiana*. The enzyme that catalyses the transfer of fucose from GDP-fucose to the core β-linked N-acetyl glucosamine (GlcNAc) of protein-bound N-glycans is alfa(1,3)-fucosyltransferase ("FucT", EC 2.4.1.214). WO2009056155 describes an alfa(1,3)-fucosyltransferase cDNA sequence from *Nicotiana benthamiana*. Thus, in order to avoid N-glycans containing plant-type beta(1,2)-xylose residues and/or alfa(1,3)-fucose at the N-glycoslation, plants (or cells thereof) that do not express beta-1,2-xylosyltransferase and/or alfa(1,3)-fucosyltransferase, respectively, may be employed in the present invention. Such plants and their use have been described. WO2008141806 describes knock-outs in two alfa(1,3)-fucosyltransferase genes and in one beta(1,2)-xylosyltransferase gene in *Arabidopsis thaliana*. WO2009056155 describes an RNA interference strategy for the generation of *Nicotiana benthamiana* plants which are deficient in the formation of beta-1,2-xylosyl structures as well as devoid of alfa-1,3-fucosyl structures on heterologous glycoproteins. Yin et al. (2011, Protein Cell 2:41) report downregulation of the expression of the endogenous xylosyltranferase and fucosyltransferase in *Nicotiana tabacum* using RNA interference (RNAi) strategy. They found that xylosylated and core fucosylated N-glycans were significantly, but not completely, reduced in the glycoengineered lines. WO2010145846 describes knock-outs of the two beta(1,2)-xylosyltransferase genes in *Nicotiana benthamiana*. The homozygous combination of the four beta(1,2)-xylosyltransferase null alleles proved to be sufficient for the elimination of the complete beta-1,2-xylosyltransferase activity in *Nicotiana benthamiana*. WO2013050155 describes plants of the genus *Nicotiana* which are deficient in alfa(1,3)-fucosyltransferase and beta(1,2)-xylosyltransferase activity, which plants may be applied as host plants or host cells to produce heterologous glycoproteins according to the present invention.

Alternatively or, preferably, additionally, the plants used for the processes of the invention may be genetically-engineered to express a beta(1,4)-galactosyltransferase that may be derived from an animal or from human for attaching beta(1,4)-galactosyl structures. Beta(1,4)-galactose has been introduced into plant-produced glycoproteins by expression of human beta(1,4)-galactosyltransferase I (GalT) (Bakker et al., 2001, Proc. Natl. Acad. Sci. USA 98: 2899), and chicken and zebrafish beta(1,4)-galactosyltransferase I (WO2008/125972). Bakker et al. (2006, Proc. Natl. Acad. Sci. USA 103: 7577) and WO2003/078637 describe a fusion of human GalT to the cytoplasmic tail, transmembrane domain, and stem region (CTS domain) of *Arabidopsis thaliana* xylosyltransferase (XylT). They also found that, in tobacco, addition of this CTS domain caused a sharp reduction of N-glycans with core-bound xylose and fucose residues. Vezina et al. (2009, Plant. Biotechnol. J. 7: 442) and WO2008/151440 fused GalT to the membrane anchorage domain of the N-acetylglucosaminyltransferase I (GNTI) from tobacco, in order to allocate GalT activity in the early plant secretory pathway. Glycans from the *N. benthamiana* plants expressing the GNTI-GalT fusion comprised galactosylated and non-galactosylated hybrids and immature oligomannose N-glycans, and contained no detectable alfa(1, 3)-fucose and beta(1,2)-xylose residues. WO2008/125972 replaced the chicken and zebrafish CTS domain with the CTS of rat sialyltransferase. The zebrafish GalT having substituted its amino-terminal for the CTS region of rat sialyltransferase, produced mainly biantennary, double galactosylated N-glycans in *N. benthamiana*. Strasser et al. (2009, J. Biol. Chem. 284: 20479) fused human GalT to the rat sialyltransferase CTS domain. This fusion protein was expressed in *N. benthamiana* which lacks plant-specific beta(1,2)-xylosyltransferase and core alfa(1,3)-fucosyltransferase activities and expresses anti-human immunodeficiency virus antibody. EP 2551348 A describes production of galactosylated N-glycans in plants. EP 1 137 789 A describes expression of a beta(1,4)-galactosyltransferase in a plant.

In a preferred embodiment, a plant (or cells thereof) is used that expresses a beta(1,4)-galactosyltransferase and has no or little activity of alfa(1,3)-fucosyltransferase and beta (1,2)-xylosyltransferase.

After production of the glycoprotein in a plant or in plant cells, it can be purified using generally known methods. In one embodiment, the glycoprotein is an immunoglobulin IgG, more preferably an IgG1, that may be purified using protein A affinity chromatography. Purification can then involve other types of column chromatography using a matrix having affinity to the purification tag, if necessary. Detailed description of purification protocols for two representatives of IgG1 subclass immunoglobulins, rituximab and trastuzumab, are provided in Examples 2 and 3, respectively. Purification methods and detailed protocols of different classes and subclasses of immunoglobulins, especially belonging to the class IgG, are known in the art in research community and industry and described in numerous publications (Danielsson, A. et al., 1988, *J. Immunol. Meth.*, 115:79-88; Kleine-Tebbe, J. et al., 1995, *J. Immunol. Meth.*, 179:153-164; Denizli, A., et al., 1995, *J. Chrom.*, 668:13-19; Huse, K. et al., 2002, *J. Biochem. Biophys. Meth.*, 51:217-231; McAtee, C. P. & Hornbuckle, J., 2012, *Curr. Prot. Protein Sci.*, Ch. 8:unit 8.10; for review see Marichal-Gallardo, P. A. & Alvarez, M. M., 2012, *Biotechnol. Prog.*, 28:899-916). Also, the kits for Ig purification are commercially available from many companies (e.g. GE HealthCare; Promega, Thermo Scientific, etc). A book on antibody purification is "Process Scale Purification of Antibodies", Uwe Gottschalk, ed., John Wiley & Sons, Hoboken, N. J., 2009.

In the present invention, the N-glycan occupancy of an N-glycosylation site of consensus sequence Asn-X-Ser or Asn-X-Thr (herein also abbreviated as "Asn-X-Ser/Thr"), X being any one of the twenty standard amino acid residues, of a recombinant glycoprotein may be adapted upon expression in plants or plant cells by placing certain amino acid residues at position +3 or −1 from the N-glycosylation site. The term "N-glycosylation site" refers to the asparagine residue present in the well-known consensus sequence "Asn-X-Ser/Thr" of N-linked glycosylation in proteins or polypeptides upon expression in eukaryotic cells. "Position +3" means the amino acid position in the polypeptide three residues in C-terminal direction from the N-glycosylation site, whereby the Asn residue of the N-glycosylation site is assigned position 0. "Position −1" means the amino acid position in the polypeptide one residue in N-terminal direction from the N-glycosylation site, wherein the Asn residue of the N-glycosylation site is assigned position 0.

The "glycan occupancy" or "glycosylation occupancy" of a selected N-glycosylation site refers to the fraction of molecules of the recombinant glycoprotein wherein the N-glycosylation site carries any glycan in a composition comprising a plurality of molecules of the recombinant glycoprotein. The type of glycan structure linked to the N-glycosylation site is not limited. If a given polypeptide has multiple N-glycosylation sites in its amino acid sequence, occupancies may be defined for each of these multiple N-glycosylation sites separately.

For achieving a high or increased N-glycan occupancy at a given N-glycosylation site, the amino acid residue at position +3 is any one of Thr, Ser, Gly, Leu, Ile, Val and Met. Thr, Ser and Gly are preferred among these residues, Thr and Ser are more preferred and Thr is most preferred. However, the residue at position +3 may be any of these residues.

For achieving a low or decreased N-glycan occupancy at a given N-glycosylation site, the amino acid residue at position −1 is any one of Glu and Asp. However, it is preferred to provide for high or increased N-glycan occupancy.

Increased N-glycan occupancy means that the N-glycan occupancy is higher in the glycoprotein expressed in a plant or plant cells if the amino acid residue at position +3 is as defined above compared to a glycoprotein having another amino acid residue at this position and expressed under otherwise the same conditions. Decreased N-glycan occupancy means that the N-glycan occupancy is lower in the glycoprotein expressed in a plant or plant cells if the amino acid residue at position −1 is as defined above compared to a polypeptide having another amino acid residue at this position and expressed under otherwise the same conditions.

N-glycan occupancy may be determined experimentally, e.g. using capillary gel electrophoresis as done in the Examples. Frequently, a qualitative analysis of increased or lowered N-glycan occupancy may be sufficient. The recombinant glycoprotein of item (a) may have a glycosylation occupancy at an N-glycosylation site of at least 85%, more preferably at least 90%, and even more preferably of at least 95%. The recombinant glycoprotein of item (b) may have a glycosylation occupancy at said N-glycosylation site of at most 65%, preferably at most 55%.

In case of multiple N-glycosylation sites in a polypeptide, all or some may be manipulated for high or low N-glycan occupancy, or they may be manipulated differently.

The invention also provides a process of producing a recombinant glycoprotein in a plant, in cells of a plant, or in plant cells, which involves genetic engineering for obtaining the desired amino acid residues at position +3 and/or −1. The process may comprise providing a nucleic acid encoding a polypeptide having an N-glycosylation site of consensus sequence Asn-X-Ser or Asn-X-Thr, X being any standard amino acid residue, engineering the nucleic acid such that, if the Asn residue of said N-glycosylation site is assigned amino acid sequence position 0, the amino acid residue at position +3 and/or −1 is as defined in item (a) or (b) defined herein, and expressing in a plant, in cells of a plant or in plant cells the engineered nucleic acid, thereby producing the recombinant glycoprotein.

The recombinant glycoprotein may be a monomeric glycoprotein or an oligomeric glycoprotein. Formation of the recombinant glycoprotein involves expression of at least one polypeptide of the invention in a plant, cells of the plant, or plant cells, N-glycosylation, folding and optionally further post-transcriptional modifications or processes such as targeting to a particular cell compartment or to the apoplast. This does, however, not exclude the possibility that a recombinant glycoprotein according to the invention is obtained by other means or methods. If the recombinant glycoprotein is oligomeric, it may be homooligomeric or heterooligomeric. In the case of a heterooligomeric recombinant glycoprotein, only one or multiple subunits may have an N-glycosylation site and may be N-glycosylated. Accordingly, only one of multiple subunits may have a modified N-glycosylation site as defined herein. The multiple subunits of a heterooligomeric protein may be co-expressed in a plant or in plant cells, e.g. as described in WO002006079546. Preferred heterooligomeric proteins are immunoglobulins, notably antibodies of the immunoglobulin G type, as further described in the following.

Figure 13A:
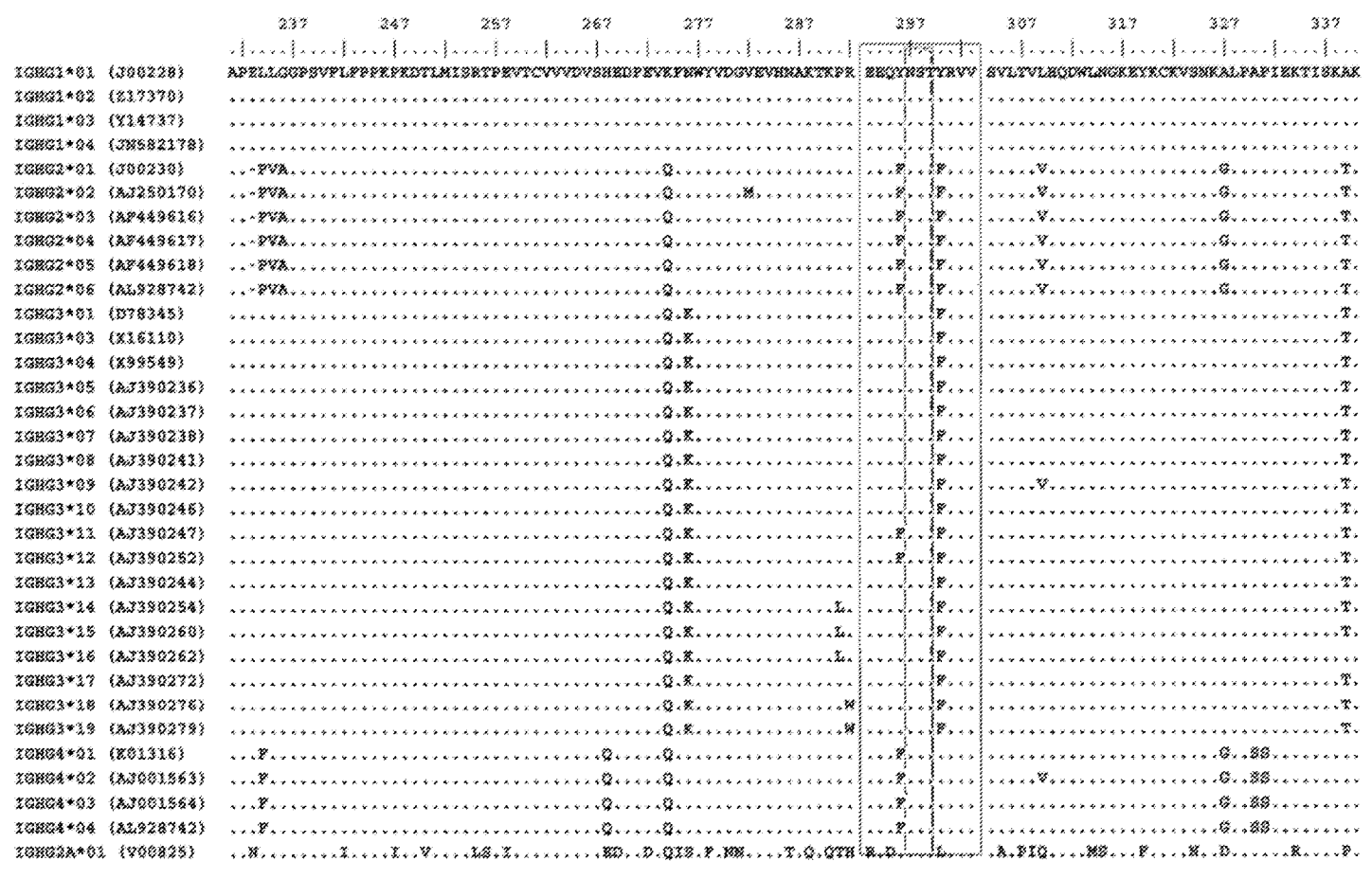
Figure 13:
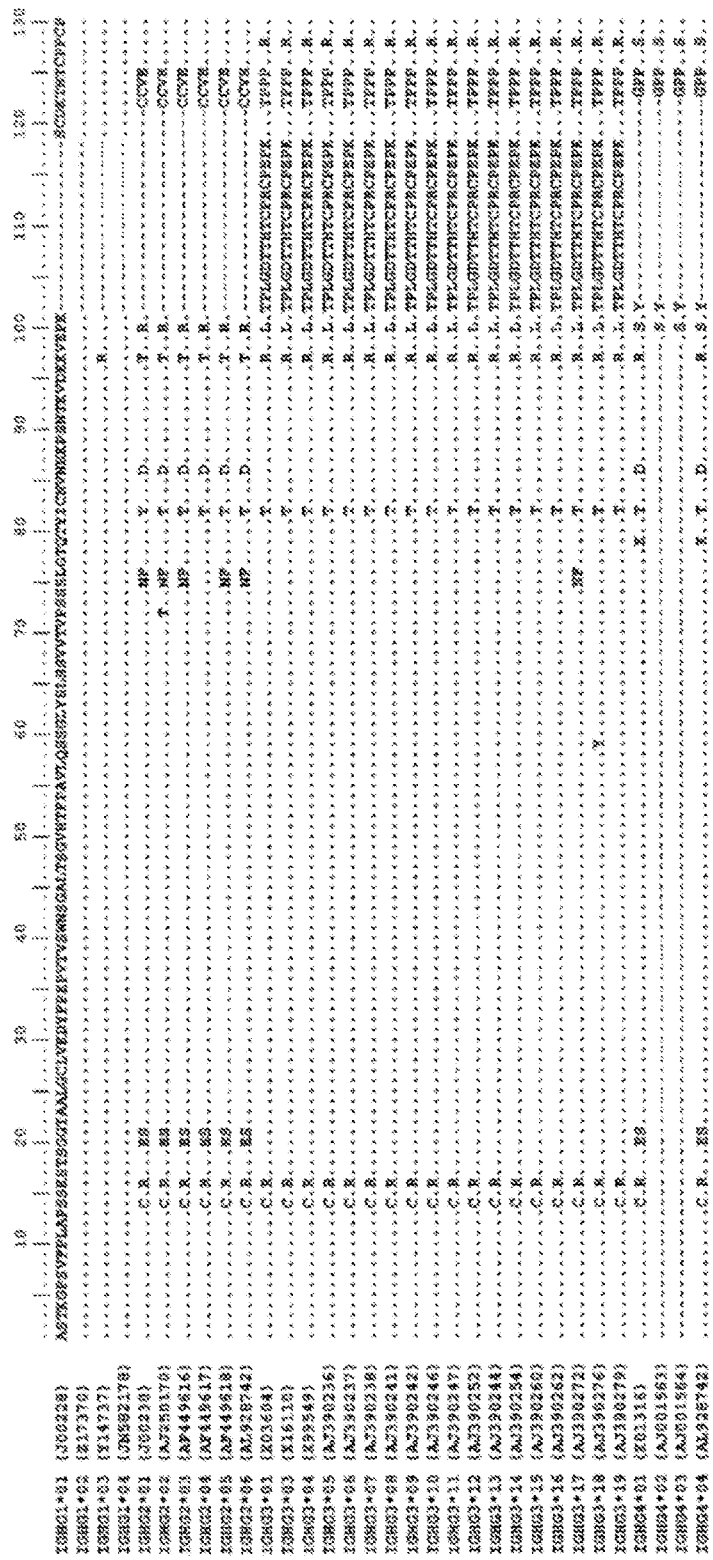
FIG. 13: A. Alignment of the CH2 regions of different human IgG subclasses. A sequence segment containing the N-glycosylation site is boxed. The N-glycosylation site Asn-X-Ser/Thr is indicated by a grey background. The amino acid residue positions are numbered according to the EU index as in Kabat (Kabat, E. A. et al., 1991, Sequences of Proteins of Immunological Interest, DHHS, Washington, D.C., 5$^{th}$ edition). The top row of IgHG1*01 is SEQ ID NO: 19. The sequences of the subsequent rows are SEQ ID NOs 23 to 54, respectively. The bottom row shows the CH2 region of mouse IgG2 subclass, allele A. B. Alignment of heavy chain constant regions of different IgG subclasses. The top row of IgHG1*01 is SEQ ID NO: 20. The sequences of the subsequent rows are SEQ ID NOs 55 to 85, respectively.

The recombinant glycoprotein of the invention may be an immunoglobulin G (IgG) or comprises an IgG heavy chain. A typical IgG antibody is composed of two light and two heavy chains that are associated with each other to form three major domains connected through a flexible hinge region: the two identical antigen binding regions also present in the Fab fragment, and the constant region of the heavy chains that can form the Fc fragment. The IgG Fc region is a homodimer in which the two CH1 domains are paired through non-covalent interactions. The two hinge region heavy chains between CH1 and CH2 are paired through covalent bonding. The two CH2 domains are not paired but each has a conserved N-glycosylation site at Asn-297. There are several subclasses of IgG—IgG1, IgG2, IgG3 and IgG4, and the recombinant glycoprotein of the invention may belong to any one of these subclasses. An alignment of CH2 domains of said subclasses is shown in FIG. 13A, and an alignment of heavy chain constant regions is shown in FIG. 13B.

In one embodiment of the processes of the invention and the recombinant glycoprotein of the invention, the polypeptide comprises an IgG heavy chain constant segment CH2 and has the amino acid residues at positions +3 or −1 at an N-glycosylation site as defined above. Examples of heavy chain constant regions are given in FIG. 13A any of which may be used. However, preferably, a human-derived IgG heavy chain constant segment CH2 is used as shown in the sequences segments of the 32 amino acid sequence segments shown in the top portion of FIG. 13A (the bottom sequence is from mouse). Possible alternatives of the human CH2 regions of FIG. 13A are CH2 regions that have from 1 to 15, preferably from 1 to 10 amino acid substitutions from the CH2 regions shown at the top of FIG. 13A (SEQ ID NO: 19). Other possible alternatives are CH2 regions that have an amino acid sequence identity of at least 93%, preferably of at least 95%, more preferably of at least 97% to the amino acid sequence of SEQ ID NO: 19. Further possible alternatives are CH2 regions that have an amino acid sequence similarity of at least 95%, preferably of at least 97%, more preferably of at least 99% to the amino acid sequence of SEQ ID NO: 19. Sequence identities may be calculated with AlignX, a component of Vector NTI Suite 7.1, InforMax Inc. using standard settings (K-tuple size: 2; number of best diagonals: 4; window size 4; gap penalty 5; gap opening penalty 15; gap extension penalty 6.66). Amino acid sequence similarities may be determined using BLASTX 2.2.14 using the standard settings.

In one embodiment of the processes of the invention and the recombinant glycoprotein of the invention, the polypeptide comprises an IgG heavy chain constant region and has the amino acid residues at positions +3 or −1 at the N-glycosylation site as defined above. Examples of human heavy chain constant regions are given in FIG. 13B any of which may be used. The sequence portion at the top of FIG. 13B is SEQ ID NO: 20. Possible alternatives of the heavy chain constant regions of SEQ ID NO: 20 or of the IGHG3*01 sequence shown in FIG. 13B are constant regions that have from 1 to 20, preferably from 1 to 15, more preferably from 1 to 10 amino acid substitutions or additions from the constant regions shown at the top of FIG. 13B or of the IGHG3*01 sequence shown in FIG. 13B. Other possible alternatives are constant regions that have an amino acid sequence identity of at least 90%, preferably of at least 93%, more preferably of at least 96% to the amino acid sequence of SEQ ID NO: 20 or of the IGHG3*01 sequence shown in FIG. 13B. Further possible alternatives are constant regions that have an amino acid sequence similarity, or identity, of at least 92%, preferably of at least 95%, more preferably of at least 98% to the amino acid sequence of SEQ ID NO: 20 or of the IGHG3*01 sequence shown in FIG. 13B.

Figure 5:
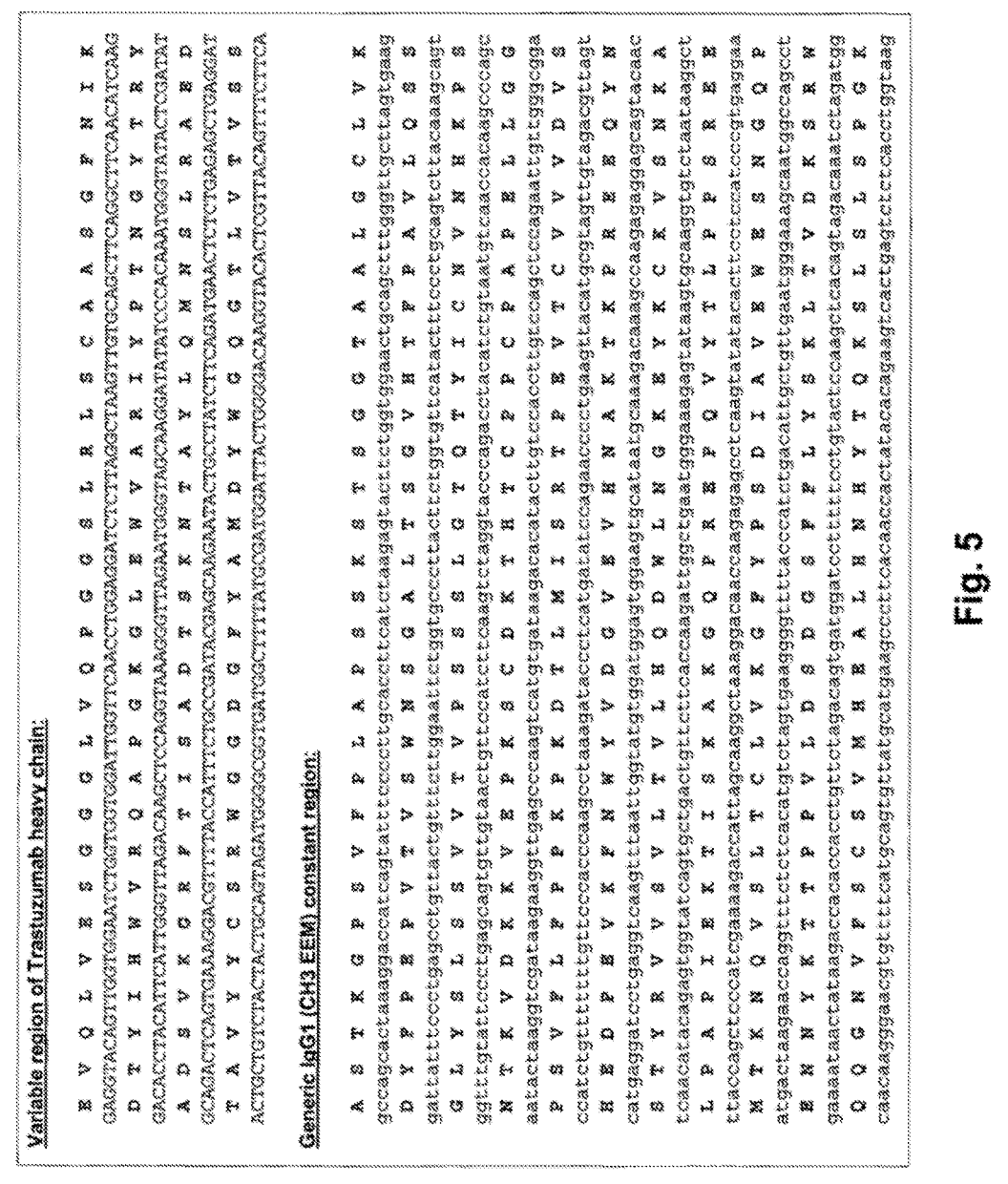
Figure 7:
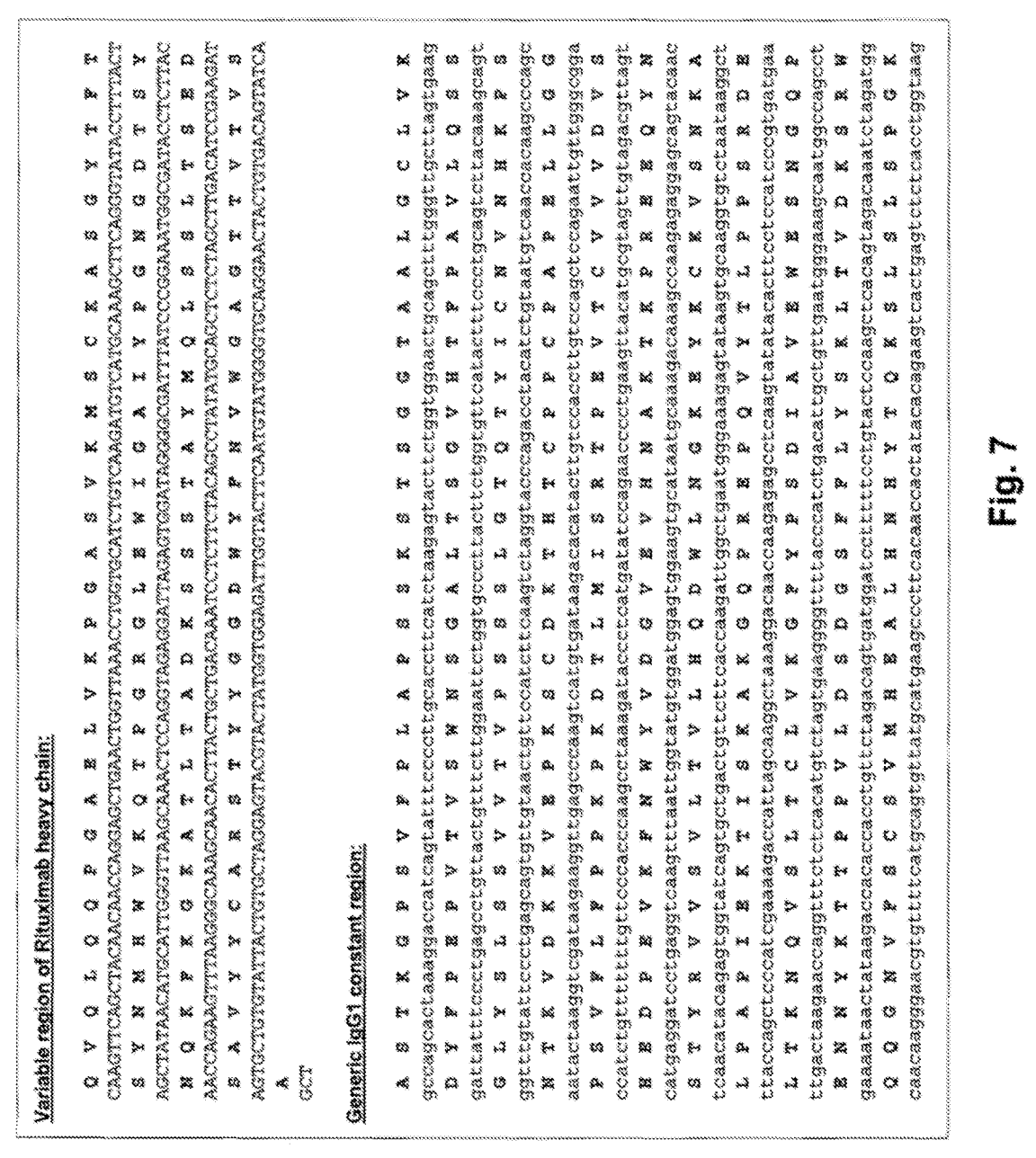

In another embodiment, the polypeptide comprises an IgG heavy chain constant region (including constant segments CH1, CH2 and CH3) and has the amino acid residues at positions +3 or −1 at an N-glycosylation site as defined above. In another embodiment, the polypeptide comprises an IgG heavy chain including variable and constant regions and has the amino acid residues at positions +3 or −1 at an N-glycosylation site as defined above. If the recombinant glycoprotein is or comprises an IgG heavy chain, there are no particular limitations with regard to the amino acid sequence of the variable region of the heavy chain, notably with regard to the complementarity determining regions (CDRs). Preferred IgGs have the binding affinities conferred by their variable regions of the antibodies used in the Examples. Thus, a preferred IgG has a heavy chain with variable and constant regions as shown in FIG. 5 and light chains as shown in FIG. 4. Another preferred IgG has a heavy chain with variable and constant regions as shown in FIG. 7 and light chains as shown in FIG. 6.

In the case of IgGs, the heavy chain constant region has one N-glycosylation site the N-glycan occupancy of which may be modified according to the invention. This N-glycosylation site is at position 297 in the Kabat sequence numbering mentioned above and indicated in FIG. 1A.

The recombinant glycoprotein may comprise a heavy chain constant region having an amino acid sequence of that of a human IgG, except for the amino acid at the N-glycosylation site at position +3 as defined herein.

In one embodiment, the present invention provides recombinant glycoproteins that are IgGs, and pharmaceutical or other compositions comprising such IgGs, wherein the IgG has variable regions of both heavy and light chains identical to any one of the following known antibodies: ibritumomab tiuxetan, adalimumab, cetuximab, rituximab, basiliximab, palivizumab, infliximab, trastuzumab, gemtuzumab ozogamicin, alemtuzumab, omalizumab, tositumomab, 1-131 tositumomab, efalizumab, bevacizumab, panitumumab, pertuzumab, natalizumab, etanercept, IGN101 (Aphton), muromonab-CD3, abciximab, daclizumab, volociximab (Biogen Idec and PDL BioPharm), CP-675,206 (Pfizer), CAL (Roche), Anti-CD80 mAb (Biogen Idec), Anti-CD23 mAb (Biogen Idel), stamulumab, CAT-3888 (Cambridge Antibody Technology), CDP791 (Imclone), eraptuzumab (Immunomedics), MDX-010 (Medarex and BMS), MDX-060 (Medarex), nimotuzumab, MDX-070 (Medarex), matuzumab (Merck), brentuximab, zanolimumab, adecatumumab, oregovomab, briakinumab, denosumab, AMG 108, genmab, fontolizumab, daclizumab, ustekinumab, ocrelizumab, HuMax-CD20, belimumab, epratuzumab, MLN1202, visilizumab, tocilizumab, ocrerlizumab, certolizumab pegol, eculizumab, pexelizumab, abciximab, ranibizimumab, mepolizumab, ibalizumab or golimumab.

Such antibodies may further have constant regions of both light and heavy chains as in these known antibodies, except for the modification at position +3 of the N-glycosylation site in the heavy chain constant regions. Isolated nucleic acids encoding these heavy chains, nucleic acid constructs comprising the nucleic acids, vectors comprising the constructs, and plants comprising the constructs are also provided.

Purified IgGs and their CH2 mutant variants were analyzed for glycosylation site occupancy using capillary gel electrophoresis (CGE). Separation of glycosylated and aglycosylated heavy chains is possible due to the difference in molecular mass caused by glycan attachment (ca. 2-5 kDa). Electropherograms of CGE analyses of rituximab, trastuzumab and their different mutant variants are shown on FIGS. 8-12. The ratio between glycosylated and aglycosylated HC can be reasonably well measured using the corresponding peak area from electropherogram. More precise measurements are obtained for larger peaks, so optimal loading of the IgG on the gel is required. Insufficient loading of the Ig from small (e.g. 1 g batches) leads to less precise measurement. However, despite that, all data obtained and summarized in the Tables 1 and 2 convincingly demonstrate the effect of different amino acid residue substitutions on glycosylation site occupancy. It is evident that replacement of tyrosine residue to phenylalanine at position 296 is neutral, as it does not have a noticeable effect on glycosylation site occupancy, while replacement to glutamic acid at the same position leads to significant decrease in the occupancy of said site. On the contrary, replacement of tyrosine at position 300 to threonine or glycine significantly increases the glycosylation level of Fc. Taking into consideration that replacement of tyrosine by phenylalanine at position 296 has no effect on glycosylation occupancy, our finding for Fc of IgG1 can be expanded to other subclasses of IgG, where phenylalanine replaces tyrosine at positions 296 and/or 300 (IgG2, IgG3, IgG4, see FIG. 13A). Interestingly, the Fc glycosylation site of anti-CD20 IgG2A antibody is more than 98% occupied (FIG. 12B). The sequence fragment of mouse IgG2a flanking N-glycosylation site is identical to the one of human IgG1, except for a single amino acid substitution of leucine in mouse IgG2a for the second tyrosine in the sequence fragment YNSTYRVV (amino acids 179 to 189 of SEQ ID NO: 1) of human IgG1. We cannot exclude the influence of other sequence positions on the N-glycosylation site occupancy of the Fc region, including the sequences of IgG variable region. However, it is evident that the strongest effect on the N-glycosylation level does have the neighboring amino acid residues, especially at the position 300. This means that replacement Y300L shall have positive effect on glycosylation site occupancy of the Fc region.

In one embodiment, the recombinant glycoprotein is not an outer surface protein A (OspA) from a *Borrelia* species such as *Borrelia burgdorferi* or a protein having an amino acid sequence identity of more than 95, preferably more than 90 and even more preferably more than 80%, to the amino acid sequence of FIG. 1 of WO 2009/126816.

We have found that co-expression of plant-made trastuzumab and rituximab together with the gene encoding *Leishmania major* STT3D (LmSTT3D) protein (FIGS. 1B and 2B) greatly increases the N-glycosylation sites occupancy even without the need for introducing a mutation at position +3 of the N-glycosylation site. The gene encoding the STT3D protein is preferably plant-codon optimized. The data shown in FIG. 12C demonstrate that glycosylation site occupancy is similar or even slightly better than for Y300T or Y300G mutants (see FIGS. 9 and 10). Co-expression of STT3D with mutant versions of rituximab and trastuzumab (Y300T or Y300G, data not shown) shows a glycosylation level indistinguishable from the commercially available products produced in animal cell expression systems. The usefulness of such approach was shown in a yeast expression system, e.g. *Pichia pastoris* (Choi, B K. et al., 2012, *Appl. Microbiol. Biotechnol.,* 95:671-682; US20120328626).

The invention also provides a process of producing a recombinant glycoprotein in a plant, in cells of a plant, or in plant cells, comprising expressing in said plant, in cells of said plant or in plant cells a nucleic acid sequence encoding a polypeptide having an N-glycosylation site and co-expressing a second nucleic acid sequence encoding a heterologous single-subunit oligosaccharyltransferase (OTase). The polypeptide having an N-glycosylation site may be the polypeptide described above having certain amino acid residues at position +3, or another polypeptide having an N-glycosylation site. The second nucleic acid sequence that encodes a heterologous single-subunit oligosaccharyltransferase may be expressed as described above for the nucleic acid sequence of interest (first nucleic acid sequence). Both expression from a viral vector or from a non-viral vector is possible. The second nucleic acid sequence may be expressed from the same vector as the first one. In this case, T-DNA of a binary vector may contain two expression cassettes, one for the first and one for the second nucleic acid sequence. In one embodiment, the first and the second nucleic acid sequence are both contained in the nucleic acid construct described above.

In a further embodiment, a transgenic plant line may be produced that contains the second nucleic acid sequence and expresses it e.g. under the control of a constitutive or regulated promoter. Such transgenic plant or cells thereof may then be used for expressing the glycoprotein of the invention as described above, e.g. transiently using *Agrobacterium*-mediated transfection.

Alternatively, the first and the second nucleic acid sequence may be expressed from separate vectors. In this case, both nucleic acid sequences may be transfected or transformed into plant cells as part of T-DNA using *Agrobacterium*-mediated transfection or transformation. Co-transformation may be easily performed by mixing two *Agrobacterium* populations or strains, one containing a binary vector containing, in T-DNA, the first nucleic acid sequence and one containing a binary vector containing, in T-DNA, the second nucleic acid sequence. The mixture may then be used for transfection, e.g. by infiltration or spraying, as described above. It is not necessary that both vectors are either viral or non-viral vectors. For example, it is possible that the first nucleic acid sequence is expressed from a viral vector, while the second nucleic acid sequence is expressed from a non-viral vector. The mixing ratios of the *Agrobacterium* populations or strains may be suitably adjusted as the case requires. For example, if only one of the nucleic acid sequences is expressed from a viral vector, the *Agrobacterium* containing the non-viral vector may be used in higher concentration than the *Agrobacterium* containing the viral vector.

In a preferred embodiment, a process of producing a recombinant glycoprotein in a plant is provided, comprising transfecting the plant with a first *Agrobacterium* containing a first DNA molecule comprising a T-DNA comprising a nucleic acid construct containing a DNA sequence of interest encoding a polypeptide having an N-glycosylation site, and transfecting the plant with a second *Agrobacterium* containing a second DNA molecule comprising a T-DNA comprising a nucleic acid construct containing a second DNA sequence encoding a heterologous single-subunit oligosaccharyltransferase; and expressing the first and the second DNA sequence to produce a glycosylated form of said polypeptide as said glycoprotein. If a heterodimeric or heterooligomeric protein is to be produced, two nucleic acid sequences of interest may be expressed together with the second DNA sequence encoding the heterologous single-subunit oligosaccharyltransferase.

Regarding the *Agrobacterium* that may be used for transfecting the first and the second DNA sequence, the information given above applies. Notably, the T-DNAs may be flanked on both sides by T-DNA border sequences. Either one or both of the DNA molecules may contain a selectable marker outside of said T-DNA for allowing cloning and genetic engineering in bacteria. However, the T-DNAs that are transferred into cells of said plant preferably do not contain a selectable marker that would, if present, allow selection of plant or plant cells containing said T-DNA. The process does preferably not comprise a step of selecting for plant cells having incorporated the first nor the second DNA sequence using an antibiotic resistance gene or a herbicide resistance gene. Accordingly, no antibiotic resistance gene or a herbicide resistance gene needs to be incorporated into said plant.

The second nucleic acid sequence encodes a single-subunit oligosaccharyl-transferase that is heterologous to the plant (or cells) used for expressing it. The oligosaccharyl-transferase (or "OST") belongs to class EC 2.4.1.119. It is a membrane protein complex that transfers a 14-sugar oligosaccharide from dolichol to a nascent protein in eukaryotic cells. It is a type of glycosyltransferase. The sugar Glc3Man9GlcNAc2 (where Glc=Glucose, Man=Mannose, and GlcNAc=N-acetylglucosamine) is attached to an asparagine (Asn) residue in the consensus sequence Asn-X-Ser or Asn-X-Thr, where X is any amino acid except proline. This consensus sequence is called a glycosylation sequon. The reaction catalyzed by OST is the central step in the glycosylation pathway of N-linked glycoproteins.

Figure 14:
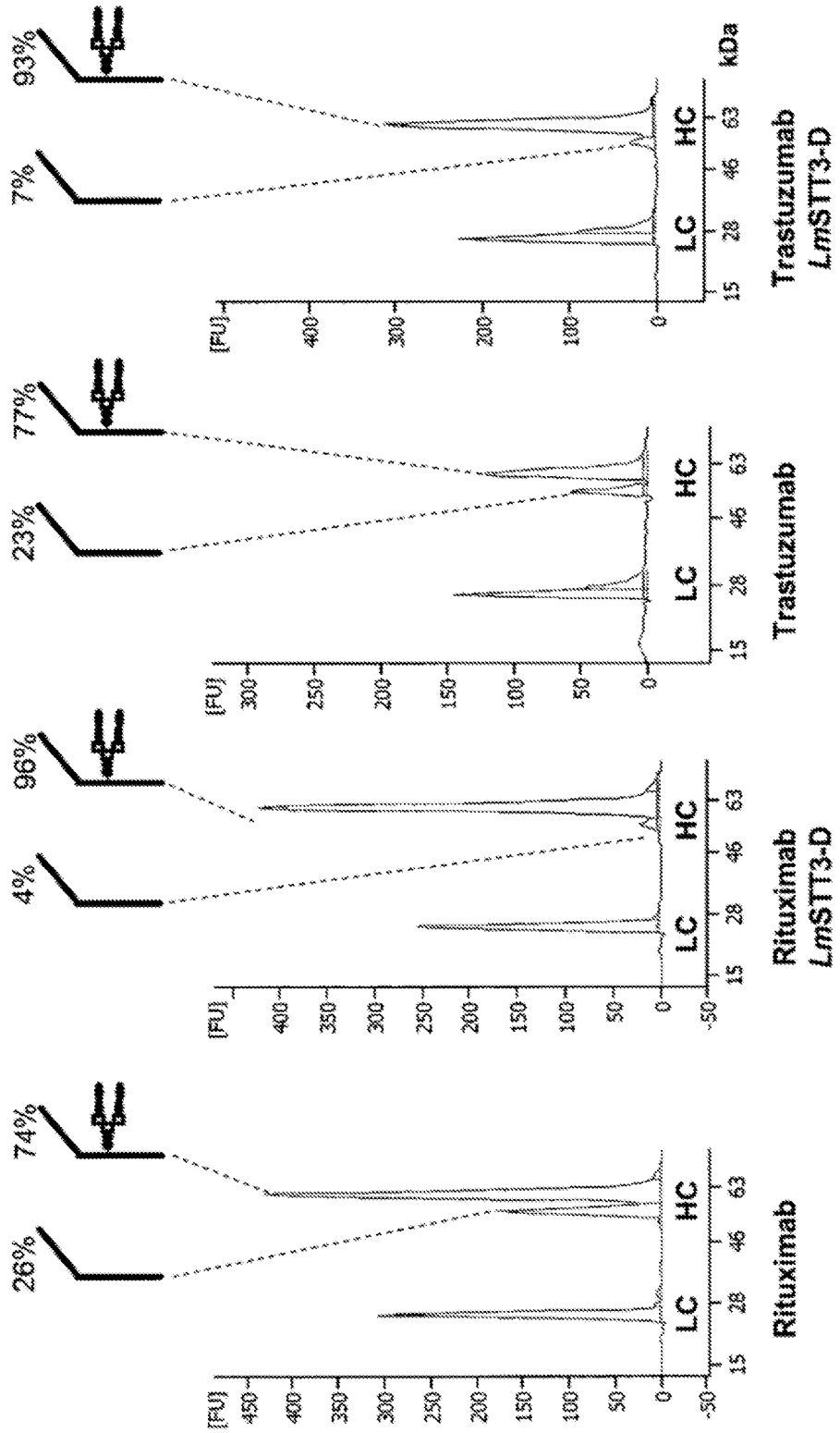
FIG. 14: A. Electropherograms of capillary gel electrophoretic (CGE) analysis at reducing conditions of plant-produced rituximab and trastuzumab without and with co-expression of Leishmania major oligosacharyltransferase LmSTT3-D. HC—heavy chain; LC—light chain. Percentages of aglycosylated and glycosylated variants of HC are shown at the top of corresponding peaks of the electropherogram. B. Electropherograms of capillary gel electrophoretic (CGE) analysis at reducing conditions of plant-produced palivizumab and anti-ebola mAb without and with co-expression of Leishmania major oligosacharyltransferase LmSTT3-D. HC—heavy chain; LC—light chain. Percentages of aglycosylated and glycosylated variants of HC are shown at the top of corresponding peaks of the electropherogram.
Figure 14B:
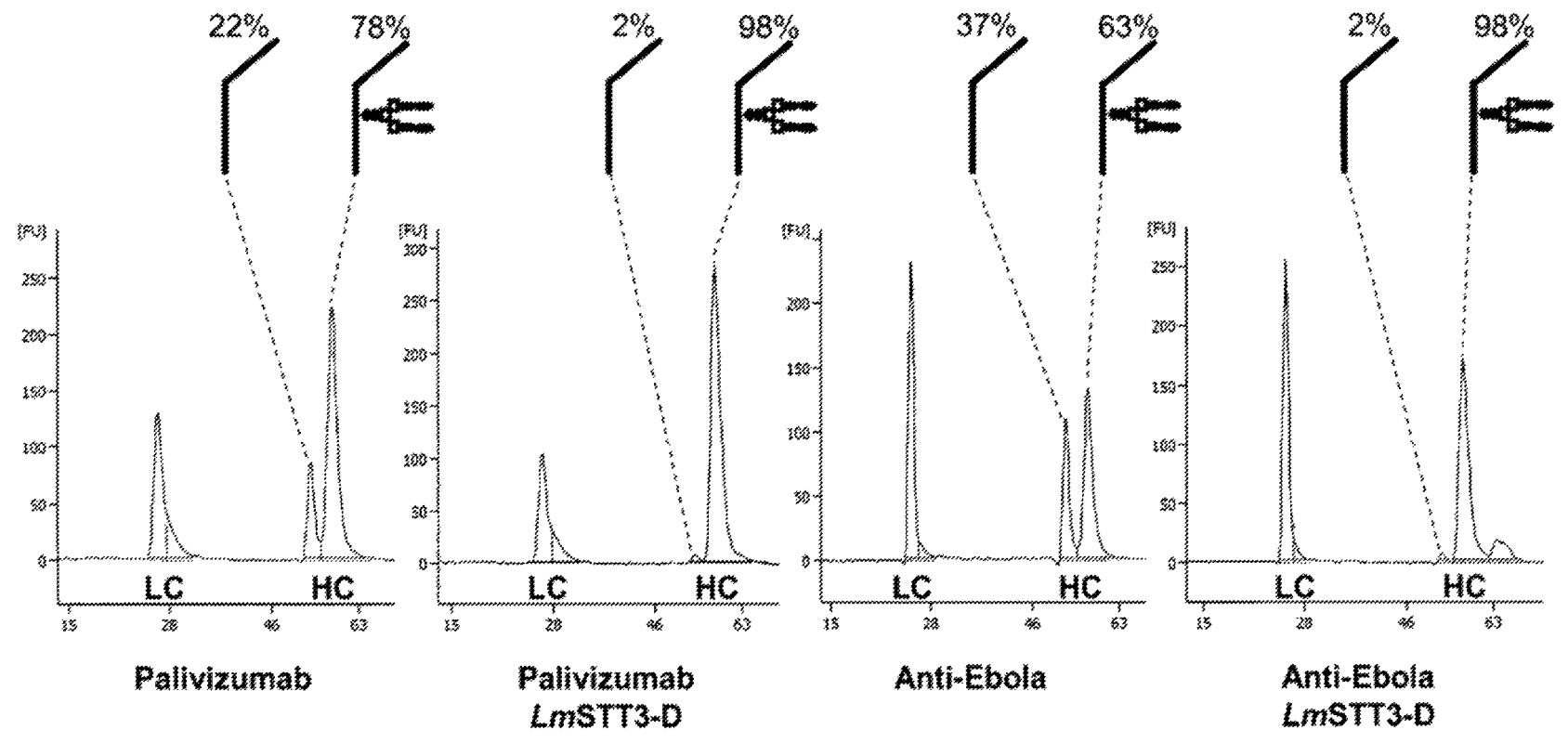

The single-subunit oligosaccharyltransferase may be a *Leishmania* protein such as STT3-A, STT3-B, STT3-C or STT3-D, or combinations thereof. A preferred origin for these proteins is *Leishmania major*. The preferred protein is *Leishmania major* STT3D (LmSTT3D). Sequences of these proteins and coding sequences thereof are known from US 2012/0328626. The amino acid sequence of a His-tagged variant of LmSTT3-D that was expressed in the experiments the results of which are reported in FIGS. 12C and 14 is given as SEQ ID NO: 2 in FIG. 1B. The amino acid sequence of wild-type LmSTT3-D is given in FIG. 2D (SEQ ID NO: 22).

The invention is not limited to any of the Lm STT3 proteins listed above and nucleic acid sequences encoding them. Alternatively, the following nucleic acid sequences may be used as the second nucleic acid sequences:
  a nucleic acid sequence encoding a protein having an amino acid sequence having at least 80%, preferably at least 90%, sequence identity to the entire amino acid sequence of any one of SEQ ID NO: 2; or
  a nucleic acid sequence encoding a protein having an amino acid sequence having at least 90%, preferably at least 95%, sequence similarity to the entire amino acid sequence of any one of SEQ ID NO: 2; or
  a nucleic acid sequence encoding a protein having an amino acid sequence of a length of at least 80%, preferably at least 90%, more preferably at least 95% of the number of amino acid residues of any one of SEQ ID NO: 2, and a sequence identity of at least 90% to SEQ ID NO: 2 over such length; or
  a nucleic acid sequence encoding a protein having an amino acid sequence having from 1 to 30 amino acid additions, substitutions or deletions compared to the amino acid sequence of any one of SEQ ID NO: 2. The maximum number of amino acid additions, substitutions or deletions may be at most 20, preferably at most 15, more preferably at most 10, and even more preferably at most 5, whereby the total number of additions, substitutions and additions together determine the number of "amino acid additions, substitutions or deletions".

Sequence identities and similarities may be determined as mentioned above.

Preferably, the variants of LmSTT3-D have a similar or, preferably, the same efficiency of increasing the N-glycosylation site occupancy as LmSTT3-D, which may be tested experimentally as described in the Examples. The plant cells used for expressing the OTase preferably have their native OTase complex.

The pharmaceutical composition of the invention contains the recombinant glycoprotein of the invention, which is preferably an IgG antibody. The pharmaceutical composition may be an aqueous liquid composition or a solid composition. The solid composition may be prepared from the aqueous liquid composition by freeze-drying (lyophilisation). The lyophilised solid composition may be reconstituted to form a liquid aqueous composition by adding water or an aqueous solvent. The aqueous liquid composition may be a composition that includes, in addition to the glycoprotein, buffer and water. The composition may further contain pharmaceutical excipients such as an isotonizing agent, a preservative or others (see further below).

In the aqueous composition, the glycoprotein may be present in a concentration of from about 0.1 to about 10 mg/ml, preferably in an amount of from about 0.5 to about 5 mg/ml and more preferably of about 0.7 to 2.5 mg/ml.

The buffer concentration in the aqueous composition may be 5 mM to 100 mM, preferably 10 mM to 50 mM, and in one embodiment 20 mM to 30 mM. Examples of buffer substances are organic acids and bases such as citric acid, maleic acid, fumaric acid, acetic acid, histidine, imidazole, Tris, HEPES, or inorganic buffers such as phosphate or diphosphate. Histidine is a preferred buffer substance. Regarding the pH of the aqueous composition, a pH which is close to the physiological pH of humans should be chosen when used for administration to patients. The pH may be between 7.0 and 7.8. In one embodiment it is between 7.2 and 7.6 and more preferably 7.3 to 7.5. The pH may be set as commonly known by adding an acid to an aqueous histidine solution. Examples of the acid are inorganic acids such as hydrochloric acid and sulfuric acid, or organic acids such as citric acid, lactic acid, tartaric acid and other physiologically acceptable acids.

The pharmaceutical composition may optionally further contain a nonionic surfactant. Examples of surfactants are known to the skilled person e.g. from McCutcheon's Emulsifiers and Detergents, 1986 North American Edition, McCutcheon Division Publishing Co., Glen Rock, N.J. For medical applications such as for the formulation of the invention, pharmaceutically acceptable nonionic surfactants can be used as known by the skilled person. Combinations of nonionic surfactants can also be used in the present invention.

Among nonionic surfactants, polysorbate surfactants are particularly preferable. Polysorbate surfactants are understood herein to comprise polyoxyethylene sorbitan fatty acid esters, such as polysorbate 80 (poly(oxyethylene)sorbitan monooleate, also known as Tween-80), polysorbate 60 (poly(oxyethylene)sorbitan monostearate, also known as Tween-60), polysorbate 40 (poly(oxyethylene)sorbitan monopalmitate, also known as Tween-40), polysorbate 20 (poly(oxyethylene)sorbitan monolaurate, also known as Tween-20), polysorbate 85 (poly(oxyethylene)sorbitan trioleate, also known as Tween-85) and polysorbate 65 (poly(oxyethylene)sorbitan tristearate, also known as Tween-65). Of these, polysorbate 20 and polysorbate 80 are preferred, with polysorbate 80 being particularly preferred.

Other nonionic surfactants usable in the invention are poly(propylenoxide) and block copolymers of poly(propylenoxide) and poly(ethylenoxide) such as Synperonic® F-68, Pluronic® F68, Lutrol® F68 or Poloxamer 188.

Further additives for the composition of the invention that may be used instead of the nonionic surfactants are cyclodextrins, such as HP-β-CD, that may be used for protein stabilisation and can be used for parenteral administration of drugs.

The non-ionic surfactant may be present in the aqueous composition or the aqueous liquid preparation in a concentration of from about 0.001% to about 2% (w/v), preferably from about 0.01% to about 0.5% (w/v). In a preferred embodiment, the surfactant is present in a concentration of about 0.1% (w/v), in an alternative preferred embodiment in a concentration of about 0.01%(w/v).

The pharmaceutical composition may comprise an isotonization agent. For the parenteral administration of a pharmaceutical composition, it is desirable to adjust the tonicity of the formulation to the fluids of the human body. The isotonization agents to be used will be apparent to a person skilled in the art. However, sugar alcohols, polyvinyl pyrrolidone and disaccharides are explicitly mentioned. Of these, mannitol and disaccharides are preferred with disaccharides being more preferred. Particularly preferred disaccharides comprise trehalose and sucrose.

The pharmaceutical composition may further contain one or more additional pharmaceutically acceptable excipients such as buffers, anti-oxidants, bacteriostatic agents, diluents, carriers, surfactants, salts, preserving, stabilizing, wetting or solubilizing agents, and/or excipients for regulating the osmolarity.

Generally, a pharmaceutical composition herein means a composition which is suitable for administration to patients, notably of human patients. The pharmaceutical composition may be administered to the patient by way of parenteral administration, preferably by subcutaneous or intramuscular administration, more preferably by way of subcutaneous administration.

The pharmaceutical composition or the glycoprotein of the invention may be used in a method of therapy. Preferably, it is used for the treatment of cancer. Examples of the cancers are Her2/Neu positive cancers such as those mentioned in the following.

Human Epidermal Growth Factor Receptor Her2, also known as Neu, ErbB-2, or p185, is a member of the epidermal growth factor receptor (EGFR/ErbB) family and encoded by the ERBB2 gene. As other members of ErbB family, Her2 is a membrane-bound receptor tyrosine kinases composed of extracellular ligand binding domain, a transmembrane domain, and an intracellular domain that can interact with downstream signaling molecules. Amplification of the ERBB2 gene occurs in 20-30% of human breast and ovarian cancers and is linked to a more aggressive disease course and worse prognosis (Bange, J., Zwick E. & Ullrich A., 2001, *Nature Medicine*, 7: 548-552; Slamon, D. J., Clark, G. M., Wong, S. G. et al., 1987' *Science*, 235: 177-182; Slamon, D. J., Godolphin, W., Jones, L. A. et al., 1989, *Science*, 244:707-712; Berchuck, A., Kamel, A., Whitaker. R., et al., 1990, *Cancer Research* 50:4087-4091). In ERBB2$^+$ tumor cells, the receptor can function on its own and/or it needs to heterodimerize with another ErbB member to transduce a deregulated proliferative signal responsible for the neoplastic behavior of the cells. HER2 has evolved as an important target for therapy of breast cancer in particular by monoclonal antibody therapy, e.g. Herceptin (trastuzumab) a humanized monoclonal antibody against this surface target has been approved by FDA in 1998. Herceptin has a significant impact on survival rates of HER2 positive breast cancer patients (Tan, A. R. & Swain, S. M., 2002, *Seminars in Oncology*, 30: 54-64). Although active against HER2 homodimers, trastuzumab is not effective against ligand-induced HER2 heterodimers (Agus, D. B., Akita, R. W, Fox, W. D., et al., 2002; *Cancer Cell*, 2:127-137; Cho, H. S., Mason, K., Ramyar, K. X, et al., 2003, *Nature*, 421:756-60). Trastuzumab is efficient for the treatment of late stage metastatic cancers. U.S. Pat. No. 7,449,184 and U.S. Pat. No. 7,981,418 describe antibody therapies of HER2/neu positive metastatic breast cancer.

For the treatment of Her2/Neu positive cancers, the glycoprotein employed may have affinity to Her2/Neu. Preferably, for this purpose the glycoprotein is an antibody that has affinity to HER2/Neu such as an antibody having the variable domains of the heavy and light chains of trastuzumab.

EXAMPLES

In the following, the invention is further illustrated using examples. The invention is, however, not limited to these examples.

Example 1

Construct Design

Based on the MagnICON® technology (Gleba, Y., Klimyuk, V. & Marillonnet, S., 2005, *Vaccine* 23:2042-2048; Gleba, Y., Klimyuk, V. & Marillonnet, S. 2007, *Curr. Opin. Biotechnol.* 18:134-141) binary vectors were developed by Icon Genetics using elements from Tobacco Mosaic Virus (TMV) or Potato Virus X (PVX) (Giritch et al., 2006, *Proc. Natl. Acad. Sci. USA*, 103:14701-14706).

TMV vectors were built based on the cDNAs of two closely related plant viruses, TVCV (turnip vein clearing virus, Lartey, R. T., Lane, L. C. & Melcher, U., 1994, Arch. Virol., 138:287-298; Lartey, R. T., Voss, T. C. & Melcher, U., 1995, *Gene*, 166:331-332) and crTMV (a crucifer-infecting tobamovirus, Dorokhov, Y. L., Ivanov, P. A., Novikov, V. K., et al., 1994, FEBS Lett., 350:5-8) which naturally infect solanaceous and cruciferous plants by mechanical transmission. We call the resulting vector 'TMV-based', since both parental viruses are tobamoviruses and related to the well-known tobacco mosaic virus (TMV). All three viruses (TVCV, crTMV and TMV) are positive-strand RNA viruses and have the same overall structure and mode of replication. Basically, these viruses encode the following proteins: (1) a RNA-dependent RNA polymerase (RdRp), whose function is to replicate the full viral RNA transcript (the genomic RNA) as well as the two subgenomic RNAs (sgRNAs) that are required for expression of the two other viral proteins (the movement protein and the coat protein), (2) the Movement Protein (MP), which is required for cell-to-cell movement of the viral genomic RNA (short distance movement limited to within the infiltrated leaf), and (3) the Coat Protein (CP), which is required for formation of viral particles and systemic movement (long distance movement from leaf to leaf via the vascular system). Interestingly, formation of a viral particle is not required for cell-to-cell movement. Therefore, we have eliminated the coat protein from our vectors, and replaced it with the gene of interest. This has two consequences: the viral vector is unable to make viral particles, and the gene of interest is expressed at higher level than in the case where viral vectors contain both the CP and the gene of interest. In addition to the viral proteins and the gene of interest, the viral vector should also contain the 5' and 3' non-translated (5' ntr and 3' ntr) viral sequences (Marillonnet, S., Giritch, A., Gils, M. et al., 2004, *Proc. Natl. Acad. Sci. USA*, 101:6852-7). For efficient expression of the TMV-based viral vector in plant cells, the cDNA of the viral vector has been cloned between a plant promoter and a plant terminator (Act2 and nos) (Marillonnet, S., Giritch, A., Gils, M. et al., 2004, *Proc. Natl. Acad. Sci. USA.*, 101:6852-6857) and plant introns were added within the RdRP and MP sequences (Marillonnet, S., Thoeringer, C., Kandzia, R. et al., 2005, *Nat. Biotechnol.*, 23:718-723).

For expression of heteropolymeric proteins such as immunoglobulins, two proteins need to be expressed in the same cell, in the present case the immunoglobulin heavy and light chains. Since two different TMV-based viral vectors tend to exclude each other within infected cells, (only one vector will successfully replicate within a cell), we use two different viral vectors built on the cDNA of two viruses that are able to co-replicate within infected cells. This second virus is Potato Virus X (PVX; isolate PV-0018, "Deutsche Sammlung von Mikroorganismen and Zellkulturen GmbH" accession number PV-0018). PVX is a positive-strand RNA virus of the genus Potexvirus family Flexiviridae which naturally infects solanaceous and cruciferous plants by mechanical transmission. PVX has a different mode of replication than TMV. Like TMV, it contains a RdRp for replication, three genes for cell-to-cell movement (the triple gene block consisting of the 25K, 12K and 8K proteins), and a CP for formation of viral particles and systemic movement. An important difference with TMV is that the CP of PVX is also required for cell-to-cell movement. Therefore, it cannot be removed from the viral vector. In order to obtain high-level expression the gene of interest is cloned after the CP gene. In contrast to TMV-based vectors, introns are not required for efficient transport of the initial PVX vector transcript from the nucleus to the cytosol.

Figure 3:
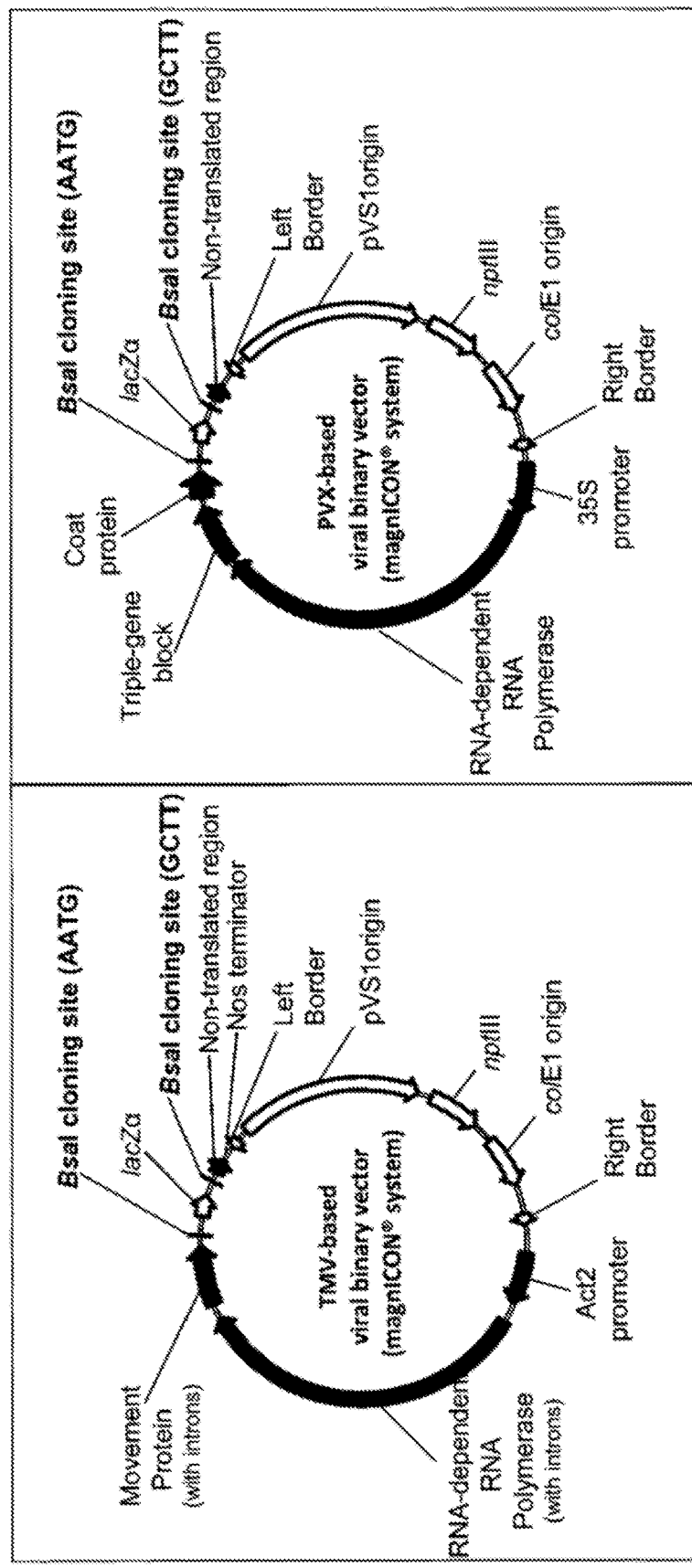
FIG. 3: Schematic presentation of binary viral cloning vectors based on plant viruses TMV and PVX (MagnICON® system). The T-DNA defined by the left and right boarders, contains a plant-active promoter (Act2 promoter), a coding sequence of the viral RNA-dependent RNA polymerase with introns, a viral movement protein coding sequence with introns, a BsaI cloning site containing lacZα, and the Nos terminator.

As for TMV vectors, we also use a promoter active in plants for generation of a primary transcript. However, in case of PVX vectors, we use the constitutive 35S promoter from the cauliflower mosaic virus. For PVX-based vectors, a plant terminator is not required. Finally, for both TMV and PVX-based vectors, we use *Agrobacterium tumefaciens* for efficient delivery of the viral vector to plant cells. Therefore, the complete viral vector (the plant promoter, viral vector sequences with gene of interest, and a plant terminator for TMV-based vectors) has been cloned between the T-DNA left and right borders of a binary vector (FIG. 3). The elements of the binary vector are the following: (1) a pVS1 origin of replication (Hajdukiewicz, P., Svab, Z. & Maliga, P., 1994, *Plant Mol Biol.*, 25:989-994) for plasmid replication in *Agrobacterium*, (2) a colE1origin for high level plasmid replication in *E. coli*, (3) an antibiotic resistance gene (nptIII providing kanamycin resistance, Frisch, D. A., Harris-Haller, L. W., Yokubaitis, N. T. et al., 1995, *Plant Mol. Biol.*, 27:405-409), and (4) T-DNA left and right borders (Frisch, D. A., Harris-Haller, L. W., Yokubaitis, N. T. et al., 1995, *Plant Mol. Biol.*, 27:405-409) to delimitate the ends of the piece of DNA transferred to plant cells. To facilitate blue/white selection a lacZαcassette amplified from pUC19 was inserted between two BsaI restriction sites which allow seamless in frame cloning of the gene of interest. Therefore, during initial construction of the viral vectors, all naturally occurring BsaI recognition sites were removed to allow easy and robust cloning of the gene of interest (FIG. 3).

Based on the amino acid sequences of Trastuzumab and Rituximab *Nicotiana tabacum* codon optimized versions of the variable regions were synthesized (FIG. 4-7). Additionally, generic Gamma 1 heavy chain and Kappa light chain constant regions were synthesized with *Nicotiana tabacum* codon usage (FIG. 1 A, FIG. 4-7). Type IIS enzyme BsaI restriction sites were added on both ends of the sequences to generate DNA modules which can be cloned together into a magnICON®-based plant viral expression vectors (FIG. 2 A, FIG. 3). In the generic Gamma 1 heavy chain constant region of Trastuzumab and Rituximab six single mutations (E293R, E294Y, Y296F, Y296E, Y300T, and Y300G) and one triple mutation (E294L+Y296T+Y300T) (FIG. 1 A) were introduced by PCR. The resulting Gamma 1 constant region DNA modules were cloned together with a signal peptide and a variable region sequence in PVX- and TMV-based magnICON® plant-viral vector using the type IIS enzyme BsaI (FIG. 2 A, FIG. 3). FIG. 2 depicts cloning of the fragments with mutations that led to the modulation of glycosylation of IgG1 Fc. The resulting heavy chain constructs were combined with the respective light chain construct for in planta expression.

Cloning of *Leishmania major* STT3-D gene (LmJF35.1160, acc. no. E9AET9) was performed in the way similar to the cloning of IgG1 heavy and light chains. Based on the amino acid sequence of *Leishmania major* STT3-D (LmJF35.1160, acc. no. E9AET9), a *Zea mays* codon-optimized version with a C-terminal His-tag and flanking BsaI type IIS enzyme restriction sites was synthesized (FIG. 1 B). The BsaI restriction sites were added to generate DNA modules which can be cloned together seamlessly into a binary expression vector between a 35S promoter and an OCS terminator (FIG. 2 B).

Example 2

Expression, Purification and Glycosylation Analysis of Recombinant Plant-Produced Antibody Having the Variable Regions of Rituximab For Ig production, both selected *Agrobacterium* strains harboring PVX and TMV vectors (Giritch et al., 2006, *Proc. Natl. Acad. Sci. USA*, 103:14701-14706) were grown separately in LB media with soya peptone (Duchefa Biochemie, Haarlem, The Netherlands) replacing tryptone. Bacterial cultures were grown at 28° C. until the $OD_{600}$ reaches 3 to 4. Infiltration solution was prepared by mixing and diluting both bacterial cultures in infiltration buffer (10 mM MES, pH 5.5, 10 mM MgSO4) to a defined cell concentration (equivalent to a 500-fold dilution of a culture with $OD_{600}$ of 1.0). *Nicotiana benthamiana* plants grown under controlled and standardized conditions were vacuum-infiltrated with the agrobacterial suspension (mixture of two agrobacterial strains harbouring TMV and PVX vectors) and then kept in the growth chambers for 7 days for Ig expression and accumulation. Plant biomass was then harvested (5 kg per batch), mixed with two volumes (w/v) of pre-chilled to +4° C. extraction buffer (200 mM Tris-HCl, pH 7.5, 5 mM EDTA) and homogenized in a blender. The pH of the homogenate was lowered to <5.1 for removal host cell proteins including rubisco. Subsequently, the pH of the homogenate was adjusted to 8.5 with NaOH and then the crude extract was clarified by dead-end filtration. The Ig from clarified extract was purified using Protein A affinity chromatography. The affinity eluate was ultra-/dia-filtrated against PBS (10 mM NaH2PO4, 137 mM NaCl, pH 7.3) and adjusted to a final protein concentration of 0.5-1.5 mg/mL using PBS buffer. Smaller batches of green biomass (1 g, 100 g, up to 1 kg) were treated as described in example 3.

The occupancy of N-glycans on antibodies was determined using capillary gel electrophoresis (CGE). For CGE-analysis the Agilent Bioanalyzer and Protein 230 kit was used according the instruction of the manufacturer. For analysis, 4 µl protein samples were combined with 2 µl reducing and denaturing sample buffer. For protein size estimation, the electrophoretic mobility of proteins in the samples was compared with the mobility of molecular weight markers (mixture of different size proteins with predetermined mass).

Figure 8:
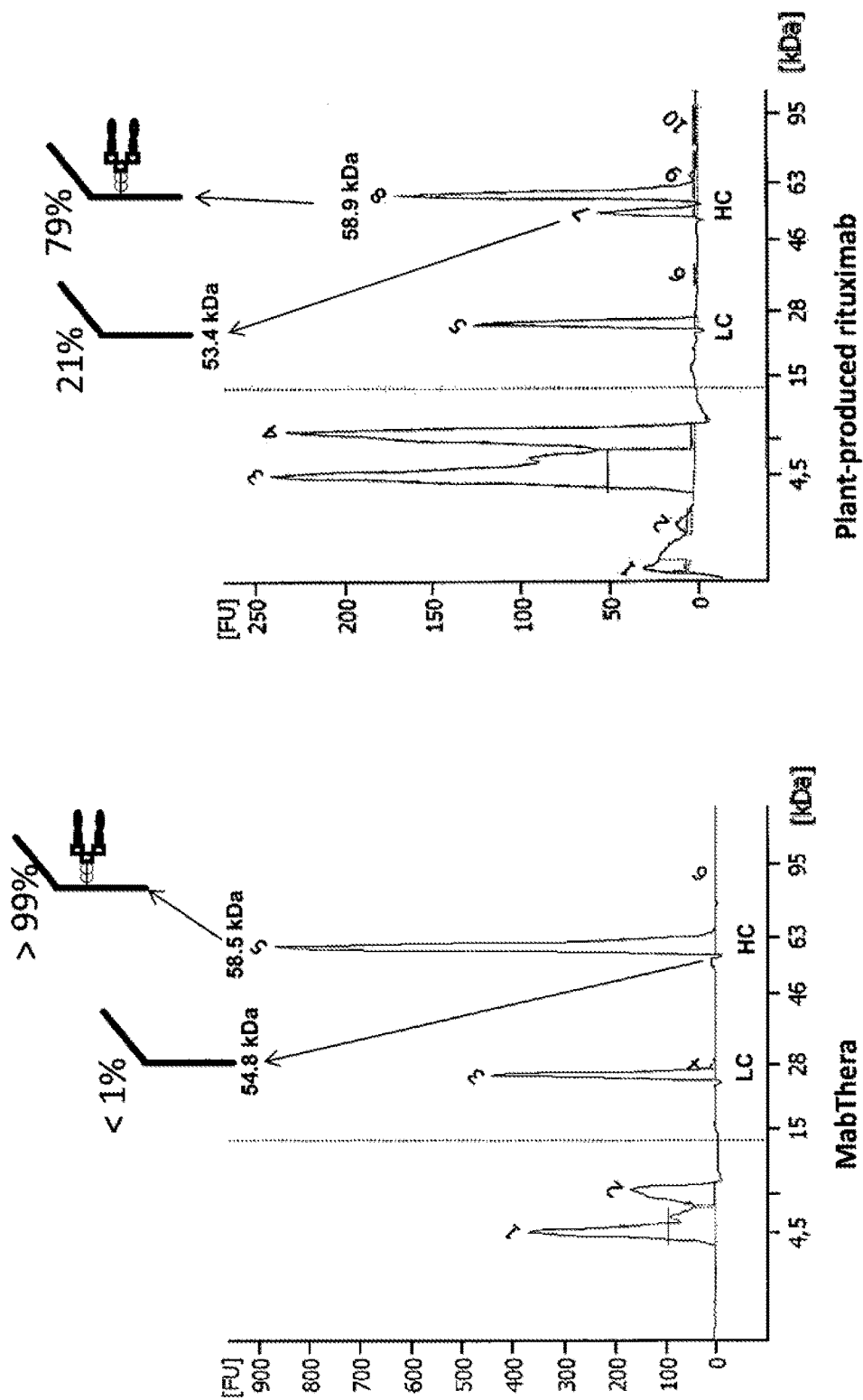
FIG. 8: Electropherograms of capillary gel electrophoretic (CGE) analysis of rituximab at reducing conditions. HC—heavy chain; LC—light chain; MabThera—commercially available rituxumab. Mole percentages of aglycosylated and glycosylated variants of HC are shown at the top of each electropherogram.
Figure 9:
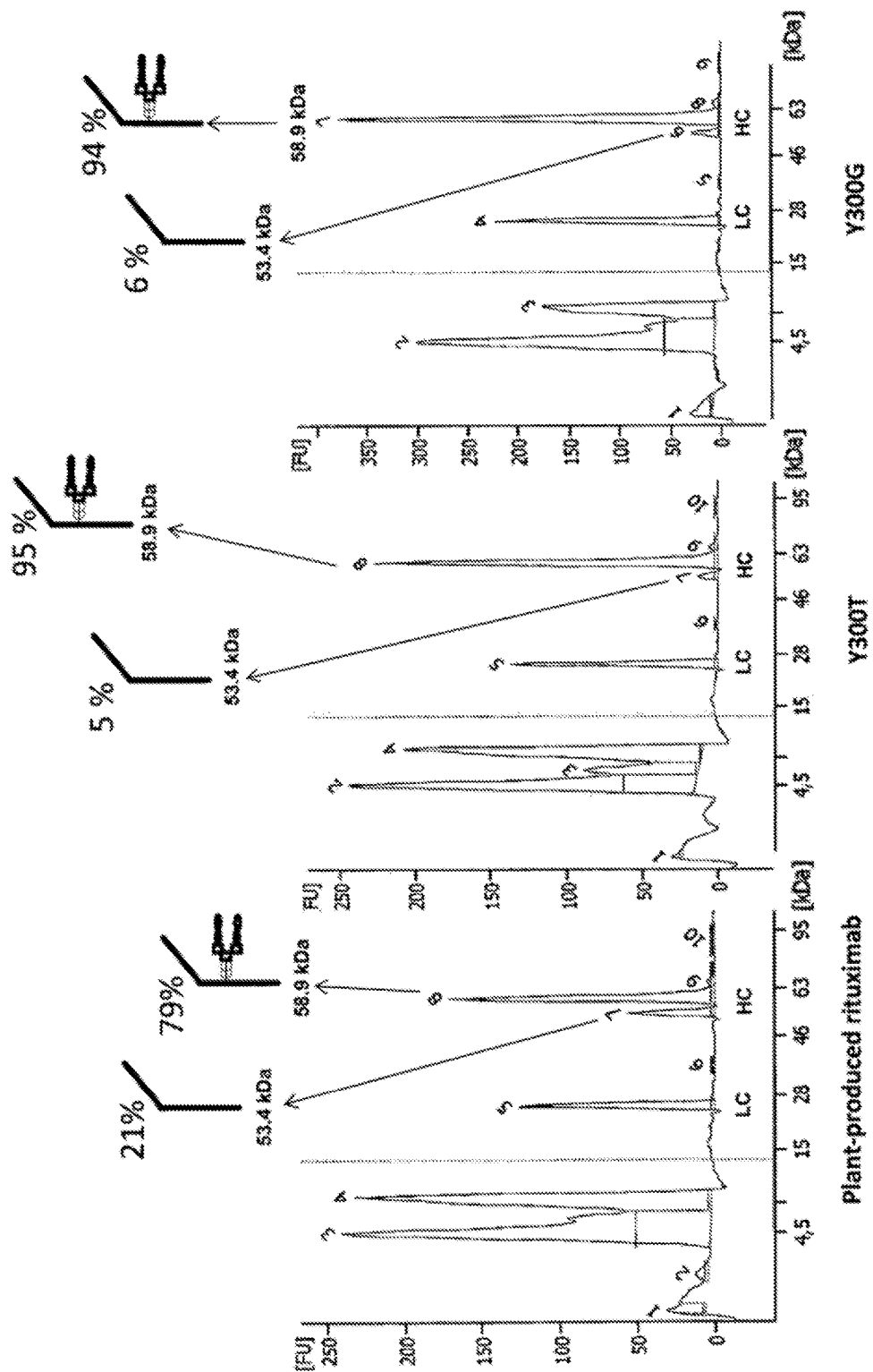
FIG. 9: Electropherograms of capillary gel electrophoretic (CGE) analysis of plant-produced rituximab and of its mutant variants at reducing conditions. HC—heavy chain; LC—light chain; Y300T—rituximab with Y to T amino acid substitution at position 300 of heavy chain corresponding to position +3 from the N-glycosylation site in the heavy chain constant region. Y300G—rituximab with Y to G amino acid substitution at position 300 of heavy chain. Approximate mole percentages of aglycosylated and glycosylated variants of HCs are shown at the top of corresponding peaks of the electropherogram.

The electropherograms of a reduced plant-produced rituximab and its Fc mutants are shown in FIGS. 8, 9 and 12. The heavy chain of the plant produced antibodies is divided in two peaks with molecular weight 53.4 kDa and 58.9 kDa corresponding to aglycosylated and glycosylated forms, respectively. This was confirmed by mass-spec analysis of glycopeptides (Example 4). The N-glycosylation site occupancy for the heavy chains of a plant expressed rituximab is ca. 79% for wild type Fc. This number decreases to 5-6% for Y300T and Y300G Fc mutants. Table 1 summarizes the N-glycosylation site occupancy for different Fc variants of plant-produced rituximab.

Plant-produced rituximab and its Fc mutant variants were also co-expressed together with STT3D gene. The process of performing experiments including plant infiltration, incubation, purification of IgG, was done in the same way as described above, except addition of agro with STT3D expression cassette to infiltration mix. However, taking into account that SST3D was expressed from a non-viral vector (pICH94911 depicted in FIG. 2B), concentration of agrobacteria carrying T-DNA with expression cassette for SST3D was ca. 50× higher than for magnICON vectors. The concentration of agrobacteria containing the vector was equivalent to a 4-fold dilution of a culture with $OD_{600}$ of 1.0. Results are shown in FIG. 12 C.

(Duchefa Biochemie, Haarlem, The Netherlands) replacing tryptone, and supplemented with 50 μg/mL rifampicin and 50 μg/mL kanamycin. Agrobacterial cultures are grown at 28° C. until $OD_{600}$ reaches 2 to 4. Infiltration solution is prepared by diluting the agrobacterial culture in infiltration buffer (10 mM MES, pH 5.5, 10 mM $MgSO_4$) to a defined cell concentration (equivalent to a 200-fold dilution of a culture with $OD_{600}$ of 1.0).

About 4 to 10 Nicotiana benthamiana plants, grown under controlled and standardized conditions for 6-8 weeks, were vacuum-infiltrated with the agrobacterial infiltration solution and then kept in the greenhouse for 6-8 days for expression and accumulation of the recombinant protein. Plant leaves were then harvested, ground in liquid nitrogen to a fine leaf powder and kept at –80° C. until protein extraction followed by purification.

The leaf powder (1 g to 1 kg batches size) was extracted in 20 mM sodium phosphate, pH 6.0, 0.5 M NaCl approximately two volumes (w/v) of extraction buffer. The extraction was performed on a shaker for 40 minutes at +4° C. The homogenate was clarified by centrifugation at 15.000×g for 10 minutes followed by filtration through MiraCloth filter. The pelleted plant tissue was re-extracted using the same extraction conditions. The extracts are combined and subjected to pH adjustment. The pH of the clarified homogenate is lowered to 5.0 using 5N HCl for removal of host cell proteins including rubisco. After incubation at pH 5 with stirring for about 30 minutes, the pH of the crude extract was

TABLE 1

Percentage of aglycosylated IgG1 Fc in different production batches of plant-made rituximab. The measurement of glycosylated and aglycosylated heavy chains ("HC glyc" and "HC aglyc", respectively) ratio was calculated using the area size of corresponding HC peaks from Capillary Gel Electrophoresis scans. CHO—CHO cell culture; N.b. wt—Nicotiana benthamiana (wild type) plants; N.b. RNAi—Nicotiana benthamiana plants with RNAi-silenced genes for fucosyl- and xylosyltransferases (Strasser, R. et al., 2008, Plant Biotechnol. J., 6: 392-402); N.b.RNAi(ΔXylT/FucT)—Nicotiana benthamiana plants combining knock-out genes (chemical mutagenesis of two genes encoding for xylosyl- and five encoding for fucosyltransferases) with RNAi silencing for fucosyl- and xylosyltransferases; MabThera - commercially rituximab; RIT—plant-made rituximab; Y296F, E294Y, Y300T, E294L-Y296T-Y300T, etc. - variants of plan-made rituximab, the designations of variants correspond to the amino acid substitutions within Fc region.

| Sample designation | Plant host | Batch size | HC aglyc kDa | HC glyc kDa | Difference kDa | HC aglyc Area | HC glyc Area | HC total Area | aglyc HC % |
|---|---|---|---|---|---|---|---|---|---|
| MabThera | CHO | | 54.8 | 58.5 | 3.7 | 22 | 2321 | 2343 | 1 |
| RIT | N.b. RNAi | 5 kg | 54.3 | 59.3 | 5 | 380 | 1281 | 1661 | 23 |
| RIT | N.b. RNAi | 5 kg | 54 | 58.8 | 4.8 | 202.8 | 730.5 | 933.3 | 22 |
| RIT | N.b. wt | 1 g | 55.1 | 60.2 | 5.1 | 4.5 | 22.9 | 27.4 | 16 |
| RIT | N.b. wt | 1 g | 55 | 60 | 5 | 2.3 | 8.1 | 10.4 | 22 |
| RIT | N.b. wt | 1 g | 55.7 | 60.8 | 5.1 | 229.6 | 878.6 | 1108.2 | 21 |
| Y296F | N.b. wt | 5 kg | 55.1 | 60.5 | 5.4 | 181.3 | 783 | 964.3 | 19 |
| Y296E | N.b. wt | 1 g | 54.8 | 59.9 | 5.1 | 89 | 62 | 151 | 59 |
| E294Y | N.b. wt | 1 g | 55.3 | 60.6 | 5.3 | 3.1 | 21.7 | 24.8 | 13 |
| E293R | N.b. wt | 1 g | 55.9 | 61.3 | 5.4 | 7.9 | 54.9 | 62.8 | 13 |
| Y300T | N.b. wt | 1 g | 54.5 | 60 | 5.5 | 11.6 | 233 | 244.6 | 5 |
| Y300G | N.b. wt | 1 g | 54.4 | 59.5 | 5.1 | 26.2 | 404.5 | 430.7 | 6 |
| E294L-Y296T-Y300T | N.b. wt | 1 g | 54.5 | 60.4 | 5.9 | 21.4 | 412 | 433.4 | 5 |
| Y300T | N.b. wt | 500 g | 55.4 | 60.3 | 4.9 | 229.9 | 2467.3 | 2697.2 | 9 |
| Y300T | N.b. RNAi (ΔXylT/FucT) | 500 g | 55.5 | 60.4 | 4.9 | 86.8 | 915.4 | 1002.2 | 9 |

Example 3

Expression, Purification and Qlycosylation Analysis of Recombinant Plant-Produced Trastuzumab For production of the recombinant proteins, the selected Agrobacterium strain harboring the TMV-based expression vector is grown in liquid LBS medium with soya peptone re-adjusted to pH 7.4 with 5N NaOH. The crude extract is then centrifuged (20.000×g for 15 minutes) to remove cell debris and precipitates. Before applying the crude extract to the affinity chromatography column, the crude extract is filtered through several filtration membranes (20 μm-8 μm-3 μm 0.45 μm). The clear filtrate is applied onto a spin column filled with 100 μL Protein A Sepharose (GE Healthcare, 17-5255-01), which was equilibrated with 10 CV washing buffer (20 mM sodium phosphate pH 7.3). After loading, the column is washed with 20 CV (column volumes) of washing buffer. The antibody was eluted with 5 CV elution buffer (10 mM sodium phosphate pH 3.0, 137 mM NaCl).

The eluted Ig is Ultra-/Diafiltrated using Spin-X UF concentrator 30k MWCO (Corning, #431489). Finally, the concentrate is sterile-filtrated using 0.2 μm filter. The protocol described in Example 2 was used for processing of 5 kg green biomass batches. The occupancy of N-glycans on antibodies was determined as described in Example 2.

Figure 10:
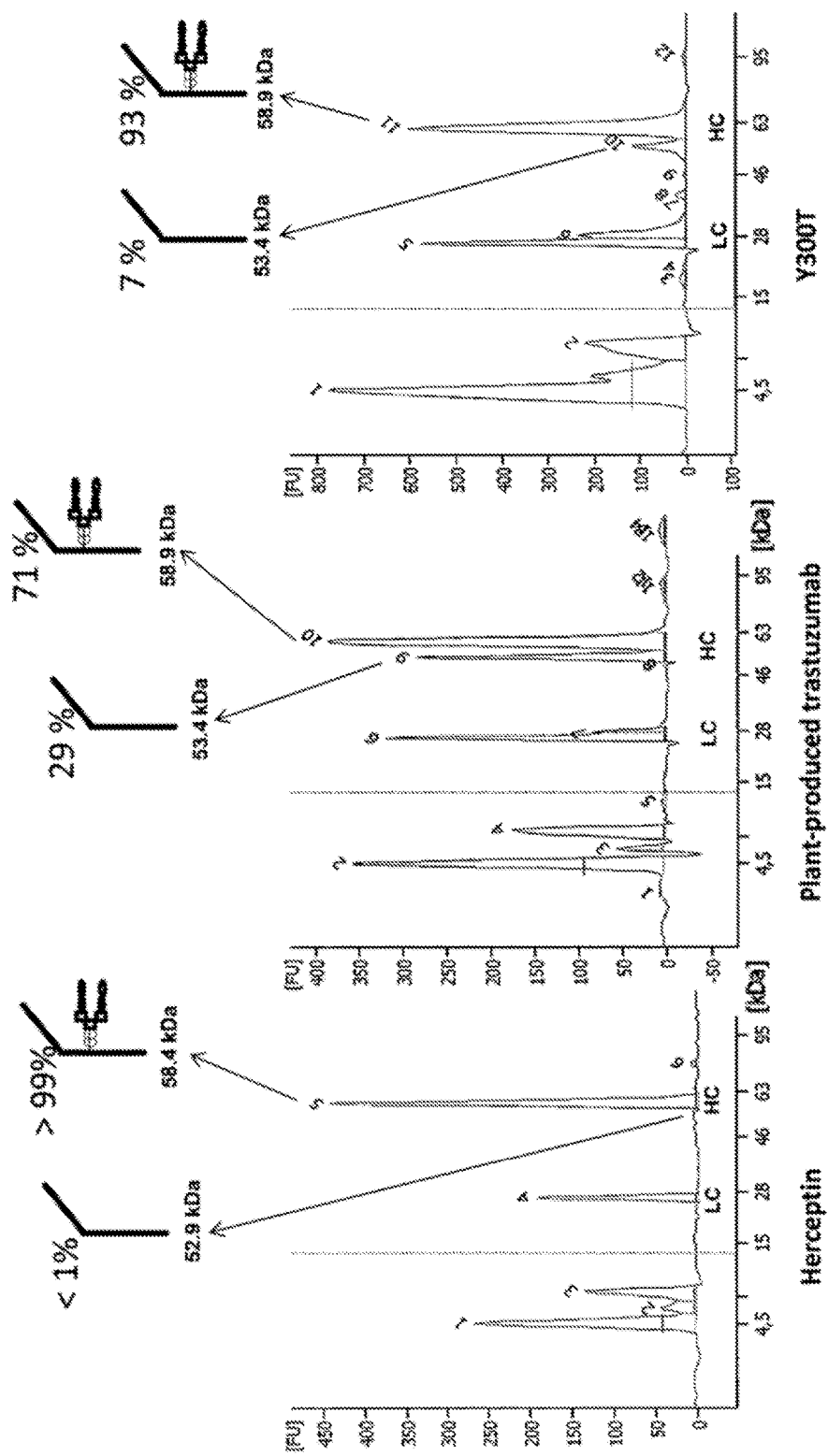
FIG. 10: Electropherograms of capillary gel electrophoretic (CGE) analysis of commercially available Herceptin, plant-produced trastuzumab and its mutant variant at reducing conditions. HC—heavy chain; LC—light chain; Y300T—trastuzumab with Y to T amino acid substitution at position 300 of heavy chain. Percentages of aglycosylated and glycosylated variants of HC are shown at the top of corresponding peacks of the electropherogram.
Figure 11:
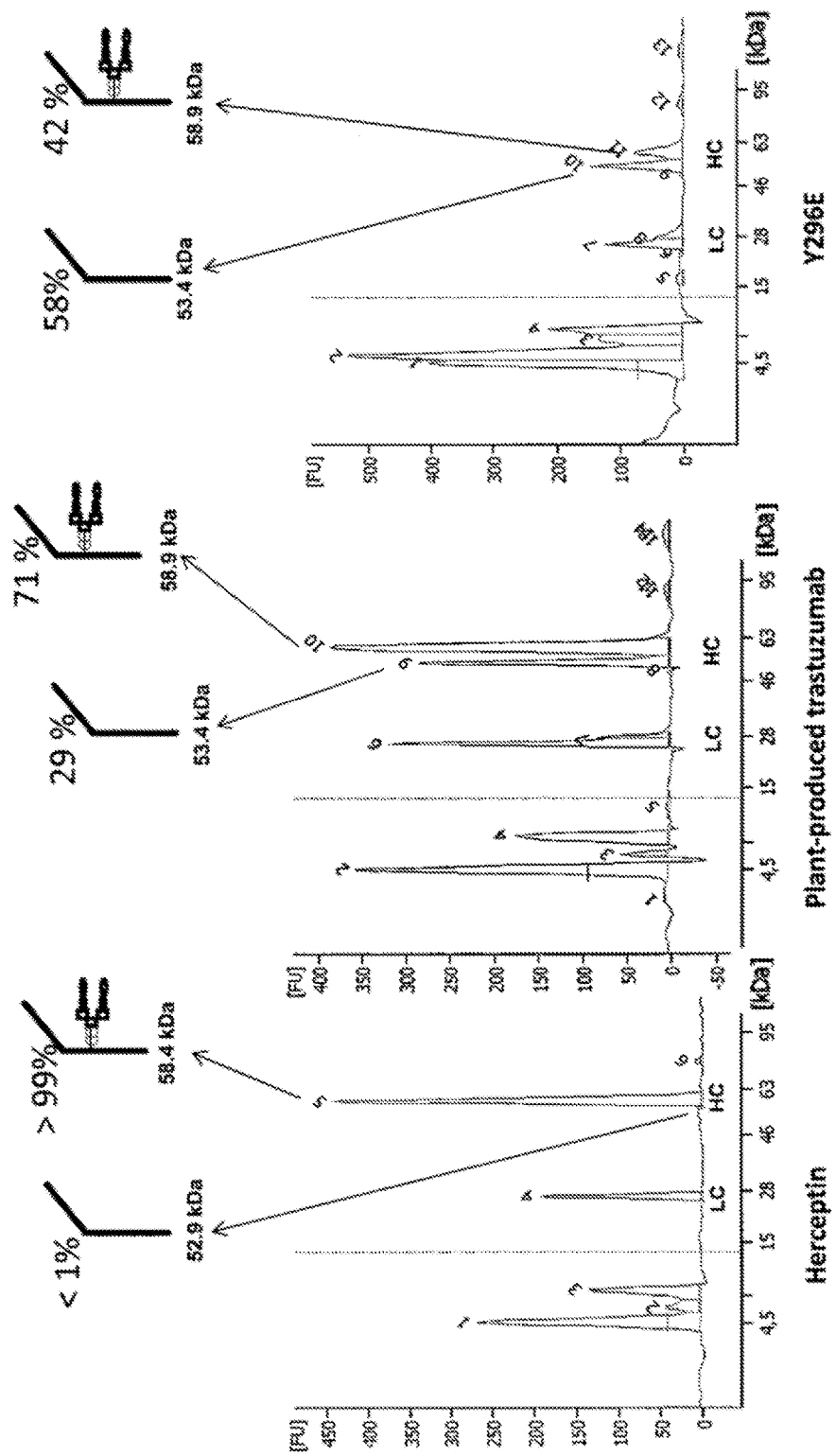
FIG. 11: Electropherograms of capillary gel electrophoretic (CGE) analysis of commercially available Herceptin, plant-produced trastuzumab and a mutant variant at reducing conditions. HC—heavy chain; LC—light chain; G296E—trastuzumab with Y to E amino acid substitution at position 296 of heavy chain. Percentages of aglycosylated and glycosylated variants of HC are shown at the top of corresponding peaks of the electropherogram.
Figure 12:
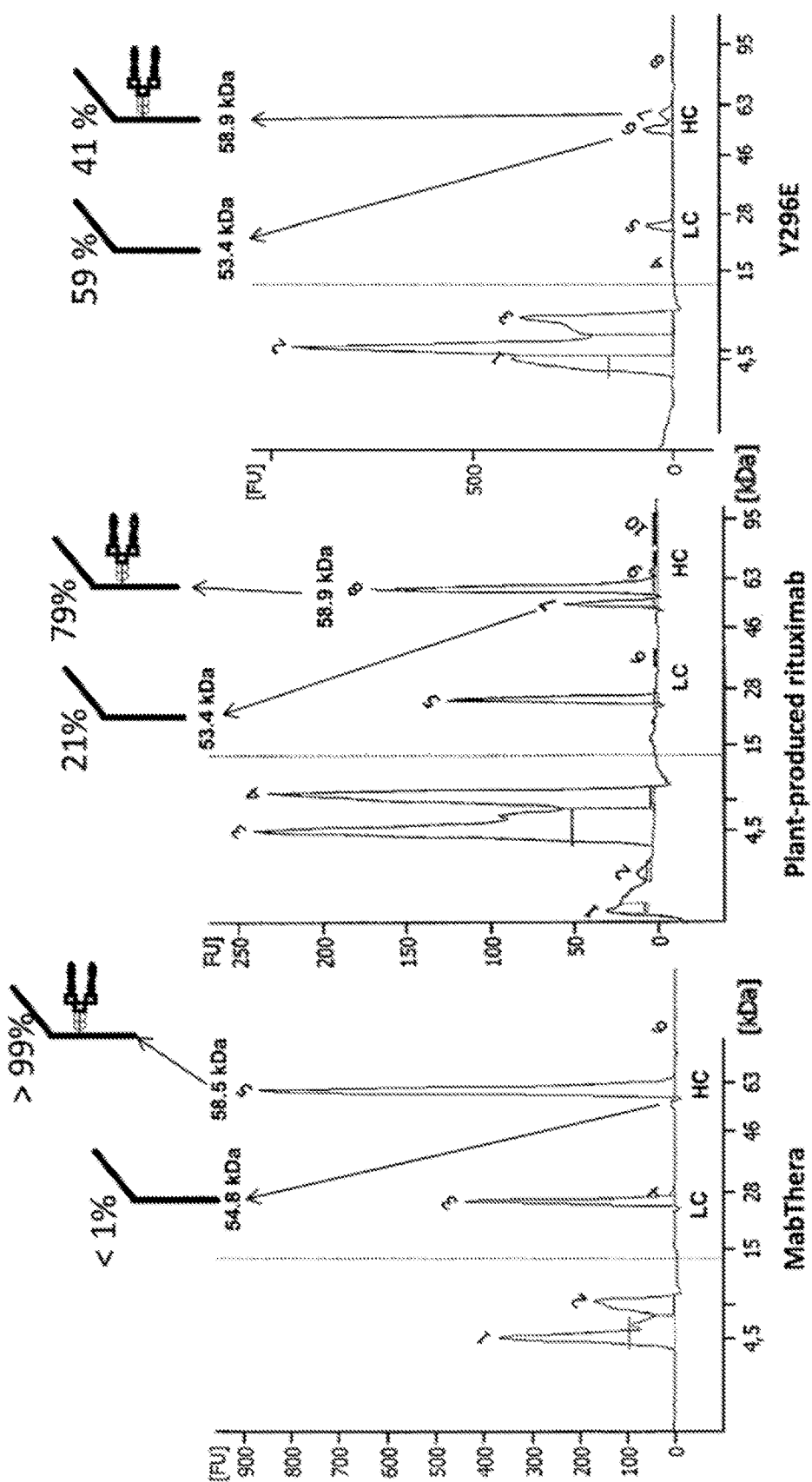
FIG. 12: A. Electropherograms of capillary gel electrophoretic (CGE) analysis of MabThera (commercially available rituximab), plant-produced rituximab and its mutant variant at reducing conditions. HC—heavy chain; LC—light chain; Y296E—rituximab with Y to E amino acid substitution at position 296 of the heavy chain. Percentages of aglycosylated and glycosylated variants of HC are shown at the top of corresponding peaks of the electropherogram. B. Electropherogram of capillary gel electrophoretic (CGE) analysis of anti-CD20 mouse mIgG2a; HC—heavy chain; LC—light chain. C. Electropherograms of capillary gel electrophoretic (CGE) analysis of plant-produced rituximab and trastuzumab with and without co-expression of LmSTT3-D gene. HC—heavy chain; LC—light chain; Percentages of aglycosylated and glycosylated variants of HC are shown at the top of corresponding peaks of the electropherogram.
Figure 12:
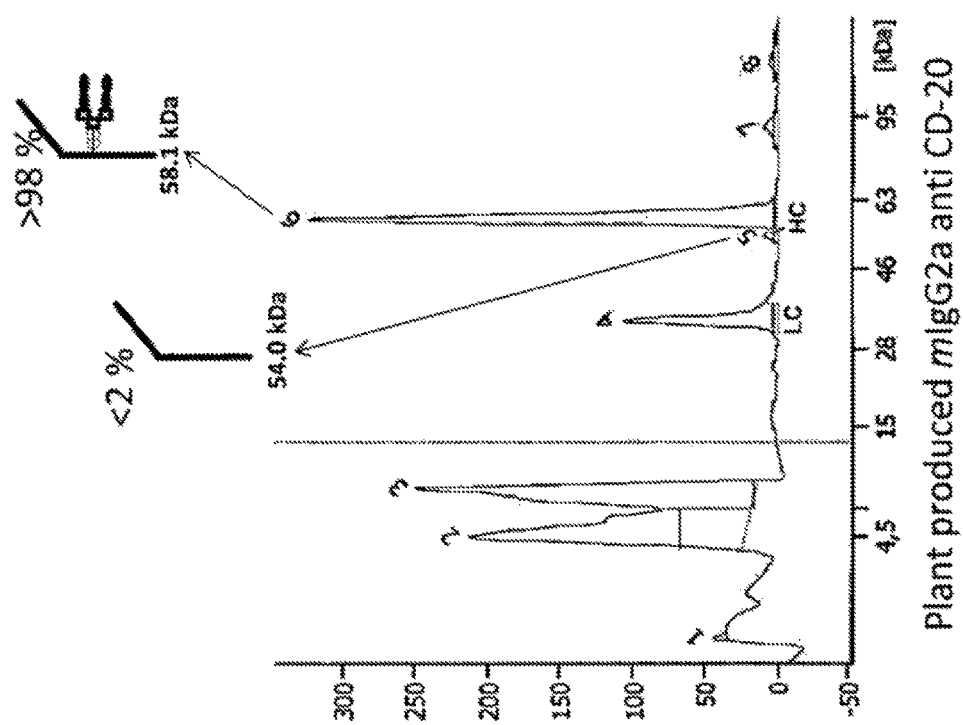
Figure 12:
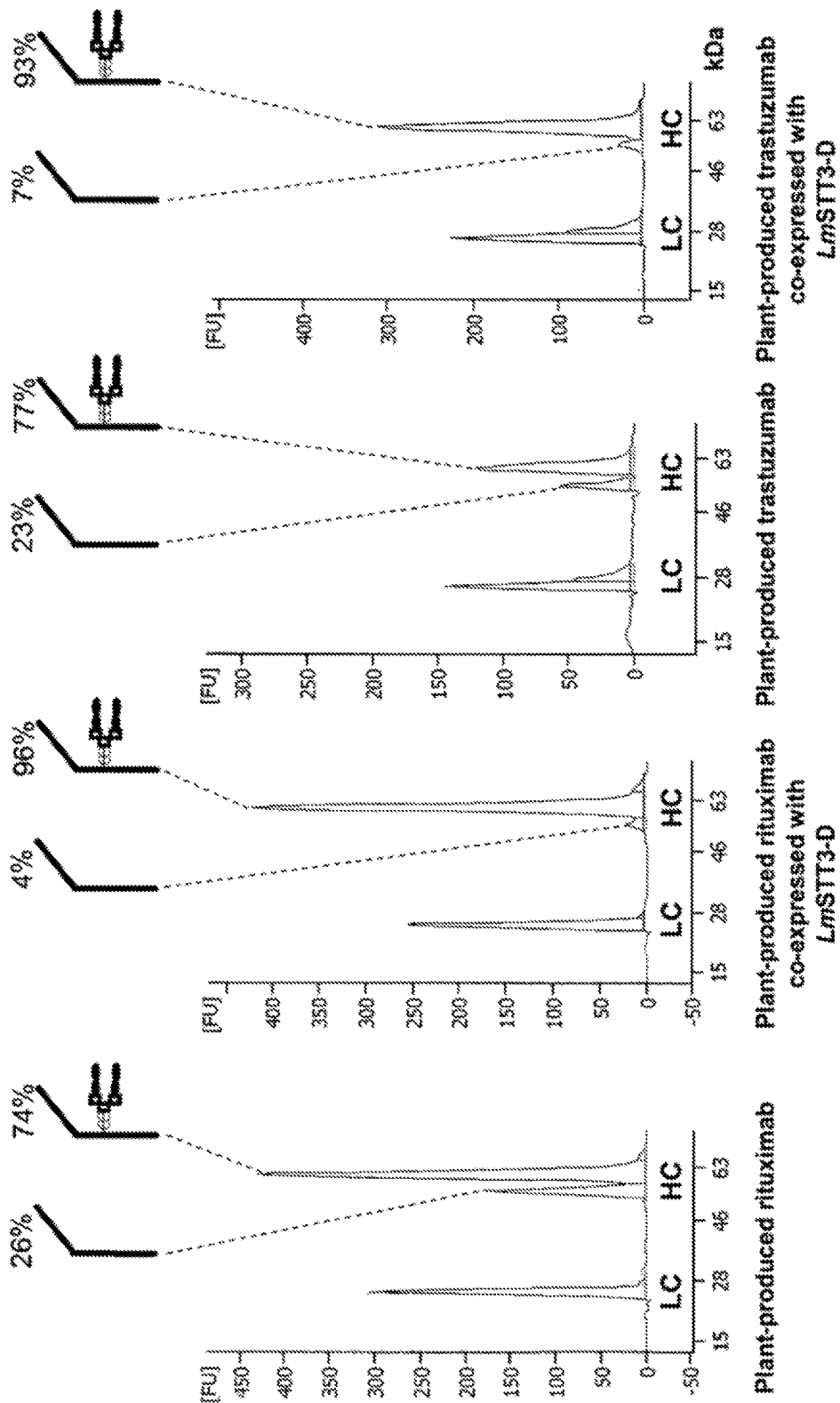

The electropherograms of reduced plant-produced trastuzumab and its Fc mutant version are shown in FIGS. 10 and 11. The heavy chain (HC) of plant produced trastuzumab is separated in two peaks with molecular weights of ca 53.4 kDa and 58.9 kDa. The 53.4 KDa peak corresponds to the aglycosylated heavy chain variant. Table 2 summarizes the N-glycosylation site occupancy for different Fc variants of plant-produced trastuzumab.

Plant-produced trastuzumab and its Fc mutant variants were also co-expressed together with STT3D gene. The process of performing experiments including plant infiltration, incubation, purification of IgG, was done in the same way as described above, except addition of *agrobacterium* with a STT3D expression cassette in T-DNA to the agrobacteria mixture used for infiltration. However, taking into account that SST3D is expressed from non-viral vector, concentration of agrobacteria carrying T-DNA with expression cassette for SST3D was ca. 50× higher than for viral vectors. The concentration of agrobacteria containing the vector was equivalent to a 4-fold dilution of a culture with $OD_{600}$ of 1.0. Results are shown in FIG. 12 C.

Example 4

Tryptic Glycopeptide Analysis by Reversed Phase LC-ESI-MS

10 μg of each sample was S-alkylated with iodoacetamide. The proteins were recovered by precipitation with acetone and digested with sequencing grade trypsin (Roche). About 3 μg of each digest was loaded on a BioBasic C18 column (BioBasic-18, 150×0.32 mm, 5 μm, Thermo Scientific) using 65 mM ammonium formate of pH 3.0 as the aqueous solvent. A gradient from 10 to 55% acetonitrile was developed over 20 min at a flow rate of 6 μL/min. Detection was performed with a Q-TOF mass spectrometer (Waters Micromass Q-TOF Ultima Global) in the positive ion, plain MS mode.

The MS profile was set to 450, 750 and 950. Instrument calibration was performed using caesium iodide. Glycopeptides were identified as sets of peaks consisting of the peptide moiety and the attached N-glycan varying in the attached sugar residues (Man, GlcNAc, Gal or Fuc) as indicated by the oligosaccharide analysis. The theoretical masses of these glycopeptides were determined with a spread sheet using mono-isotopic masses for amino acids and monosaccharides. A graphical depiction of the glycosylation status of each site was obtained by MaxEnt3 deconvolution of the summed spectra. The quantitative occurrence of each glycopeptide mass variant was deduced from the peak heights in the MaxEnt3 spectra. A hypothetical average glycan mass was calculated as the sum of the weighted averages (of the additional mass caused by the sugars). Non-glycosylated variants (as e.g. in the Fc region) have thus a "glycan mass" of 0. As an example, a calculation of percentages of aglycosylated and different glycoforms of glycosylated Fc glycopeptide are presented in Table 3.

TABLE 2

Percentage of aglycosylated IgG1 Fc in different production batches of plant-made trastuzumab. The measurement of glycosylated and aglycosylated Heavy Chains (HC glyc and HC aglyc, respectively) ratio was calculated using the area size of corresponding HC peaks from Capillary Gel Electrophoresis scans. CHO—CHO cell culture; N.b. wt—*Nicotiana benthamiana* (wild type) plants; N.b. RNAi—*Nicotiana benthamiana* plants with knock-down genes for fucosyl- and xylosyltransferases (Strasser, R. et al., 2008, Plant Biotechnol. J., 6: 392-402); Herceptin—commercially available trastuzumab; TRA—plant-made trastuzumab; Y296F, E294Y, E294L-Y296T-Y300T, etc. - variants of plan-made trastuzumab, the designations of variants correspond to the amino acid substitutions within Fc region.

| Sample designation | Host | Batch size | HC aglyc kDa | HC glyc kDa | Difference kDa | HC aglyc Area | HC glyc Area | HC total Area | aglyc HC % |
|---|---|---|---|---|---|---|---|---|---|
| Herceptin | CHO | | 52.9 | 58.4 | 5.5 | 0.1 | 473 | 473.1 | 0 |
| TRA | N.b. wt | 5 kg | 54.4 | 58.9 | 4.5 | 227 | 520 | 747 | 30 |
| TRA | N.b. RNAi | 5 kg | 52.3 | 58.9 | 6.6 | 193 | 445 | 638 | 30 |
| TRA | N.b. wt | 5 kg | 53.1 | 58.6 | 5.5 | 222 | 528 | 750 | 30 |
| TRA | N.b. wt | 5 kg | 53.4 | 58.6 | 5.2 | 324 | 963 | 1287 | 25 |
| TRA | N.b. wt | 1 g | 53 | 58.6 | 5.6 | 26.9 | 102.2 | 129.1 | 21 |
| TRA | N.b. wt | 1 g | 54.2 | 59.6 | 5.4 | 53.3 | 178 | 231.3 | 23 |
| TRA | N.b. wt | 1 g | 53.4 | 58.1 | 4.7 | 201.4 | 483.9 | 685.3 | 29 |
| Y296F | N.b. wt | 1 g | 53.7 | 58.9 | 5.2 | 60 | 261 | 321 | 19 |
| Y296E | N.b. wt | 1 g | 53.8 | 59.1 | 5.3 | 174 | 127 | 301 | 58 |
| E294Y | N.b. wt | 1 g | 53.7 | 59.2 | 5.5 | 22.7 | 55.6 | 78.3 | 29 |
| E293R | N.b. wt | 1 g | 53.9 | 59.8 | 5.9 | 75.7 | 354.5 | 430.2 | 18 |
| Y300T | N.b. wt | 1 g | 53.6 | 58.8 | 5.2 | 8.2 | 108.7 | 116.9 | 7 |
| Y300G | N.b. wt | 1 g | 53.1 | 58.7 | 5.6 | 9.2 | 116.6 | 125.8 | 7 |
| Y300T | N.b. wt | 500 g | 52.6 | 58.5 | 5.9 | 89.3 | 679.3 | 768.6 | 12 |
| E294L-Y296T-Y300T | N.b. wt | 1 g | 53.3 | 58.8 | 5.5 | 12.5 | 191.8 | 204.3 | 6 |

TABLE 3

Quantification of glycopeptides of plant-made trastuzumab with no modification of HC N-glycosylation site in terms of percentage (%) of total.

| Glycan structure | Theoretical mass | % of total |
| --- | --- | --- |
| Non-glycosylated peptide | 1189.51 | 23.8 |
| MM | 2081.91 | 0.2 |
| MMX | 2213.91 | 0.2 |
| MMF | 2227.91 | 0.4 |
| Man4 | 2243.91 | 0.3 |
| MGn | 2285.01 | 1.9 |
| MMXF | 2359.91 | 1.6 |
| Man5 | 2406.01 | 1.0 |
| MGnX | 2417.01 | 1.4 |
| MGnF | 2431.01 | 0.7 |
| GnGn | 2488.11 | 7.4 |
| MGnXF | 2563.01 | 4.6 |
| Man6 | 2568.01 | 1.4 |
| GnGnX | 2620.11 | 5.8 |
| GnGnF | 2634.11 | 2.9 |
| Man4GnXF | 2725.11 | 0.2 |
| Man7 | 2730.11 | 3.6 |
| GnGnXF | 2766.21 | 18.5 |
| GnAF | 2796.11 | 0.2 |
| Man8 | 2892.21 | 9.8 |
| Man9 | 3074.31 | 8.7 |
| Gn(FA)XF | 3092.11 | 4.6 |
| Man9Glc | 3216.31 | 0.2 |
| (FA)(FA)XF | 3382.21 | 0.5 |

The content of European patent application no. 13 002 866.5 filed on Jun. 4, 2013 is incorporated herein including description, claims and figures.

The invention claimed is:

1. A process of producing a recombinant glycoprotein in a *Nicotiana* plant, comprising transfecting said plant with a first *Agrobacterium* containing a first DNA molecule comprising a T-DNA comprising a nucleic acid construct containing a first DNA sequence of interest encoding a polypeptide having an N-glycosylation site, and transfecting said plant with a second *Agrobacterium* containing a second DNA molecule comprising a T-DNA comprising a nucleic acid construct containing a second DNA sequence encoding a heterologous single-subunit oligosaccharyltransferase (OTase); and expressing the first and the second DNA sequence to produce a glycosylated form of said polypeptide as said glycoprotein, wherein the first DNA sequence is expressed from a viral vector based on a plus-sense single-stranded plant RNA virus and the second DNA sequence is expressed from a non-viral vector under the control of a 35S promoter active in plant cells, and wherein the nucleic acid sequence encoding the single-subunit OTase is or comprises a nucleotide sequence encoding the amino acid sequence of SEQ ID NO: 2.

* * * * *

UNITED STATES PATENT AND TRADEMARK OFFICE
CERTIFICATE OF CORRECTION

PATENT NO. : 10,435,704 B2  
APPLICATION NO. : 14/895350  
DATED : October 8, 2019  
INVENTOR(S) : Franziska Jarczowski et al.

Page 1 of 1

It is certified that error appears in the above-identified patent and that said Letters Patent is hereby corrected as shown below:

On the Title Page

In the title, at (54) and in the Specification, Column 1, Line 3:
"OLICOSACCHARYLTRANSFERASE"
Should read:
"OLIGOSACCHARYLTRANSFERASE."

Signed and Sealed this
Second Day of June, 2020

Andrei Iancu
*Director of the United States Patent and Trademark Office*

SEQUENCE LISTING

<160> NUMBER OF SEQ ID NOS: 85

<210> SEQ ID NO 1
<211> LENGTH: 330
<212> TYPE: PRT
<213> ORGANISM: human

<400> SEQUENCE: 1

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240
```

```
Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 2
<211> LENGTH: 866
<212> TYPE: PRT
<213> ORGANISM: artificial
<220> FEATURE:
<223> OTHER INFORMATION: His-tagged Lleishmania major STT3-D

<400> SEQUENCE: 2

Met Gly Lys Arg Lys Gly Asn Ser Leu Gly Asp Ser Gly Ser Ala Ala
1               5                   10                  15

Thr Ala Ser Arg Glu Ala Ser Ala Gln Ala Glu Asp Ala Ala Ser Gln
            20                  25                  30

Thr Lys Thr Ala Ser Pro Pro Ala Lys Val Ile Leu Leu Pro Lys Thr
        35                  40                  45

Leu Thr Asp Glu Lys Asp Phe Ile Gly Ile Phe Pro Phe Pro Phe Trp
    50                  55                  60

Pro Val His Phe Val Leu Thr Val Val Ala Leu Phe Val Leu Ala Ala
65                  70                  75                  80

Ser Cys Phe Gln Ala Phe Thr Val Arg Met Ile Ser Val Gln Ile Tyr
                85                  90                  95

Gly Tyr Leu Ile His Glu Phe Asp Pro Trp Phe Asn Tyr Arg Ala Ala
            100                 105                 110

Glu Tyr Met Ser Thr His Gly Trp Ser Ala Phe Phe Ser Trp Phe Asp
        115                 120                 125

Tyr Met Ser Trp Tyr Pro Leu Gly Arg Pro Val Gly Ser Thr Thr Tyr
    130                 135                 140

Pro Gly Leu Gln Leu Thr Ala Val Ala Ile His Arg Ala Leu Ala Ala
145                 150                 155                 160

Ala Gly Met Pro Met Ser Leu Asn Asn Val Cys Val Leu Met Pro Ala
                165                 170                 175

Trp Phe Gly Ala Ile Ala Thr Ala Thr Leu Ala Phe Cys Thr Tyr Glu
            180                 185                 190

Ala Ser Gly Ser Thr Val Ala Ala Ala Ala Ala Leu Ser Phe Ser
        195                 200                 205

Ile Ile Pro Ala His Leu Met Arg Ser Met Ala Gly Glu Phe Asp Asn
    210                 215                 220

Glu Cys Ile Ala Val Ala Ala Met Leu Leu Thr Phe Tyr Cys Trp Val
225                 230                 235                 240

Arg Ser Leu Arg Thr Arg Ser Ser Trp Pro Ile Gly Val Leu Thr Gly
                245                 250                 255

Val Ala Tyr Gly Tyr Met Ala Ala Ala Trp Gly Gly Tyr Ile Phe Val
            260                 265                 270
```

-continued

```
Leu Asn Met Val Ala Met His Ala Gly Ile Ser Ser Met Val Asp Trp
    275                 280                 285

Ala Arg Asn Thr Tyr Asn Pro Ser Leu Leu Arg Ala Tyr Thr Leu Phe
    290                 295                 300

Tyr Val Gly Thr Ala Ile Ala Val Cys Val Pro Pro Val Gly Met
305                 310                 315                 320

Ser Pro Phe Lys Ser Leu Glu Gln Leu Gly Ala Leu Leu Val Leu Val
                325                 330                 335

Phe Leu Cys Gly Leu Gln Val Cys Glu Val Leu Arg Ala Arg Ala Gly
            340                 345                 350

Val Glu Val Arg Ser Arg Ala Asn Phe Lys Ile Arg Val Arg Val Phe
        355                 360                 365

Ser Val Met Ala Gly Val Ala Ala Leu Ala Ile Ser Val Leu Ala Pro
    370                 375                 380

Thr Gly Tyr Phe Gly Pro Leu Ser Val Arg Val Arg Ala Leu Phe Val
385                 390                 395                 400

Glu His Thr Arg Thr Gly Asn Pro Leu Val Asp Ser Val Ala Glu His
                405                 410                 415

Gln Pro Ala Ser Pro Glu Ala Met Trp Ala Phe Leu His Val Cys Gly
            420                 425                 430

Val Thr Trp Gly Leu Gly Ser Ile Val Leu Ala Val Ser Thr Phe Val
        435                 440                 445

His Tyr Ser Pro Ser Lys Val Phe Trp Leu Leu Asn Ser Gly Ala Val
    450                 455                 460

Tyr Tyr Phe Ser Thr Arg Met Ala Arg Leu Leu Leu Ser Gly Pro
465                 470                 475                 480

Ala Ala Cys Leu Ser Thr Gly Ile Phe Val Gly Thr Ile Leu Glu Ala
                485                 490                 495

Ala Val Gln Leu Ser Phe Trp Asp Ser Asp Ala Thr Lys Ala Lys Lys
            500                 505                 510

Gln Gln Lys Gln Ala Gln Arg His Gln Arg Gly Ala Gly Lys Gly Ser
        515                 520                 525

Gly Arg Asp Asp Ala Lys Asn Ala Thr Thr Ala Arg Ala Phe Cys Asp
    530                 535                 540

Val Phe Ala Gly Ser Ser Leu Ala Trp Gly His Arg Met Val Leu Ser
545                 550                 555                 560

Ile Ala Met Trp Ala Leu Val Thr Thr Thr Ala Val Ser Phe Phe Ser
                565                 570                 575

Ser Glu Phe Ala Ser His Ser Thr Lys Phe Ala Glu Gln Ser Ser Asn
            580                 585                 590

Pro Met Ile Val Phe Ala Ala Val Val Gln Asn Arg Ala Thr Gly Lys
        595                 600                 605

Pro Met Asn Leu Leu Val Asp Asp Tyr Leu Lys Ala Tyr Glu Trp Leu
    610                 615                 620

Arg Asp Ser Thr Pro Glu Asp Ala Arg Val Leu Ala Trp Trp Asp Tyr
625                 630                 635                 640

Gly Tyr Gln Ile Thr Gly Ile Gly Asn Arg Thr Ser Leu Ala Asp Gly
                645                 650                 655

Asn Thr Trp Asn His Glu His Ile Ala Thr Ile Gly Lys Met Leu Thr
            660                 665                 670

Ser Pro Val Val Glu Ala His Ser Leu Val Arg His Met Ala Asp Tyr
        675                 680                 685
```

Val Leu Ile Trp Ala Gly Gln Ser Gly Asp Leu Met Lys Ser Pro His
        690                 695                 700

Met Ala Arg Ile Gly Asn Ser Val Tyr His Asp Ile Cys Pro Asp Asp
705                 710                 715                 720

Pro Leu Cys Gln Gln Phe Gly Phe His Arg Asn Asp Tyr Ser Arg Pro
                    725                 730                 735

Thr Pro Met Met Arg Ala Ser Leu Leu Tyr Asn Leu His Glu Ala Gly
                740                 745                 750

Lys Arg Lys Gly Val Lys Val Asn Pro Ser Leu Phe Gln Glu Val Tyr
        755                 760                 765

Ser Ser Lys Tyr Gly Leu Val Arg Ile Phe Lys Val Met Asn Val Ser
770                 775                 780

Ala Glu Ser Lys Lys Trp Val Ala Asp Pro Ala Asn Arg Val Cys His
785                 790                 795                 800

Pro Pro Gly Ser Trp Ile Cys Pro Gly Gln Tyr Pro Pro Ala Lys Glu
                805                 810                 815

Ile Gln Glu Met Leu Ala His Arg Val Pro Phe Asp Val Thr Asn
                820                 825                 830

Ala Asp Arg Lys Asn Asn Val Gly Ser Tyr Gln Glu Glu Tyr Met Arg
        835                 840                 845

Arg Met Arg Glu Ser Glu Asn Arg Arg Gly Ser Gly His His His
        850                 855                 860

His His
865

<210> SEQ ID NO 3
<211> LENGTH: 321
<212> TYPE: DNA
<213> ORGANISM: artificial
<220> FEATURE:
<223> OTHER INFORMATION: nucleic acid sequence of recombinant
      Trastuzumab variable region kappa light chain

<400> SEQUENCE: 3
gatatacaga tgactcaatc accatcttca cttagtgcta gtgttggaga tagagtgacg        60
attacatgtc gtgcatcaca agacgtgaat acagctgtag catggtatca gcagaaacct      120
ggtaaagctc cgaagttgct catctattct gcgagtttcc tatactctgg tgttccatcc      180
aggttttctg gtctagaag cggaactgac ttcactctga ccattagctc cttacaacct       240
gaagattttg ccacttacta ttgccagcaa cattacacta caccacctac ctttggacaa      300
ggcacaaagg tcgagattaa g                                                321

<210> SEQ ID NO 4
<211> LENGTH: 321
<212> TYPE: DNA
<213> ORGANISM: artificial
<220> FEATURE:
<223> OTHER INFORMATION: nucleic acid sequence of generic kappa constant
      regions

<400> SEQUENCE: 4
cgaacagttg ctgctcctag tgtttttatt ttccccccat ccgatgaaca attgaaatct        60
ggaactgcat ccgtaaattt ctaccctaga gaagctaagg ttcaatggaa agtcgataat      120
gcactacagt ctggtaattc acaagagtct gttactgaac aagacgtatg cttgttgaac      180
tctaaggact ctacttacag tctttcttca actcttaccc tatcaaaggc agattacgaa      240
aagcataagg tctatgcttg tgaagttaca catcaaggat tgagttcacc agttacaaag      300

```
agttttaacc gtggtgagtg t                                              321
```

<210> SEQ ID NO 5
<211> LENGTH: 107
<212> TYPE: PRT
<213> ORGANISM: artificial
<220> FEATURE:
<223> OTHER INFORMATION: amino acid sequence of Trastuzumab kappa light
      chain

<400> SEQUENCE: 5

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys
            100                 105
```

<210> SEQ ID NO 6
<211> LENGTH: 107
<212> TYPE: PRT
<213> ORGANISM: artificial
<220> FEATURE:
<223> OTHER INFORMATION: amino acid sequence of generic kappa constant
      regions

<400> SEQUENCE: 6

```
Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105
```

<210> SEQ ID NO 7
<211> LENGTH: 360
<212> TYPE: DNA
<213> ORGANISM: artificial
<220> FEATURE:
<223> OTHER INFORMATION: nucleic acid sequence of variable region of
      Trastuzumab heavy chain

<400> SEQUENCE: 7

```
gaggtacagt tggtggaatc tggtggtgga ttggttcaac ctggaggatc tcttaggcta      60
```

```
agttgtgcag cttcaggctt caacatcaag gacacctaca ttcattgggt tagacaagct    120
ccaggtaaag ggttagaatg ggtagcaagg atatatccca caaatgggta tactcgatat    180
gcagactcag tgaaaggacg ttttaccatt tctgccgata cgagcaagaa tactgcctat    240
cttcagatga actctctgag agctgaggat actgctgtct actactgcag tagatggggc    300
ggtgatggct tttatgcgat ggattactgg ggacaaggta cactcgttac agtttcttca    360
```

<210> SEQ ID NO 8
<211> LENGTH: 120
<212> TYPE: PRT
<213> ORGANISM: artificial
<220> FEATURE:
<223> OTHER INFORMATION: amino acid sequence of variable region of
      Trastuzumab heavy chain

<400> SEQUENCE: 8

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser
        115                 120
```

<210> SEQ ID NO 9
<211> LENGTH: 990
<212> TYPE: DNA
<213> ORGANISM: artificial
<220> FEATURE:
<223> OTHER INFORMATION: Generic IgG1 (CH3 EEM) constant region

<400> SEQUENCE: 9

```
gccagcacta aaggaccatc agtatttccc cttgcacctt catctaagag tacttctggt     60
ggaactgcag ctttgggttg cttagtgaag gattatttcc ctgagcctgt tactgtttct    120
tggaattctg gtgcccttac ttctggtgtt catactttcc ctgcagtctt acaaagcagt    180
ggtttgtatt ccctgagcag tgttgtaact gttccatctt caagtctagg tacccagacc    240
tacatctgta atgtcaacca caagcccagc aatactaagg tcgataagaa ggttgagccc    300
aagtcatgtg ataagacaca tacttgtcca ccttgtccag ctccagaatt gttgggcgga    360
ccatctgttt ttttgttccc acccaagcct aaagataccc tcatgatatc cagaacccct    420
gaagttacat gcgtagttgt agacgttagt catgaggatc ctgaggtcaa gtttaattgg    480
tatgtggatg gagtggaagt gcataatgca agacaaagc caagagagga gcagtacaac    540
tcaacataca gtggtatc agtgctgact gttcttcacc aagattggct gaatgggaaa    600
gagtataagt gcaaggtgtc taataaggct ttaccagctc ccatcgaaaa gaccattagc    660
aaggctaaag acaaccaag agagcctcaa gtatatacac ttcctccatc ccgtgaggaa    720
```

-continued

```
atgactaaga accaggtttc tctcacatgt ctagtgaagg ggttttaccc atctgacatt    780
gctgttgaat gggaaagcaa tggccagcct gaaataact ataagaccac accacctgtt    840
ctagacagtg atggatcctt tttcctgtac tccaagctca cagtagacaa atctagatgg    900
caacaaggga acgtgttttc atgcagtgtt atgcatgaag cccttcacaa ccactataca    960
cagaagtcac tgagtctctc acctggtaag                                    990
```

```
<210> SEQ ID NO 10
<211> LENGTH: 330
<212> TYPE: PRT
<213> ORGANISM: artificial
<220> FEATURE:
<223> OTHER INFORMATION: Generic IgG1 (CH3 EEM) constant region

<400> SEQUENCE: 10
```

| | | | | | | | | | | | | | | | |
|---|---|---|---|---|---|---|---|---|---|---|---|---|---|---|---|
| Ala | Ser | Thr | Lys | Gly | Pro | Ser | Val | Phe | Pro | Leu | Ala | Pro | Ser | Ser | Lys |
| 1 | | | | 5 | | | | | 10 | | | | | 15 | |
| Ser | Thr | Ser | Gly | Gly | Thr | Ala | Ala | Leu | Gly | Cys | Leu | Val | Lys | Asp | Tyr |
| | | | 20 | | | | | 25 | | | | | 30 | | |
| Phe | Pro | Glu | Pro | Val | Thr | Val | Ser | Trp | Asn | Ser | Gly | Ala | Leu | Thr | Ser |
| | | 35 | | | | | 40 | | | | | 45 | | | |
| Gly | Val | His | Thr | Phe | Pro | Ala | Val | Leu | Gln | Ser | Ser | Gly | Leu | Tyr | Ser |
| | 50 | | | | | 55 | | | | | 60 | | | | |
| Leu | Ser | Ser | Val | Val | Thr | Val | Pro | Ser | Ser | Ser | Leu | Gly | Thr | Gln | Thr |
| 65 | | | | | 70 | | | | | 75 | | | | | 80 |
| Tyr | Ile | Cys | Asn | Val | Asn | His | Lys | Pro | Ser | Asn | Thr | Lys | Val | Asp | Lys |
| | | | | 85 | | | | | 90 | | | | | 95 | |
| Lys | Val | Glu | Pro | Lys | Ser | Cys | Asp | Lys | Thr | His | Thr | Cys | Pro | Pro | Cys |
| | | | 100 | | | | | 105 | | | | | 110 | | |
| Pro | Ala | Pro | Glu | Leu | Leu | Gly | Gly | Pro | Ser | Val | Phe | Leu | Phe | Pro | Pro |
| | | 115 | | | | | 120 | | | | | 125 | | | |
| Lys | Pro | Lys | Asp | Thr | Leu | Met | Ile | Ser | Arg | Thr | Pro | Glu | Val | Thr | Cys |
| | 130 | | | | | 135 | | | | | 140 | | | | |
| Val | Val | Val | Asp | Val | Ser | His | Glu | Asp | Pro | Glu | Val | Lys | Phe | Asn | Trp |
| 145 | | | | | 150 | | | | | 155 | | | | | 160 |
| Tyr | Val | Asp | Gly | Val | Glu | Val | His | Asn | Ala | Lys | Thr | Lys | Pro | Arg | Glu |
| | | | | 165 | | | | | 170 | | | | | 175 | |
| Glu | Gln | Tyr | Asn | Ser | Thr | Tyr | Arg | Val | Val | Ser | Val | Leu | Thr | Val | Leu |
| | | | 180 | | | | | 185 | | | | | 190 | | |
| His | Gln | Asp | Trp | Leu | Asn | Gly | Lys | Glu | Tyr | Lys | Cys | Lys | Val | Ser | Asn |
| | | 195 | | | | | 200 | | | | | 205 | | | |
| Lys | Ala | Leu | Pro | Ala | Pro | Ile | Glu | Lys | Thr | Ile | Ser | Lys | Ala | Lys | Gly |
| | 210 | | | | | 215 | | | | | 220 | | | | |
| Gln | Pro | Arg | Glu | Pro | Gln | Val | Tyr | Thr | Leu | Pro | Pro | Ser | Arg | Glu | Glu |
| 225 | | | | | 230 | | | | | 235 | | | | | 240 |
| Met | Thr | Lys | Asn | Gln | Val | Ser | Leu | Thr | Cys | Leu | Val | Lys | Gly | Phe | Tyr |
| | | | | 245 | | | | | 250 | | | | | 255 | |
| Pro | Ser | Asp | Ile | Ala | Val | Glu | Trp | Glu | Ser | Asn | Gly | Gln | Pro | Glu | Asn |
| | | | 260 | | | | | 265 | | | | | 270 | | |
| Asn | Tyr | Lys | Thr | Thr | Pro | Pro | Val | Leu | Asp | Ser | Asp | Gly | Ser | Phe | Phe |
| | | 275 | | | | | 280 | | | | | 285 | | | |
| Leu | Tyr | Ser | Lys | Leu | Thr | Val | Asp | Lys | Ser | Arg | Trp | Gln | Gln | Gly | Asn |
| | 290 | | | | | 295 | | | | | 300 | | | | |
| Val | Phe | Ser | Cys | Ser | Val | Met | His | Glu | Ala | Leu | His | Asn | His | Tyr | Thr |

Gln Lys Ser Leu Ser Leu Ser Pro Gly Lys
305           310           315           320
                325           330

<210> SEQ ID NO 11
<211> LENGTH: 318
<212> TYPE: DNA
<213> ORGANISM: Artificial
<220> FEATURE:
<223> OTHER INFORMATION: Variable region of Rituximab Kappa light chain

<400> SEQUENCE: 11
cagatagtgc ttagccaatc accagcaatt tgtctgcat cacctggtga aaggttacg    60 atgacttgta gagctagctc ctcagtgtcc tacatccatt ggttccaaca gaaaccaggc    120
agttctccta aaccctggat ttatgccaca tctaacttag cttctggtgt acctgtcagg    180
tttagtggct ctggaagtgg gacaagctat tcactgacca tatctcgtgt tgaagcggaa    240
gatgcagcta cctactattg ccaacagtgg acttccaatc caccgacatt tggaggaggt    300
actaagctcg agattaag                                                 318

<210> SEQ ID NO 12
<211> LENGTH: 106
<212> TYPE: PRT
<213> ORGANISM: Artificial
<220> FEATURE:
<223> OTHER INFORMATION: Variable region of Rituximab Kappa light chain

<400> SEQUENCE: 12

Gln Ile Val Leu Ser Gln Ser Pro Ala Ile Leu Ser Ala Ser Pro Gly
1               5                   10                  15

Glu Lys Val Thr Met Thr Cys Arg Ala Ser Ser Ser Val Ser Tyr Ile
            20                  25                  30

His Trp Phe Gln Gln Lys Pro Gly Ser Ser Pro Lys Pro Trp Ile Tyr
        35                  40                  45

Ala Thr Ser Asn Leu Ala Ser Gly Val Pro Val Arg Phe Ser Gly Ser
    50                  55                  60

Gly Ser Gly Thr Ser Tyr Ser Leu Thr Ile Ser Arg Val Glu Ala Glu
65                  70                  75                  80

Asp Ala Ala Thr Tyr Tyr Cys Gln Gln Trp Thr Ser Asn Pro Pro Thr
                85                  90                  95

Phe Gly Gly Gly Thr Lys Leu Glu Ile Lys
            100                 105

<210> SEQ ID NO 13
<211> LENGTH: 321
<212> TYPE: DNA
<213> ORGANISM: Artificial
<220> FEATURE:
<223> OTHER INFORMATION: Generic Kappa constant region

<400> SEQUENCE: 13
cgaacagttg ctgctcctag tgtttttatt tttccccat ccgatgaaca attgaaatct    60
ggaactgcat ccgtagtatg cttgttgaac aatttctacc ctagagaagc taaggttcaa    120
tggaaagtcg ataatgcact acagtctggt aattcacaag agtctgttac tgaacaagac    180
tctaaggact ctacttacag tctttcttca actcttaccc tatcaaaggc agattacgaa    240
aagcataagg tctatgcttg tgaagttaca catcaaggat tgagttcacc agttacaaag    300
agttttaacc gtggtgagtg t                                             321

<210> SEQ ID NO 14
<211> LENGTH: 107
<212> TYPE: PRT
<213> ORGANISM: Artificial
<220> FEATURE:
<223> OTHER INFORMATION: Generic Kappa constant region

<400> SEQUENCE: 14

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 15
<211> LENGTH: 363
<212> TYPE: DNA
<213> ORGANISM: Artificial
<220> FEATURE:
<223> OTHER INFORMATION: Variable region of Rituximab heavy chain

<400> SEQUENCE: 15
caagttcagc tacaacaacc aggagctgaa ctggttaaac ctggtgcatc tgtcaagatg    60
tcatgcaaag cttcagggta cctttact agctataaca tgcattgggt taagcaaact    120
ccaggtagag gattagagtg gataggggcg atttatcccg gaaatggcga tacctcttac    180
aaccagaagt ttaagggcaa agcaacactt actgctgaca atcctcttc tacagcctat    240 atgcagctct ctagcttgac atccgaagat agtgctgtgt attactgtgc taggagtacg    300
tactatggtg agattggta cttcaatgta tggggtgcag gaactactgt gacagtatca    360
gct    363

<210> SEQ ID NO 16
<211> LENGTH: 121
<212> TYPE: PRT
<213> ORGANISM: artificial
<220> FEATURE:
<223> OTHER INFORMATION: Variable region of Rituximab heavy chain

<400> SEQUENCE: 16

Gln Val Gln Leu Gln Gln Pro Gly Ala Glu Leu Val Lys Pro Gly Ala
1               5                   10                  15

Ser Val Lys Met Ser Cys Lys Ala Ser Gly Tyr Thr Phe Thr Ser Tyr
            20                  25                  30

Asn Met His Trp Val Lys Gln Thr Pro Gly Arg Gly Leu Glu Trp Ile
        35                  40                  45

Gly Ala Ile Tyr Pro Gly Asn Gly Asp Thr Ser Tyr Asn Gln Lys Phe
    50                  55                  60

Lys Gly Lys Ala Thr Leu Thr Ala Asp Lys Ser Ser Ser Thr Ala Tyr

```
                65                  70                  75                  80
Met Gln Leu Ser Ser Leu Thr Ser Glu Asp Ser Ala Val Tyr Tyr Cys
                    85                  90                  95

Ala Arg Ser Thr Tyr Tyr Gly Gly Asp Trp Tyr Phe Asn Val Trp Gly
                100                 105                 110

Ala Gly Thr Thr Val Thr Val Ser Ala
        115                 120
```

<210> SEQ ID NO 17
<211> LENGTH: 990
<212> TYPE: DNA
<213> ORGANISM: Artificial
<220> FEATURE:
<223> OTHER INFORMATION: Generic IgG1 constant region

<400> SEQUENCE: 17

```
gccagcacta aaggaccatc agtatttccc cttgcacctt catctaagag tacttctggt      60
ggaactgcag ctttgggttg cttagtgaag gattatttcc ctgagcctgt tactgtttct     120
tggaattctg gtgcccttac ttctggtgtt catactttcc ctgcagtctt acaaagcagt     180
ggtttgtatt ccctgagcag tgttgtaact gttccatctt caagtctagg tacccagacc     240
tacatctgta atgtcaacca caagcccagc aatactaagg tcgataagaa ggttgagccc     300
aagtcatgtg ataagacaca tacttgtcca ccttgtccag ctccagaatt gttgggcgga     360
ccatctgttt ttttgttccc acccaagcct aaagataccc tcatgatatc cagaaccccct    420
gaagttacat gcgtagttgt agacgttagt catgaggatc ctgaggtcaa gtttaattgg     480
tatgtggatg gagtggaagt gcataatgca agacaaagc caagagagga gcagtacaac      540
tcaacataca gagtggtatc agtgctgact gttcttcacc aagattggct gaatgggaaa     600
gagtataagt gcaaggtgtc taataaggct ttaccagctc ccatcgaaaa gaccattagc     660
aaggctaaag acaaccaag agagcctcaa gtatatacac ttcctccatc ccgtgatgaa      720
ttgactaaga accaggtttc tctcacatgt ctagtgaagg ggttttaccc atctgacatt     780
gctgttgaat gggaaagcaa tggccagcct gaaaataact ataagaccac accacctgtt     840
ctagacagtg atggatcctt tttcctgtac tccaagctca cagtagacaa atctagatgg     900
caacaaggga acgtgttttc atgcagtgtt atgcatgaag cccttcacaa ccactataca     960
cagaagtcac tgagtctctc acctggtaag                                      990
```

<210> SEQ ID NO 18
<211> LENGTH: 330
<212> TYPE: PRT
<213> ORGANISM: Artificial
<220> FEATURE:
<223> OTHER INFORMATION: Generic IgG1 constant region

<400> SEQUENCE: 18

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80
```

```
Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
        210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 19
<211> LENGTH: 110
<212> TYPE: PRT
<213> ORGANISM: Homo sapiens

<400> SEQUENCE: 19

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys
            100                 105                 110
```

<210> SEQ ID NO 20
<211> LENGTH: 328
<212> TYPE: PRT
<213> ORGANISM: Homo sapiens

<400> SEQUENCE: 20

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro
                325
```

<210> SEQ ID NO 21
<211> LENGTH: 857
<212> TYPE: PRT
<213> ORGANISM: Leishmania major

<400> SEQUENCE: 21

Met Gly Lys Arg Lys Gly Asn Ser Leu Gly Asp Ser Gly Ser Ala Ala

-continued

```
1               5                   10                  15
Thr Ala Ser Arg Glu Ala Ser Ala Gln Ala Glu Asp Ala Ala Ser Gln
                20                  25                  30
Thr Lys Thr Ala Ser Pro Pro Ala Lys Val Ile Leu Leu Pro Lys Thr
                35                  40                  45
Leu Thr Asp Glu Lys Asp Phe Ile Gly Ile Phe Pro Phe Pro Phe Trp
 50                  55                  60
Pro Val His Phe Val Leu Thr Val Val Ala Leu Phe Val Leu Ala Ala
 65                  70                  75                  80
Ser Cys Phe Gln Ala Phe Thr Val Arg Met Ile Ser Val Gln Ile Tyr
                85                  90                  95
Gly Tyr Leu Ile His Glu Phe Asp Pro Trp Phe Asn Tyr Arg Ala Ala
                100                 105                 110
Glu Tyr Met Ser Thr His Gly Trp Ser Ala Phe Phe Ser Trp Phe Asp
                115                 120                 125
Tyr Met Ser Trp Tyr Pro Leu Gly Arg Pro Val Gly Ser Thr Thr Tyr
                130                 135                 140
Pro Gly Leu Gln Leu Thr Ala Val Ala Ile His Arg Ala Leu Ala Ala
145                 150                 155                 160
Ala Gly Met Pro Met Ser Leu Asn Asn Val Cys Val Leu Met Pro Ala
                165                 170                 175
Trp Phe Gly Ala Ile Ala Thr Ala Thr Leu Ala Phe Cys Thr Tyr Glu
                180                 185                 190
Ala Ser Gly Ser Thr Val Ala Ala Ala Ala Ala Leu Ser Phe Ser
                195                 200                 205
Ile Ile Pro Ala His Leu Met Arg Ser Met Ala Gly Glu Phe Asp Asn
                210                 215                 220
Glu Cys Ile Ala Val Ala Ala Met Leu Leu Thr Phe Tyr Cys Trp Val
225                 230                 235                 240
Arg Ser Leu Arg Thr Arg Ser Ser Trp Pro Ile Gly Val Leu Thr Gly
                245                 250                 255
Val Ala Tyr Gly Tyr Met Ala Ala Ala Trp Gly Gly Tyr Ile Phe Val
                260                 265                 270
Leu Asn Met Val Ala Met His Ala Gly Ile Ser Ser Met Val Asp Trp
                275                 280                 285
Ala Arg Asn Thr Tyr Asn Pro Ser Leu Leu Arg Ala Tyr Thr Leu Phe
                290                 295                 300
Tyr Val Val Gly Thr Ala Ile Ala Val Cys Val Pro Pro Val Gly Met
305                 310                 315                 320
Ser Pro Phe Lys Ser Leu Glu Gln Leu Gly Ala Leu Leu Val Leu Val
                325                 330                 335
Phe Leu Cys Gly Leu Gln Val Cys Glu Val Leu Arg Ala Arg Ala Gly
                340                 345                 350
Val Glu Val Arg Ser Arg Ala Asn Phe Lys Ile Arg Val Arg Val Phe
                355                 360                 365
Ser Val Met Ala Gly Val Ala Ala Leu Ala Ile Ser Val Leu Ala Pro
                370                 375                 380
Thr Gly Tyr Phe Gly Pro Leu Ser Val Arg Val Arg Ala Leu Phe Val
385                 390                 395                 400
Glu His Thr Arg Thr Gly Asn Pro Leu Val Asp Ser Val Ala Glu His
                405                 410                 415
Gln Pro Ala Ser Pro Glu Ala Met Trp Ala Phe Leu His Val Cys Gly
                420                 425                 430
```

```
Val Thr Trp Gly Leu Gly Ser Ile Val Leu Ala Val Ser Thr Phe Val
        435                 440                 445

His Tyr Ser Pro Ser Lys Val Phe Trp Leu Leu Asn Ser Gly Ala Val
    450                 455                 460

Tyr Tyr Phe Ser Thr Arg Met Ala Arg Leu Leu Leu Leu Ser Gly Pro
465                 470                 475                 480

Ala Ala Cys Leu Ser Thr Gly Ile Phe Val Gly Thr Ile Leu Glu Ala
                485                 490                 495

Ala Val Gln Leu Ser Phe Trp Asp Ser Asp Ala Thr Lys Ala Lys Lys
            500                 505                 510

Gln Gln Lys Gln Ala Gln Arg His Gln Arg Gly Ala Gly Lys Gly Ser
        515                 520                 525

Gly Arg Asp Asp Ala Lys Asn Ala Thr Thr Ala Arg Ala Phe Cys Asp
    530                 535                 540

Val Phe Ala Gly Ser Ser Leu Ala Trp Gly His Arg Met Val Leu Ser
545                 550                 555                 560

Ile Ala Met Trp Ala Leu Val Thr Thr Ala Val Ser Phe Phe Ser
                565                 570                 575

Ser Glu Phe Ala Ser His Ser Thr Lys Phe Ala Glu Gln Ser Ser Asn
                580                 585                 590

Pro Met Ile Val Phe Ala Ala Val Gln Asn Arg Ala Thr Gly Lys
            595                 600                 605

Pro Met Asn Leu Leu Val Asp Asp Tyr Leu Lys Ala Tyr Glu Trp Leu
        610                 615                 620

Arg Asp Ser Thr Pro Glu Asp Ala Arg Val Leu Ala Trp Asp Tyr
625                 630                 635                 640

Gly Tyr Gln Ile Thr Gly Ile Gly Asn Arg Thr Ser Leu Ala Asp Gly
                645                 650                 655

Asn Thr Trp Asn His Glu His Ile Ala Thr Ile Gly Lys Met Leu Thr
                660                 665                 670

Ser Pro Val Val Glu Ala His Ser Leu Val Arg His Met Ala Asp Tyr
        675                 680                 685

Val Leu Ile Trp Ala Gly Gln Ser Gly Asp Leu Met Lys Ser Pro His
    690                 695                 700

Met Ala Arg Ile Gly Asn Ser Val Tyr His Asp Ile Cys Pro Asp Asp
705                 710                 715                 720

Pro Leu Cys Gln Gln Phe Gly Phe His Arg Asn Asp Tyr Ser Arg Pro
                725                 730                 735

Thr Pro Met Met Arg Ala Ser Leu Leu Tyr Asn Leu His Glu Ala Gly
                740                 745                 750

Lys Arg Lys Gly Val Lys Val Asn Pro Ser Leu Phe Gln Glu Val Tyr
        755                 760                 765

Ser Ser Lys Tyr Gly Leu Val Arg Ile Phe Lys Val Met Asn Val Ser
    770                 775                 780

Ala Glu Ser Lys Lys Trp Val Ala Asp Pro Ala Asn Arg Val Cys His
785                 790                 795                 800

Pro Pro Gly Ser Trp Ile Cys Pro Gly Gln Tyr Pro Ala Lys Glu
                805                 810                 815

Ile Gln Glu Met Leu Ala His Arg Val Pro Phe Asp Gln Val Thr Asn
            820                 825                 830

Ala Asp Arg Lys Asn Asn Val Gly Ser Tyr Gln Glu Glu Tyr Met Arg
        835                 840                 845
```

Arg Met Arg Glu Ser Glu Asn Arg Arg
    850                 855

<210> SEQ ID NO 22
<211> LENGTH: 866
<212> TYPE: PRT
<213> ORGANISM: artificial
<220> FEATURE:
<223> OTHER INFORMATION: His-tagged version of Leishmania major STT3-D
      gene with added amino acids

<400> SEQUENCE: 22

Met Gly Lys Arg Lys Gly Asn Ser Leu Gly Asp Ser Gly Ala Ala
1               5                   10                  15

Thr Ala Ser Arg Glu Ala Ser Ala Gln Ala Glu Asp Ala Ala Ser Gln
            20                  25                  30

Thr Lys Thr Ala Ser Pro Pro Ala Lys Val Ile Leu Leu Pro Lys Thr
            35                  40                  45

Leu Thr Asp Glu Lys Asp Phe Ile Gly Ile Phe Pro Phe Pro Phe Trp
    50                  55                  60

Pro Val His Phe Val Leu Thr Val Val Ala Leu Phe Val Leu Ala Ala
65                  70                  75                  80

Ser Cys Phe Gln Ala Phe Thr Val Arg Met Ile Ser Val Gln Ile Tyr
                85                  90                  95

Gly Tyr Leu Ile His Glu Phe Asp Pro Trp Phe Asn Tyr Arg Ala Ala
                100                 105                 110

Glu Tyr Met Ser Thr His Gly Trp Ser Ala Phe Phe Ser Trp Phe Asp
            115                 120                 125

Tyr Met Ser Trp Tyr Pro Leu Gly Arg Pro Val Gly Ser Thr Thr Tyr
    130                 135                 140

Pro Gly Leu Gln Leu Thr Ala Val Ala Ile His Arg Ala Leu Ala Ala
145                 150                 155                 160

Ala Gly Met Pro Met Ser Leu Asn Asn Val Cys Val Leu Met Pro Ala
                165                 170                 175

Trp Phe Gly Ala Ile Ala Thr Ala Thr Leu Ala Phe Cys Thr Tyr Glu
            180                 185                 190

Ala Ser Gly Ser Thr Val Ala Ala Ala Ala Ala Leu Ser Phe Ser
            195                 200                 205

Ile Ile Pro Ala His Leu Met Arg Ser Met Ala Gly Glu Phe Asp Asn
    210                 215                 220

Glu Cys Ile Ala Val Ala Ala Met Leu Leu Thr Phe Tyr Cys Trp Val
225                 230                 235                 240

Arg Ser Leu Arg Thr Arg Ser Ser Trp Pro Ile Gly Val Leu Thr Gly
                245                 250                 255

Val Ala Tyr Gly Tyr Met Ala Ala Ala Trp Gly Gly Tyr Ile Phe Val
            260                 265                 270

Leu Asn Met Val Ala Met His Ala Gly Ile Ser Ser Met Val Asp Trp
    275                 280                 285

Ala Arg Asn Thr Tyr Asn Pro Ser Leu Leu Arg Ala Tyr Thr Leu Phe
    290                 295                 300

Tyr Val Val Gly Thr Ala Ile Ala Val Cys Val Pro Pro Val Gly Met
305                 310                 315                 320

Ser Pro Phe Lys Ser Leu Glu Gln Leu Gly Ala Leu Leu Val Leu Val
                325                 330                 335

Phe Leu Cys Gly Leu Gln Val Cys Glu Val Leu Arg Ala Arg Ala Gly
            340                 345                 350

```
Val Glu Val Arg Ser Arg Ala Asn Phe Lys Ile Arg Val Phe
        355                 360                 365

Ser Val Met Ala Gly Val Ala Ala Leu Ala Ile Ser Val Leu Ala Pro
    370                 375                 380

Thr Gly Tyr Phe Gly Pro Leu Ser Val Arg Val Arg Ala Leu Phe Val
385                 390                 395                 400

Glu His Thr Arg Thr Gly Asn Pro Leu Val Asp Ser Val Ala Glu His
                405                 410                 415

Gln Pro Ala Ser Pro Glu Ala Met Trp Ala Phe Leu His Val Cys Gly
                420                 425                 430

Val Thr Trp Gly Leu Gly Ser Ile Val Leu Ala Val Ser Thr Phe Val
            435                 440                 445

His Tyr Ser Pro Ser Lys Val Phe Trp Leu Leu Asn Ser Gly Ala Val
            450                 455                 460

Tyr Tyr Phe Ser Thr Arg Met Ala Arg Leu Leu Leu Ser Gly Pro
465                 470                 475                 480

Ala Ala Cys Leu Ser Thr Gly Ile Phe Val Gly Thr Ile Leu Glu Ala
                485                 490                 495

Ala Val Gln Leu Ser Phe Trp Asp Ser Asp Ala Thr Lys Ala Lys Lys
                500                 505                 510

Gln Gln Lys Gln Ala Gln Arg His Gln Arg Gly Ala Gly Lys Gly Ser
                515                 520                 525

Gly Arg Asp Asp Ala Lys Asn Ala Thr Thr Ala Arg Ala Phe Cys Asp
    530                 535                 540

Val Phe Ala Gly Ser Ser Leu Ala Trp Gly His Arg Met Val Leu Ser
545                 550                 555                 560

Ile Ala Met Trp Ala Leu Val Thr Thr Thr Ala Val Ser Phe Phe Ser
                565                 570                 575

Ser Glu Phe Ala Ser His Ser Thr Lys Phe Ala Glu Gln Ser Ser Asn
                580                 585                 590

Pro Met Ile Val Phe Ala Ala Val Val Gln Asn Arg Ala Thr Gly Lys
        595                 600                 605

Pro Met Asn Leu Leu Val Asp Asp Tyr Leu Lys Ala Tyr Glu Trp Leu
        610                 615                 620

Arg Asp Ser Thr Pro Glu Asp Ala Arg Val Leu Ala Trp Trp Asp Tyr
625                 630                 635                 640

Gly Tyr Gln Ile Thr Gly Ile Gly Asn Arg Thr Ser Leu Ala Asp Gly
                645                 650                 655

Asn Thr Trp Asn His Glu His Ile Ala Thr Ile Gly Lys Met Leu Thr
                660                 665                 670

Ser Pro Val Val Glu Ala His Ser Leu Val Arg His Met Ala Asp Tyr
            675                 680                 685

Val Leu Ile Trp Ala Gly Gln Ser Gly Asp Leu Met Lys Ser Pro His
        690                 695                 700

Met Ala Arg Ile Gly Asn Ser Val Tyr His Asp Ile Cys Pro Asp Asp
705                 710                 715                 720

Pro Leu Cys Gln Gln Phe Gly Phe His Arg Asn Asp Tyr Ser Arg Pro
                725                 730                 735

Thr Pro Met Met Arg Ala Ser Leu Leu Tyr Asn Leu His Glu Ala Gly
            740                 745                 750

Lys Arg Lys Gly Val Lys Val Asn Pro Ser Leu Phe Gln Glu Val Tyr
        755                 760                 765
```

Ser Ser Lys Tyr Gly Leu Val Arg Ile Phe Lys Val Met Asn Val Ser
    770                 775                 780

Ala Glu Ser Lys Lys Trp Val Ala Asp Pro Ala Asn Arg Val Cys His
785                 790                 795                 800

Pro Pro Gly Ser Trp Ile Cys Pro Gly Gln Tyr Pro Pro Ala Lys Glu
                805                 810                 815

Ile Gln Glu Met Leu Ala His Arg Val Pro Phe Asp Gln Val Thr Asn
                820                 825                 830

Ala Asp Arg Lys Asn Val Gly Ser Tyr Gln Glu Tyr Met Arg
                835                 840                 845

Arg Met Arg Glu Ser Glu Asn Arg Arg Gly Ser Gly His His His His
850                 855                 860

His His
865

<210> SEQ ID NO 23
<211> LENGTH: 110
<212> TYPE: PRT
<213> ORGANISM: Homo sapiens

<400> SEQUENCE: 23

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
                20                  25                  30

Val Val Asp Val Ser His Glu Asp Pro Glu Val Lys Phe Asn Trp Tyr
            35                  40                  45

Val Asp Gly Val Glu Val His Asn Ala Lys Thr Lys Pro Arg Glu Glu
        50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys
                100                 105                 110

<210> SEQ ID NO 24
<211> LENGTH: 110
<212> TYPE: PRT
<213> ORGANISM: Homo sapiens

<400> SEQUENCE: 24

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
                20                  25                  30

Val Val Asp Val Ser His Glu Asp Pro Glu Val Lys Phe Asn Trp Tyr
            35                  40                  45

Val Asp Gly Val Glu Val His Asn Ala Lys Thr Lys Pro Arg Glu Glu
        50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys
                100                 105                 110

<210> SEQ ID NO 25
<211> LENGTH: 110
<212> TYPE: PRT
<213> ORGANISM: Homo sapiens

<400> SEQUENCE: 25

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys
            100                 105                 110

<210> SEQ ID NO 26
<211> LENGTH: 109
<212> TYPE: PRT
<213> ORGANISM: Homo sapiens

<400> SEQUENCE: 26

Ala Pro Pro Val Ala Gly Pro Ser Val Phe Leu Phe Pro Lys Pro
1               5                   10                  15

Lys Asp Thr Leu Met Ile Ser Arg Thr Pro Glu Val Thr Cys Val Val
            20                  25                  30

Val Asp Val Ser His Glu Asp Pro Glu Val Gln Phe Asn Trp Tyr Val
        35                  40                  45

Asp Gly Val Glu Val His Asn Ala Lys Thr Lys Pro Arg Glu Glu Gln
    50                  55                  60

Phe Asn Ser Thr Phe Arg Val Val Ser Val Leu Thr Val Val His Gln
65                  70                  75                  80

Asp Trp Leu Asn Gly Lys Glu Tyr Lys Cys Lys Val Ser Asn Lys Gly
                85                  90                  95

Leu Pro Ala Pro Ile Glu Lys Thr Ile Ser Lys Thr Lys
            100                 105

<210> SEQ ID NO 27
<211> LENGTH: 109
<212> TYPE: PRT
<213> ORGANISM: Homo sapiens

<400> SEQUENCE: 27

Ala Pro Pro Val Ala Gly Pro Ser Val Phe Leu Phe Pro Lys Pro
1               5                   10                  15

Lys Asp Thr Leu Met Ile Ser Arg Thr Pro Glu Val Thr Cys Val Val
            20                  25                  30

Val Asp Val Ser His Glu Asp Pro Glu Val Gln Phe Asn Trp Tyr Val
        35                  40                  45

Asp Gly Met Glu Val His Asn Ala Lys Thr Lys Pro Arg Glu Glu Gln
    50                  55                  60

Phe Asn Ser Thr Phe Arg Val Val Ser Val Leu Thr Val Val His Gln

```
                65                  70                  75                  80
Asp Trp Leu Asn Gly Lys Glu Tyr Lys Cys Lys Val Ser Asn Lys Gly
                    85                  90                  95
Leu Pro Ala Pro Ile Glu Lys Thr Ile Ser Lys Thr Lys
                100                 105
```

<210> SEQ ID NO 28
<211> LENGTH: 109
<212> TYPE: PRT
<213> ORGANISM: Homo sapiens

<400> SEQUENCE: 28

```
Ala Pro Pro Val Ala Gly Pro Ser Val Phe Leu Phe Pro Pro Lys Pro
1               5                   10                  15
Lys Asp Thr Leu Met Ile Ser Arg Thr Pro Glu Val Thr Cys Val Val
                20                  25                  30
Val Asp Val Ser His Glu Asp Pro Glu Val Gln Phe Asn Trp Tyr Val
                35                  40                  45
Asp Gly Val Glu Val His Asn Ala Lys Thr Lys Pro Arg Glu Glu Gln
            50                  55                  60
Phe Asn Ser Thr Phe Arg Val Val Ser Val Leu Thr Val Val His Gln
65                  70                  75                  80
Asp Trp Leu Asn Gly Lys Glu Tyr Lys Cys Lys Val Ser Asn Lys Gly
                    85                  90                  95
Leu Pro Ala Pro Ile Glu Lys Thr Ile Ser Lys Thr Lys
                100                 105
```

<210> SEQ ID NO 29
<211> LENGTH: 109
<212> TYPE: PRT
<213> ORGANISM: Homo sapiens

<400> SEQUENCE: 29

```
Ala Pro Pro Val Ala Gly Pro Ser Val Phe Leu Phe Pro Pro Lys Pro
1               5                   10                  15
Lys Asp Thr Leu Met Ile Ser Arg Thr Pro Glu Val Thr Cys Val Val
                20                  25                  30
Val Asp Val Ser His Glu Asp Pro Glu Val Gln Phe Asn Trp Tyr Val
                35                  40                  45
Asp Gly Val Glu Val His Asn Ala Lys Thr Lys Pro Arg Glu Glu Gln
            50                  55                  60
Phe Asn Ser Thr Phe Arg Val Val Ser Val Leu Thr Val Val His Gln
65                  70                  75                  80
Asp Trp Leu Asn Gly Lys Glu Tyr Lys Cys Lys Val Ser Asn Lys Gly
                    85                  90                  95
Leu Pro Ala Pro Ile Glu Lys Thr Ile Ser Lys Thr Lys
                100                 105
```

<210> SEQ ID NO 30
<211> LENGTH: 109
<212> TYPE: PRT
<213> ORGANISM: Homo sapiens

<400> SEQUENCE: 30

```
Ala Pro Pro Val Ala Gly Pro Ser Val Phe Leu Phe Pro Pro Lys Pro
1               5                   10                  15
Lys Asp Thr Leu Met Ile Ser Arg Thr Pro Glu Val Thr Cys Val Val
                20                  25                  30
```

Val Asp Val Ser His Glu Asp Pro Glu Val Gln Phe Asn Trp Tyr Val
            35                  40                  45

Asp Gly Val Glu Val His Asn Ala Lys Thr Lys Pro Arg Glu Glu Gln
        50                  55                  60

Phe Asn Ser Thr Phe Arg Val Val Ser Val Leu Thr Val His Gln
65                  70                  75                  80

Asp Trp Leu Asn Gly Lys Glu Tyr Lys Cys Lys Val Ser Asn Lys Gly
                85                  90                  95

Leu Pro Ala Pro Ile Glu Lys Thr Ile Ser Lys Thr Lys
            100                 105

<210> SEQ ID NO 31
<211> LENGTH: 109
<212> TYPE: PRT
<213> ORGANISM: Homo sapiens

<400> SEQUENCE: 31

Ala Pro Pro Val Ala Gly Pro Ser Val Phe Leu Phe Pro Pro Lys Pro
1               5                   10                  15

Lys Asp Thr Leu Met Ile Ser Arg Thr Pro Glu Val Thr Cys Val Val
            20                  25                  30

Val Asp Val Ser His Glu Asp Pro Glu Val Gln Phe Asn Trp Tyr Val
            35                  40                  45

Asp Gly Val Glu Val His Asn Ala Lys Thr Lys Pro Arg Glu Glu Gln
        50                  55                  60

Phe Asn Ser Thr Phe Arg Val Val Ser Val Leu Thr Val Val His Gln
65                  70                  75                  80

Asp Trp Leu Asn Gly Lys Glu Tyr Lys Cys Lys Val Ser Asn Lys Gly
                85                  90                  95

Leu Pro Ala Pro Ile Glu Lys Thr Ile Ser Lys Thr Lys
            100                 105

<210> SEQ ID NO 32
<211> LENGTH: 110
<212> TYPE: PRT
<213> ORGANISM: Homo sapiens

<400> SEQUENCE: 32

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Gln Phe Lys Trp Tyr
            35                  40                  45

Val Asp Gly Val Glu Val His Asn Ala Lys Thr Lys Pro Arg Glu Glu
        50                  55                  60

Gln Tyr Asn Ser Thr Phe Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Thr Lys
            100                 105                 110

<210> SEQ ID NO 33
<211> LENGTH: 110
<212> TYPE: PRT
<213> ORGANISM: Homo sapiens

<400> SEQUENCE: 33

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Gln Phe Lys Trp Tyr
        35                  40                  45

Val Asp Gly Val Glu Val His Asn Ala Lys Thr Lys Pro Arg Glu Glu
    50                  55                  60

Gln Tyr Asn Ser Thr Phe Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Thr Lys
            100                 105                 110

<210> SEQ ID NO 34
<211> LENGTH: 110
<212> TYPE: PRT
<213> ORGANISM: Homo sapiens

<400> SEQUENCE: 34

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Gln Phe Lys Trp Tyr
        35                  40                  45

Val Asp Gly Val Glu Val His Asn Ala Lys Thr Lys Pro Arg Glu Glu
    50                  55                  60

Gln Tyr Asn Ser Thr Phe Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Thr Lys
            100                 105                 110

<210> SEQ ID NO 35
<211> LENGTH: 110
<212> TYPE: PRT
<213> ORGANISM: Homo sapiens

<400> SEQUENCE: 35

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Gln Phe Lys Trp Tyr
        35                  40                  45

Val Asp Gly Val Glu Val His Asn Ala Lys Thr Lys Pro Arg Glu Glu
    50                  55                  60

Gln Tyr Asn Ser Thr Phe Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

```
Ala Leu Pro Ala Pro Ile Glu Lys Thr Ile Ser Lys Thr Lys
            100                 105                 110
```

<210> SEQ ID NO 36
<211> LENGTH: 110
<212> TYPE: PRT
<213> ORGANISM: Homo sapiens
<400> SEQUENCE: 36

```
Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Gln Phe Lys Trp Tyr
        35                  40                  45

Val Asp Gly Val Glu Val His Asn Ala Lys Thr Lys Pro Arg Glu Glu
    50                  55                  60

Gln Tyr Asn Ser Thr Phe Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Thr Lys
            100                 105                 110
```

<210> SEQ ID NO 37
<211> LENGTH: 110
<212> TYPE: PRT
<213> ORGANISM: Homo sapiens
<400> SEQUENCE: 37

```
Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Gln Phe Lys Trp Tyr
        35                  40                  45

Val Asp Gly Val Glu Val His Asn Ala Lys Thr Lys Pro Arg Glu Glu
    50                  55                  60

Gln Tyr Asn Ser Thr Phe Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Thr Lys
            100                 105                 110
```

<210> SEQ ID NO 38
<211> LENGTH: 110
<212> TYPE: PRT
<213> ORGANISM: Homo sapiens
<400> SEQUENCE: 38

```
Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Gln Phe Lys Trp Tyr
        35                  40                  45

Val Asp Gly Val Glu Val His Asn Ala Lys Thr Lys Pro Arg Glu Glu
```

```
                    50                  55                  60

Gln Tyr Asn Ser Thr Phe Arg Val Val Ser Val Leu Thr Val Leu His
 65                  70                  75                  80

Gln Asp Trp Leu Asn Gly Lys Glu Tyr Lys Cys Lys Val Ser Asn Lys
                     85                  90                  95

Ala Leu Pro Ala Pro Ile Glu Lys Thr Ile Ser Lys Thr Lys
                100                 105                 110
```

<210> SEQ ID NO 39
<211> LENGTH: 110
<212> TYPE: PRT
<213> ORGANISM: Homo sapiens

<400> SEQUENCE: 39

```
Ala Pro Glu Leu Leu Gly Gly Pro Ser Val Phe Leu Phe Pro Pro Lys
  1                   5                  10                  15

Pro Lys Asp Thr Leu Met Ile Ser Arg Thr Pro Glu Val Thr Cys Val
                     20                  25                  30

Val Val Asp Val Ser His Glu Asp Pro Glu Val Gln Phe Lys Trp Tyr
                 35                  40                  45

Val Asp Gly Val Glu Val His Asn Ala Lys Thr Lys Pro Arg Glu Glu
             50                  55                  60

Gln Tyr Asn Ser Thr Phe Arg Val Val Ser Val Leu Thr Val Val His
 65                  70                  75                  80

Gln Asp Trp Leu Asn Gly Lys Glu Tyr Lys Cys Lys Val Ser Asn Lys
                     85                  90                  95

Ala Leu Pro Ala Pro Ile Glu Lys Thr Ile Ser Lys Thr Lys
                100                 105                 110
```

<210> SEQ ID NO 40
<211> LENGTH: 109
<212> TYPE: PRT
<213> ORGANISM: Homo sapiens

<400> SEQUENCE: 40

```
Ala Pro Glu Leu Leu Gly Gly Pro Ser Val Phe Leu Phe Pro Pro Lys
  1                   5                  10                  15

Pro Lys Asp Thr Leu Met Ile Ser Arg Thr Pro Glu Val Thr Cys Val
                     20                  25                  30

Val Val Asp Val Ser His Glu Asp Pro Glu Val Gln Phe Lys Trp Tyr
                 35                  40                  45

Val Asp Gly Val Glu Val His Asn Ala Lys Thr Lys Pro Arg Glu Glu
             50                  55                  60

Gln Tyr Asn Ser Thr Phe Arg Val Val Ser Val Leu Thr Val Leu His
 65                  70                  75                  80

Gln Asp Trp Leu Asn Gly Lys Glu Tyr Lys Cys Lys Val Ser Asn Lys
                     85                  90                  95

Ala Leu Pro Ala Pro Ile Glu Lys Thr Ile Ser Lys Thr
                100                 105
```

<210> SEQ ID NO 41
<211> LENGTH: 110
<212> TYPE: PRT
<213> ORGANISM: Homo sapiens

<400> SEQUENCE: 41

```
Ala Pro Glu Leu Leu Gly Gly Pro Ser Val Phe Leu Phe Pro Pro Lys
  1                   5                  10                  15
```

```
Pro Lys Asp Thr Leu Met Ile Ser Arg Thr Pro Glu Val Thr Cys Val
            20                  25                  30

Val Val Asp Val Ser His Glu Asp Pro Glu Val Gln Phe Lys Trp Tyr
        35                  40                  45

Val Asp Gly Val Glu Val His Asn Ala Lys Thr Lys Pro Arg Glu Glu
    50                  55                  60

Gln Phe Asn Ser Thr Phe Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Thr Lys
                100                 105                 110

<210> SEQ ID NO 42
<211> LENGTH: 110
<212> TYPE: PRT
<213> ORGANISM: Homo sapiens

<400> SEQUENCE: 42

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Gln Phe Lys Trp Tyr
        35                  40                  45

Val Asp Gly Val Glu Val His Asn Ala Lys Thr Lys Pro Arg Glu Glu
    50                  55                  60

Gln Phe Asn Ser Thr Phe Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Thr Lys
                100                 105                 110

<210> SEQ ID NO 43
<211> LENGTH: 110
<212> TYPE: PRT
<213> ORGANISM: Homo sapiens

<400> SEQUENCE: 43

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Gln Phe Lys Trp Tyr
        35                  40                  45

Val Asp Gly Val Glu Val His Asn Ala Lys Thr Lys Pro Arg Glu Glu
    50                  55                  60

Gln Tyr Asn Ser Thr Phe Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Thr Lys
                100                 105                 110

<210> SEQ ID NO 44
```

```
<211> LENGTH: 110
<212> TYPE: PRT
<213> ORGANISM: Homo sapiens

<400> SEQUENCE: 44

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Gln Phe Lys Trp Tyr
        35                  40                  45

Val Asp Gly Val Glu Val His Asn Ala Lys Thr Lys Leu Arg Glu Glu
    50                  55                  60

Gln Tyr Asn Ser Thr Phe Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Thr Lys
            100                 105                 110

<210> SEQ ID NO 45
<211> LENGTH: 110
<212> TYPE: PRT
<213> ORGANISM: Homo sapiens

<400> SEQUENCE: 45

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Gln Phe Lys Trp Tyr
        35                  40                  45

Val Asp Gly Val Glu Val His Asn Ala Lys Thr Lys Leu Arg Glu Glu
    50                  55                  60

Gln Tyr Asn Ser Thr Phe Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Thr Lys
            100                 105                 110

<210> SEQ ID NO 46
<211> LENGTH: 110
<212> TYPE: PRT
<213> ORGANISM: Homo sapiens

<400> SEQUENCE: 46

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Gln Phe Lys Trp Tyr
        35                  40                  45

Val Asp Gly Val Glu Val His Asn Ala Lys Thr Lys Leu Arg Glu Glu
    50                  55                  60

Gln Tyr Asn Ser Thr Phe Arg Val Val Ser Val Leu Thr Val Leu His
65                  70                  75                  80
```

```
Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys
            100                 105                 110

<210> SEQ ID NO 47
<211> LENGTH: 110
<212> TYPE: PRT
<213> ORGANISM: Homo sapiens

<400> SEQUENCE: 47

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Gln Phe Lys Trp Tyr
        35                  40                  45

Val Asp Gly Val Glu Val His Asn Ala Lys Thr Lys Pro Arg Glu Glu
    50                  55                  60

Gln Tyr Asn Ser Thr Phe Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Thr Lys
            100                 105                 110

<210> SEQ ID NO 48
<211> LENGTH: 110
<212> TYPE: PRT
<213> ORGANISM: Homo sapiens

<400> SEQUENCE: 48

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Gln Phe Lys Trp Tyr
        35                  40                  45

Val Asp Gly Val Glu Val His Asn Ala Lys Thr Lys Pro Trp Glu Glu
    50                  55                  60

Gln Tyr Asn Ser Thr Phe Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Thr Lys
            100                 105                 110

<210> SEQ ID NO 49
<211> LENGTH: 110
<212> TYPE: PRT
<213> ORGANISM: Homo sapiens

<400> SEQUENCE: 49

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Gln Phe Lys Trp Tyr
```

```
                35                  40                  45
Val Asp Gly Val Glu Val His Asn Ala Lys Thr Lys Pro Trp Glu Glu
 50                  55                  60

Gln Tyr Asn Ser Thr Phe Arg Val Val Ser Val Leu Thr Val Leu His
 65                  70                  75                  80

Gln Asp Trp Leu Asn Gly Lys Glu Tyr Lys Cys Lys Val Ser Asn Lys
                 85                  90                  95

Ala Leu Pro Ala Pro Ile Glu Lys Thr Ile Ser Lys Thr Lys
            100                 105                 110
```

<210> SEQ ID NO 50
<211> LENGTH: 110
<212> TYPE: PRT
<213> ORGANISM: Homo sapiens

<400> SEQUENCE: 50

```
Ala Pro Glu Phe Leu Gly Gly Pro Ser Val Phe Leu Phe Pro Pro Lys
  1               5                  10                  15

Pro Lys Asp Thr Leu Met Ile Ser Arg Thr Pro Glu Val Thr Cys Val
                 20                  25                  30

Val Val Asp Val Ser Gln Glu Asp Pro Glu Val Gln Phe Asn Trp Tyr
             35                  40                  45

Val Asp Gly Val Glu Val His Asn Ala Lys Thr Lys Pro Arg Glu Glu
 50                  55                  60

Gln Phe Asn Ser Thr Tyr Arg Val Val Ser Val Leu Thr Val Leu His
 65                  70                  75                  80

Gln Asp Trp Leu Asn Gly Lys Glu Tyr Lys Cys Lys Val Ser Asn Lys
                 85                  90                  95

Gly Leu Pro Ser Ser Ile Glu Lys Thr Ile Ser Lys Ala Lys
            100                 105                 110
```

<210> SEQ ID NO 51
<211> LENGTH: 110
<212> TYPE: PRT
<213> ORGANISM: Homo sapiens

<400> SEQUENCE: 51

```
Ala Pro Glu Phe Leu Gly Gly Pro Ser Val Phe Leu Phe Pro Pro Lys
  1               5                  10                  15

Pro Lys Asp Thr Leu Met Ile Ser Arg Thr Pro Glu Val Thr Cys Val
                 20                  25                  30

Val Val Asp Val Ser Gln Glu Asp Pro Glu Val Gln Phe Asn Trp Tyr
             35                  40                  45

Val Asp Gly Val Glu Val His Asn Ala Lys Thr Lys Pro Arg Glu Glu
 50                  55                  60

Gln Phe Asn Ser Thr Tyr Arg Val Val Ser Val Leu Thr Val Val His
 65                  70                  75                  80

Gln Asp Trp Leu Asn Gly Lys Glu Tyr Lys Cys Lys Val Ser Asn Lys
                 85                  90                  95

Gly Leu Pro Ser Ser Ile Glu Lys Thr Ile Ser Lys Ala Lys
            100                 105                 110
```

<210> SEQ ID NO 52
<211> LENGTH: 110
<212> TYPE: PRT
<213> ORGANISM: Homo sapiens

<400> SEQUENCE: 52

Ala Pro Glu Phe Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser Gln Glu Asp Pro Glu Val Gln Phe Asn Trp Tyr
        35                  40                  45

Val Asp Gly Val Glu Val His Asn Ala Lys Thr Lys Pro Arg Glu Glu
    50                  55                  60

Gln Phe Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Gly Leu Pro Ser Ser Ile Glu Lys Thr Ile Ser Lys Ala Lys
            100                 105                 110

<210> SEQ ID NO 53
<211> LENGTH: 110
<212> TYPE: PRT
<213> ORGANISM: Homo sapiens

<400> SEQUENCE: 53

Ala Pro Glu Phe Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser Gln Glu Asp Pro Glu Val Gln Phe Asn Trp Tyr
        35                  40                  45

Val Asp Gly Val Glu Val His Asn Ala Lys Thr Lys Pro Arg Glu Glu
    50                  55                  60

Gln Phe Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Gly Leu Pro Ser Ser Ile Glu Lys Thr Ile Ser Lys Ala Lys
            100                 105                 110

<210> SEQ ID NO 54
<211> LENGTH: 110
<212> TYPE: PRT
<213> ORGANISM: Homo sapiens

<400> SEQUENCE: 54

Ala Pro Asn Leu Leu Gly Gly Pro Ser Val Phe Ile Phe Pro Pro Lys
1               5                   10                  15

Ile Lys Asp Val Leu Met Ile Ser Leu Ser Pro Ile Val Thr Cys Val
            20                  25                  30

Val Val Asp Val Ser Glu Asp Asp Pro Asp Val Gln Ile Ser Trp Phe
        35                  40                  45

Val Asn Asn Val Glu Val His Thr Ala Gln Thr Gln Thr His Arg Glu
    50                  55                  60

Asp Tyr Asn Ser Thr Leu Arg Val Val Ser Ala Leu Pro Ile Gln His
65                  70                  75                  80

Gln Asp Trp Met Ser Gly Lys Glu Phe Lys Cys Lys Val Asn Asn Lys
                85                  90                  95

Asp Leu Pro Ala Pro Ile Glu Arg Thr Ile Ser Lys Pro Lys
            100                 105                 110

<210> SEQ ID NO 55
<211> LENGTH: 328
<212> TYPE: PRT
<213> ORGANISM: Homo sapiens

<400> SEQUENCE: 55

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro
                325
```

<210> SEQ ID NO 56
<211> LENGTH: 328
<212> TYPE: PRT
<213> ORGANISM: Homo sapiens

<400> SEQUENCE: 56

```
Ala Ser Thr Lys Gly Pro Ser Val Phe Pro Leu Ala Pro Ser Ser Lys
  1               5                  10                  15

Ser Thr Ser Gly Gly Thr Ala Ala Leu Gly Cys Leu Val Lys Asp Tyr
             20                  25                  30

Phe Pro Glu Pro Val Thr Val Ser Trp Asn Ser Gly Ala Leu Thr Ser
         35                  40                  45

Gly Val His Thr Phe Pro Ala Val Leu Gln Ser Ser Gly Leu Tyr Ser
     50                  55                  60

Leu Ser Ser Val Val Thr Val Pro Ser Ser Leu Gly Thr Gln Thr
65                   70                  75                  80

Tyr Ile Cys Asn Val Asn His Lys Pro Ser Asn Thr Lys Val Asp Lys
                 85                  90                  95

Arg Val Glu Pro Lys Ser Cys Asp Lys Thr His Thr Cys Pro Pro Cys
             100                 105                 110

Pro Ala Pro Glu Leu Leu Gly Gly Pro Ser Val Phe Leu Phe Pro Pro
         115                 120                 125

Lys Pro Lys Asp Thr Leu Met Ile Ser Arg Thr Pro Glu Val Thr Cys
     130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                 165                 170                 175

Glu Gln Tyr Asn Ser Thr Tyr Arg Val Val Ser Val Leu Thr Val Leu
             180                 185                 190

His Gln Asp Trp Leu Asn Gly Lys Glu Tyr Lys Cys Lys Val Ser Asn
         195                 200                 205

Lys Ala Leu Pro Ala Pro Ile Glu Lys Thr Ile Ser Lys Ala Lys Gly
     210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                 245                 250                 255

Pro Ser Asp Ile Ala Val Glu Trp Glu Ser Asn Gly Gln Pro Glu Asn
             260                 265                 270

Asn Tyr Lys Thr Thr Pro Pro Val Leu Asp Ser Asp Gly Ser Phe Phe
         275                 280                 285

Leu Tyr Ser Lys Leu Thr Val Asp Lys Ser Arg Trp Gln Gln Gly Asn
     290                 295                 300

Val Phe Ser Cys Ser Val Met His Glu Ala Leu His Asn His Tyr Thr
305                 310                 315                 320

Gln Lys Ser Leu Ser Leu Ser Pro
                 325

<210> SEQ ID NO 57
<211> LENGTH: 328
<212> TYPE: PRT
<213> ORGANISM: Homo sapiens

<400> SEQUENCE: 57

Ala Ser Thr Lys Gly Pro Ser Val Phe Pro Leu Ala Pro Ser Ser Lys
  1               5                  10                  15

Ser Thr Ser Gly Gly Thr Ala Ala Leu Gly Cys Leu Val Lys Asp Tyr
             20                  25                  30

Phe Pro Glu Pro Val Thr Val Ser Trp Asn Ser Gly Ala Leu Thr Ser
```

```
            35                  40                  45
Gly Val His Thr Phe Pro Ala Val Leu Gln Ser Ser Gly Leu Tyr Ser
         50                  55                  60
Leu Ser Ser Val Val Thr Val Pro Ser Ser Leu Gly Thr Gln Thr
 65                  70                  75                  80
Tyr Ile Cys Asn Val Asn His Lys Pro Ser Asn Thr Lys Val Asp Lys
                 85                  90                  95
Lys Val Glu Pro Lys Ser Cys Asp Lys Thr His Thr Cys Pro Pro Cys
                100                 105                 110
Pro Ala Pro Glu Leu Leu Gly Gly Pro Ser Val Phe Leu Phe Pro Pro
                115                 120                 125
Lys Pro Lys Asp Thr Leu Met Ile Ser Arg Thr Pro Glu Val Thr Cys
            130                 135                 140
Val Val Val Asp Val Ser His Glu Asp Pro Glu Val Lys Phe Asn Trp
145                 150                 155                 160
Tyr Val Asp Gly Val Glu Val His Asn Ala Lys Thr Lys Pro Arg Glu
                165                 170                 175
Glu Gln Tyr Asn Ser Thr Tyr Arg Val Val Ser Val Leu Thr Val Leu
            180                 185                 190
His Gln Asp Trp Leu Asn Gly Lys Glu Tyr Lys Cys Lys Val Ser Asn
        195                 200                 205
Lys Ala Leu Pro Ala Pro Ile Glu Lys Thr Ile Ser Lys Ala Lys Gly
210                 215                 220
Gln Pro Arg Glu Pro Gln Val Tyr Thr Leu Pro Pro Ser Arg Asp Glu
225                 230                 235                 240
Leu Thr Lys Asn Gln Val Ser Leu Thr Cys Leu Val Lys Gly Phe Tyr
                245                 250                 255
Pro Ser Asp Ile Ala Val Glu Trp Glu Ser Asn Gly Gln Pro Glu Asn
            260                 265                 270
Asn Tyr Lys Thr Thr Pro Pro Val Leu Asp Ser Asp Gly Ser Phe Phe
        275                 280                 285
Leu Tyr Ser Lys Leu Thr Val Asp Lys Ser Arg Trp Gln Gln Gly Asn
    290                 295                 300
Ile Phe Ser Cys Ser Val Met His Glu Ala Leu His Asn His Tyr Thr
305                 310                 315                 320
Gln Lys Ser Leu Ser Leu Ser Pro
                325

<210> SEQ ID NO 58
<211> LENGTH: 324
<212> TYPE: PRT
<213> ORGANISM: Homo sapiens

<400> SEQUENCE: 58

Ala Ser Thr Lys Gly Pro Ser Val Phe Pro Leu Ala Pro Cys Ser Arg
 1               5                  10                  15
Ser Thr Ser Glu Ser Thr Ala Ala Leu Gly Cys Leu Val Lys Asp Tyr
                20                  25                  30
Phe Pro Glu Pro Val Thr Val Ser Trp Asn Ser Gly Ala Leu Thr Ser
            35                  40                  45
Gly Val His Thr Phe Pro Ala Val Leu Gln Ser Ser Gly Leu Tyr Ser
         50                  55                  60
Leu Ser Ser Val Val Thr Val Pro Ser Ser Asn Phe Gly Thr Gln Thr
 65                  70                  75                  80
```

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
            115                 120                 125

Thr Leu Met Ile Ser Arg Thr Pro Glu Val Thr Cys Val Val Val Asp
130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
            195                 200                 205

Ala Pro Ile Glu Lys Thr Ile Ser Lys Thr Lys Gly Gln Pro Arg Glu
            210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
            275                 280                 285

Leu Thr Val Asp Lys Ser Arg Trp Gln Gln Gly Asn Val Phe Ser Cys
290                 295                 300

Ser Val Met His Glu Ala Leu His Asn His Tyr Thr Gln Lys Ser Leu
305                 310                 315                 320

Ser Leu Ser Pro

<210> SEQ ID NO 59
<211> LENGTH: 324
<212> TYPE: PRT
<213> ORGANISM: Homo sapiens

<400> SEQUENCE: 59

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Thr Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
            115                 120                 125

```
Thr Leu Met Ile Ser Arg Thr Pro Glu Val Thr Cys Val Val Val Asp
130                 135                 140

Val Ser His Glu Asp Pro Glu Val Gln Phe Asn Trp Tyr Val Asp Gly
145                 150                 155                 160

Met Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro

<210> SEQ ID NO 60
<211> LENGTH: 324
<212> TYPE: PRT
<213> ORGANISM: Homo sapiens

<400> SEQUENCE: 60

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175
```

```
Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
            245                 250                 255

Ala Val Glu Trp Glu Ser Asn Gly Gln Pro Glu Asn Asn Tyr Lys Thr
        260                 265                 270

Thr Pro Pro Met Leu Asp Ser Asp Gly Ser Phe Phe Leu Tyr Ser Lys
    275                 280                 285

Leu Thr Val Asp Lys Ser Arg Trp Gln Gln Gly Asn Val Phe Ser Cys
290                 295                 300

Ser Val Met His Glu Ala Leu His Asn His Tyr Thr Gln Lys Ser Leu
            305                 310                 315                 320

Ser Leu Ser Pro

<210> SEQ ID NO 61
<211> LENGTH: 324
<212> TYPE: PRT
<213> ORGANISM: Homo sapiens

<400> SEQUENCE: 61

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Thr Cys Asn Val Asp His Lys Pro Ser Asn Thr Lys Val Asp Lys
            85                  90                  95

Thr Val Glu Arg Lys Cys Cys Val Glu Cys Pro Pro Cys Pro Ala Pro
        100                 105                 110

Pro Val Ala Gly Pro Ser Val Phe Leu Phe Pro Pro Lys Pro Lys Asp
    115                 120                 125

Thr Leu Met Ile Ser Arg Thr Pro Glu Val Thr Cys Val Val Val Asp
130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
            165                 170                 175

Ser Thr Phe Arg Val Val Ser Val Leu Thr Val Val His Gln Asp Trp
        180                 185                 190

Leu Asn Gly Lys Glu Tyr Lys Cys Lys Val Ser Asn Lys Gly Leu Pro
    195                 200                 205

Ala Pro Ile Glu Lys Thr Ile Ser Lys Thr Lys Gly Gln Pro Arg Glu
210                 215                 220
```

```
Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
            245                 250                 255

Ala Val Glu Trp Glu Ser Asn Gly Gln Pro Glu Asn Asn Tyr Lys Thr
        260                 265                 270

Thr Pro Pro Met Leu Asp Ser Asp Gly Ser Phe Phe Leu Tyr Ser Lys
    275                 280                 285

Leu Thr Val Asp Lys Ser Arg Trp Gln Gln Gly Asn Val Phe Ser Cys
290                 295                 300

Ser Val Met His Glu Ala Leu His Asn His Tyr Thr Gln Lys Ser Leu
305                 310                 315                 320

Ser Leu Ser Pro

<210> SEQ ID NO 62
<211> LENGTH: 324
<212> TYPE: PRT
<213> ORGANISM: Homo sapiens

<400> SEQUENCE: 62

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
            245                 250                 255

Ala Val Glu Trp Glu Ser Asn Gly Gln Pro Glu Asn Asn Tyr Lys Thr
        260                 265                 270
```

```
Thr Pro Pro Met Leu Asp Ser Asp Gly Ser Phe Phe Leu Tyr Ser Lys
            275                 280                 285
Leu Thr Val Asp Lys Ser Arg Trp Gln Gln Gly Asn Val Phe Ser Cys
    290                 295                 300
Ser Val Met His Glu Ala Leu His Asn His Tyr Thr Gln Lys Ser Leu
305                 310                 315                 320
Ser Leu Ser Pro

<210> SEQ ID NO 63
<211> LENGTH: 324
<212> TYPE: PRT
<213> ORGANISM: Homo sapiens

<400> SEQUENCE: 63

Ala Ser Thr Lys Gly Pro Ser Val Phe Pro Leu Ala Pro Cys Ser Arg
1               5                   10                  15
Ser Thr Ser Glu Ser Thr Ala Ala Leu Gly Cys Leu Val Lys Asp Tyr
            20                  25                  30
Phe Pro Glu Pro Val Thr Val Ser Trp Asn Ser Gly Ala Leu Thr Ser
        35                  40                  45
Gly Val His Thr Phe Pro Ala Val Leu Gln Ser Ser Gly Leu Tyr Ser
    50                  55                  60
Leu Ser Ser Val Val Thr Val Pro Ser Ser Asn Phe Gly Thr Gln Thr
65                  70                  75                  80
Tyr Thr Cys Asn Val Asp His Lys Pro Ser Asn Thr Lys Val Asp Lys
                85                  90                  95
Thr Val Glu Arg Lys Cys Cys Val Glu Cys Pro Pro Cys Pro Ala Pro
            100                 105                 110
Pro Val Ala Gly Pro Ser Val Phe Leu Phe Pro Pro Lys Pro Lys Asp
        115                 120                 125
Thr Leu Met Ile Ser Arg Thr Pro Glu Val Thr Cys Val Val Val Asp
130                 135                 140
Val Ser His Glu Asp Pro Glu Val Gln Phe Asn Trp Tyr Val Asp Gly
145                 150                 155                 160
Val Glu Val His Asn Ala Lys Thr Lys Pro Arg Glu Glu Gln Phe Asn
                165                 170                 175
Ser Thr Phe Arg Val Val Ser Val Leu Thr Val Val His Gln Asp Trp
            180                 185                 190
Leu Asn Gly Lys Glu Tyr Lys Cys Lys Val Ser Asn Lys Gly Leu Pro
        195                 200                 205
Ala Pro Ile Glu Lys Thr Ile Ser Lys Thr Lys Gly Gln Pro Arg Glu
    210                 215                 220
Pro Gln Val Tyr Thr Leu Pro Pro Ser Arg Glu Glu Met Thr Lys Asn
225                 230                 235                 240
Gln Val Ser Leu Thr Cys Leu Val Lys Gly Phe Tyr Pro Ser Asp Ile
                245                 250                 255
Ser Val Glu Trp Glu Ser Asn Gly Gln Pro Glu Asn Asn Tyr Lys Thr
            260                 265                 270
Thr Pro Pro Met Leu Asp Ser Asp Gly Ser Phe Phe Leu Tyr Ser Lys
        275                 280                 285
Leu Thr Val Asp Lys Ser Arg Trp Gln Gln Gly Asn Val Phe Ser Cys
    290                 295                 300
Ser Val Met His Glu Ala Leu His Asn His Tyr Thr Gln Lys Ser Leu
305                 310                 315                 320
```

Ser Leu Ser Pro

<210> SEQ ID NO 64
<211> LENGTH: 375
<212> TYPE: PRT
<213> ORGANISM: Homo sapiens

<400> SEQUENCE: 64

```
Ala Ser Thr Lys Gly Pro Ser Val Phe Pro Leu Ala Pro Cys Ser Arg
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Thr Cys Asn Val Asn His Lys Pro Ser Asn Thr Lys Val Asp Lys
                85                  90                  95

Arg Val Glu Leu Lys Thr Pro Leu Gly Asp Thr Thr His Thr Cys Pro
            100                 105                 110

Arg Cys Pro Glu Pro Lys Ser Cys Asp Thr Pro Pro Cys Pro Arg
        115                 120                 125

Cys Pro Glu Pro Lys Ser Cys Asp Thr Pro Pro Cys Pro Arg Cys
    130                 135                 140

Pro Glu Pro Lys Ser Cys Asp Thr Pro Pro Cys Pro Arg Cys Pro
145                 150                 155                 160

Ala Pro Glu Leu Leu Gly Gly Pro Ser Val Phe Leu Phe Pro Pro Lys
                165                 170                 175

Pro Lys Asp Thr Leu Met Ile Ser Arg Thr Pro Glu Val Thr Cys Val
            180                 185                 190

Val Val Asp Val Ser His Glu Asp Pro Glu Val Gln Phe Lys Trp Tyr
        195                 200                 205

Val Asp Gly Val Glu Val His Asn Ala Lys Thr Lys Pro Arg Glu Glu
    210                 215                 220

Gln Tyr Asn Ser Thr Phe Arg Val Val Ser Val Leu Thr Val Leu His
225                 230                 235                 240

Gln Asp Trp Leu Asn Gly Lys Glu Tyr Lys Cys Lys Val Ser Asn Lys
                245                 250                 255

Ala Leu Pro Ala Pro Ile Glu Lys Thr Ile Ser Lys Thr Lys Gly Gln
            260                 265                 270

Pro Arg Glu Pro Gln Val Tyr Thr Leu Pro Pro Ser Arg Glu Glu Met
        275                 280                 285

Thr Lys Asn Gln Val Ser Leu Thr Cys Leu Val Lys Gly Phe Tyr Pro
    290                 295                 300

Ser Asp Ile Ala Val Glu Trp Glu Ser Ser Gly Gln Pro Glu Asn Asn
305                 310                 315                 320

Tyr Asn Thr Thr Pro Pro Met Leu Asp Ser Asp Gly Ser Phe Phe Leu
                325                 330                 335

Tyr Ser Lys Leu Thr Val Asp Lys Ser Arg Trp Gln Gln Gly Asn Ile
            340                 345                 350

Phe Ser Cys Ser Val Met His Glu Ala Leu His Asn Arg Phe Thr Gln
        355                 360                 365
```

Lys Ser Leu Ser Leu Ser Pro
    370             375

<210> SEQ ID NO 65
<211> LENGTH: 375
<212> TYPE: PRT
<213> ORGANISM: Homo sapiens

<400> SEQUENCE: 65

Ala Ser Thr Lys Gly Pro Ser Val Phe Pro Leu Ala Pro Cys Ser Arg
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Thr Cys Asn Val Asn His Lys Pro Ser Asn Thr Lys Val Asp Lys
                85                  90                  95

Arg Val Glu Leu Lys Thr Pro Leu Gly Asp Thr Thr His Thr Cys Pro
            100                 105                 110

Arg Cys Pro Glu Pro Lys Ser Cys Asp Thr Pro Pro Pro Cys Pro Arg
        115                 120                 125

Cys Pro Glu Pro Lys Ser Cys Asp Thr Pro Pro Pro Cys Pro Arg Cys
    130                 135                 140

Pro Glu Pro Lys Ser Cys Asp Thr Pro Pro Pro Cys Pro Arg Cys Pro
145                 150                 155                 160

Ala Pro Glu Leu Leu Gly Gly Pro Ser Val Phe Leu Phe Pro Pro Lys
                165                 170                 175

Pro Lys Asp Thr Leu Met Ile Ser Arg Thr Pro Glu Val Thr Cys Val
            180                 185                 190

Val Val Asp Val Ser His Glu Asp Pro Glu Val Gln Phe Lys Trp Tyr
        195                 200                 205

Val Asp Gly Val Glu Val His Asn Ala Lys Thr Lys Pro Arg Glu Glu
    210                 215                 220

Gln Tyr Asn Ser Thr Phe Arg Val Val Ser Val Leu Thr Val Leu His
225                 230                 235                 240

Gln Asp Trp Leu Asn Gly Lys Glu Tyr Lys Cys Lys Val Ser Asn Lys
                245                 250                 255

Ala Leu Pro Ala Pro Ile Glu Lys Thr Ile Ser Lys Thr Lys Gly Gln
            260                 265                 270

Pro Arg Glu Pro Gln Val Tyr Thr Leu Pro Pro Ser Arg Glu Glu Met
        275                 280                 285

Thr Lys Asn Gln Val Ser Leu Thr Cys Leu Val Lys Gly Phe Tyr Pro
    290                 295                 300

Ser Asp Ile Ala Val Glu Trp Glu Ser Ser Gly Gln Pro Glu Asn Asn
305                 310                 315                 320

Tyr Asn Thr Thr Pro Pro Val Leu Asp Ser Asp Gly Ser Phe Phe Leu
                325                 330                 335

Tyr Ser Arg Leu Thr Val Asp Lys Ser Arg Trp Gln Glu Gly Asn Val
            340                 345                 350

Phe Ser Cys Ser Val Met His Glu Ala Leu His Asn Arg Phe Thr Gln
        355                 360                 365

```
Lys Ser Leu Ser Leu Ser Pro
        370             375

<210> SEQ ID NO 66
<211> LENGTH: 375
<212> TYPE: PRT
<213> ORGANISM: Homo sapiens

<400> SEQUENCE: 66

Ala Ser Thr Lys Gly Pro Ser Val Phe Pro Leu Ala Pro Cys Ser Arg
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Thr Cys Asn Val Asn His Lys Pro Ser Asn Thr Lys Val Asp Lys
                85                  90                  95

Arg Val Glu Leu Lys Thr Pro Leu Gly Asp Thr Thr His Thr Cys Pro
            100                 105                 110

Arg Cys Pro Glu Pro Lys Ser Cys Asp Thr Pro Pro Cys Pro Arg
        115                 120                 125

Cys Pro Glu Pro Lys Ser Cys Asp Thr Pro Pro Cys Pro Arg Cys
    130                 135                 140

Pro Glu Pro Lys Ser Cys Asp Thr Pro Pro Cys Pro Arg Cys Pro
145                 150                 155                 160

Ala Pro Glu Leu Leu Gly Gly Pro Ser Val Phe Leu Phe Pro Pro Lys
                165                 170                 175

Pro Lys Asp Thr Leu Met Ile Ser Arg Thr Pro Glu Val Thr Cys Val
            180                 185                 190

Val Val Asp Val Ser His Glu Asp Pro Glu Val Gln Phe Lys Trp Tyr
        195                 200                 205

Val Asp Gly Val Glu Val His Asn Ala Lys Thr Lys Pro Arg Glu Glu
    210                 215                 220

Gln Tyr Asn Ser Thr Phe Arg Val Val Ser Val Leu Thr Val Leu His
225                 230                 235                 240

Gln Asp Trp Leu Asn Gly Lys Glu Tyr Lys Cys Lys Val Ser Asn Lys
                245                 250                 255

Ala Leu Pro Ala Pro Ile Glu Lys Thr Ile Ser Lys Thr Lys Gly Gln
            260                 265                 270

Pro Arg Glu Pro Gln Val Tyr Thr Leu Pro Pro Ser Arg Glu Glu Met
        275                 280                 285

Thr Lys Asn Gln Val Ser Leu Thr Cys Leu Val Lys Gly Phe Tyr Pro
    290                 295                 300

Ser Asp Ile Ala Val Glu Trp Glu Ser Ser Gly Gln Pro Glu Asn Asn
305                 310                 315                 320

Tyr Asn Thr Thr Pro Pro Met Leu Asp Ser Asp Gly Ser Phe Phe Leu
                325                 330                 335

Tyr Ser Lys Leu Thr Val Asp Lys Ser Arg Trp Gln Gln Gly Asn Ile
            340                 345                 350

Phe Ser Cys Ser Val Met His Glu Ala Leu His Asn Arg Phe Thr Gln
```

```
            355                 360                 365
Lys Ser Leu Ser Leu Ser Pro
    370                 375

<210> SEQ ID NO 67
<211> LENGTH: 375
<212> TYPE: PRT
<213> ORGANISM: Homo sapiens

<400> SEQUENCE: 67

Ala Ser Thr Lys Gly Pro Ser Val Phe Pro Leu Ala Pro Cys Ser Arg
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Thr Cys Asn Val Asn His Lys Pro Ser Asn Thr Lys Val Asp Lys
                85                  90                  95

Arg Val Glu Leu Lys Thr Pro Leu Gly Asp Thr Thr His Thr Cys Pro
            100                 105                 110

Arg Cys Pro Glu Pro Lys Ser Cys Asp Thr Pro Pro Pro Cys Pro Arg
        115                 120                 125

Cys Pro Glu Pro Lys Ser Cys Asp Thr Pro Pro Pro Cys Pro Arg Cys
    130                 135                 140

Pro Glu Pro Lys Ser Cys Asp Thr Pro Pro Pro Cys Pro Arg Cys Pro
145                 150                 155                 160

Ala Pro Glu Leu Leu Gly Gly Pro Ser Val Phe Leu Phe Pro Pro Lys
                165                 170                 175

Pro Lys Asp Thr Leu Met Ile Ser Arg Thr Pro Glu Val Thr Cys Val
            180                 185                 190

Val Val Asp Val Ser His Glu Asp Pro Glu Val Gln Phe Lys Trp Tyr
        195                 200                 205

Val Asp Gly Val Glu Val His Asn Ala Lys Thr Lys Pro Arg Glu Glu
    210                 215                 220

Gln Tyr Asn Ser Thr Phe Arg Val Val Ser Val Leu Thr Val Leu His
225                 230                 235                 240

Gln Asp Trp Leu Asn Gly Lys Glu Tyr Lys Cys Lys Val Ser Asn Lys
                245                 250                 255

Ala Leu Pro Ala Pro Ile Glu Lys Thr Ile Ser Lys Thr Lys Gly Gln
            260                 265                 270

Pro Arg Glu Pro Gln Val Tyr Thr Leu Pro Pro Ser Arg Glu Glu Met
        275                 280                 285

Thr Lys Asn Gln Val Ser Leu Thr Cys Leu Val Lys Gly Phe Tyr Pro
    290                 295                 300

Ser Asp Ile Ala Val Glu Trp Glu Ser Ser Gly Gln Pro Glu Asn Asn
305                 310                 315                 320

Tyr Asn Thr Thr Pro Pro Met Leu Asp Ser Asp Gly Ser Phe Phe Leu
                325                 330                 335

Tyr Ser Lys Leu Thr Val Asp Lys Ser Arg Trp Gln Gln Gly Asn Ile
            340                 345                 350
```

Phe Ser Cys Ser Val Met His Glu Ala Leu His Asn Arg Phe Thr Gln
            355                 360                 365

Lys Ser Leu Ser Leu Ser Pro
    370                 375

<210> SEQ ID NO 68
<211> LENGTH: 375
<212> TYPE: PRT
<213> ORGANISM: Homo sapiens

<400> SEQUENCE: 68

Ala Ser Thr Lys Gly Pro Ser Val Phe Pro Leu Ala Pro Cys Ser Arg
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Thr Cys Asn Val Asn His Lys Pro Ser Asn Thr Lys Val Asp Lys
                85                  90                  95

Arg Val Glu Leu Lys Thr Pro Leu Gly Asp Thr Thr His Thr Cys Pro
            100                 105                 110

Arg Cys Pro Glu Pro Lys Ser Cys Asp Thr Pro Pro Pro Cys Pro Arg
        115                 120                 125

Cys Pro Glu Pro Lys Ser Cys Asp Thr Pro Pro Pro Cys Pro Arg Cys
    130                 135                 140

Pro Glu Pro Lys Ser Cys Asp Thr Pro Pro Pro Cys Pro Arg Cys Pro
145                 150                 155                 160

Ala Pro Glu Leu Leu Gly Gly Pro Ser Val Phe Leu Phe Pro Pro Lys
                165                 170                 175

Pro Lys Asp Thr Leu Met Ile Ser Arg Thr Pro Glu Val Thr Cys Val
            180                 185                 190

Val Val Asp Val Ser His Glu Asp Pro Glu Val Gln Phe Lys Trp Tyr
        195                 200                 205

Val Asp Gly Val Glu Val His Asn Ala Lys Thr Lys Pro Arg Glu Glu
    210                 215                 220

Gln Tyr Asn Ser Thr Phe Arg Val Val Ser Val Leu Thr Val Leu His
225                 230                 235                 240

Gln Asp Trp Leu Asn Gly Lys Glu Tyr Lys Cys Lys Val Ser Asn Lys
                245                 250                 255

Ala Leu Pro Ala Pro Ile Glu Lys Thr Ile Ser Lys Thr Lys Gly Gln
            260                 265                 270

Pro Arg Glu Pro Gln Val Tyr Thr Leu Pro Pro Ser Arg Glu Glu Met
        275                 280                 285

Thr Lys Asn Gln Val Ser Leu Thr Cys Leu Val Lys Gly Phe Tyr Pro
    290                 295                 300

Ser Asp Ile Ala Val Glu Trp Glu Ser Ser Gly Gln Pro Glu Asn Asn
305                 310                 315                 320

Tyr Lys Thr Thr Pro Pro Met Leu Asp Ser Asp Gly Ser Phe Phe Leu
                325                 330                 335

Tyr Ser Lys Leu Thr Val Asp Lys Ser Arg Trp Gln Gln Gly Asn Ile
            340                 345                 350

Phe Ser Cys Ser Val Met His Glu Ala Leu His Asn Arg Phe Thr Gln
        355                 360                 365

Lys Ser Leu Ser Leu Ser Pro
    370                 375

<210> SEQ ID NO 69
<211> LENGTH: 375
<212> TYPE: PRT
<213> ORGANISM: Homo sapiens

<400> SEQUENCE: 69

Ala Ser Thr Lys Gly Pro Ser Val Phe Pro Leu Ala Pro Cys Ser Arg
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Thr Cys Asn Val Asn His Lys Pro Ser Asn Thr Lys Val Asp Lys
                85                  90                  95

Arg Val Glu Leu Lys Thr Pro Leu Gly Asp Thr Thr His Thr Cys Pro
            100                 105                 110

Arg Cys Pro Glu Pro Lys Ser Cys Asp Thr Pro Pro Pro Cys Pro Arg
        115                 120                 125

Cys Pro Glu Pro Lys Ser Cys Asp Thr Pro Pro Pro Cys Pro Arg Cys
    130                 135                 140

Pro Glu Pro Lys Ser Cys Asp Thr Pro Pro Pro Cys Pro Arg Cys Pro
145                 150                 155                 160

Ala Pro Glu Leu Leu Gly Gly Pro Ser Val Phe Leu Phe Pro Pro Lys
                165                 170                 175

Pro Lys Asp Thr Leu Met Ile Ser Arg Thr Pro Glu Val Thr Cys Val
            180                 185                 190

Val Val Asp Val Ser His Glu Asp Pro Glu Val Gln Phe Lys Trp Tyr
        195                 200                 205

Val Asp Gly Val Glu Val His Asn Ala Lys Thr Lys Pro Arg Glu Glu
    210                 215                 220

Gln Tyr Asn Ser Thr Phe Arg Val Val Ser Val Leu Thr Val Leu His
225                 230                 235                 240

Gln Asp Trp Leu Asn Gly Lys Glu Tyr Lys Cys Lys Val Ser Asn Lys
                245                 250                 255

Ala Leu Pro Ala Pro Ile Glu Lys Thr Ile Ser Lys Thr Lys Gly Gln
            260                 265                 270

Pro Arg Glu Pro Gln Val Tyr Thr Leu Pro Pro Ser Arg Glu Glu Met
        275                 280                 285

Thr Lys Asn Gln Val Ser Leu Thr Cys Leu Val Lys Gly Phe Tyr Pro
    290                 295                 300

Ser Asp Ile Ala Val Glu Trp Glu Ser Ser Gly Gln Pro Glu Asn Asn
305                 310                 315                 320

Tyr Lys Thr Thr Pro Pro Met Leu Asp Ser Asp Gly Ser Phe Phe Leu
                325                 330                 335

Tyr Ser Lys Leu Thr Val Asp Lys Ser Arg Trp Gln Gln Gly Asn Ile

```
                    340                 345                 350
Phe Ser Cys Ser Val Met His Glu Ala Leu His Asn Arg Phe Thr Gln
                355                 360                 365

Lys Ser Leu Ser Leu Ser Pro
        370             375

<210> SEQ ID NO 70
<211> LENGTH: 375
<212> TYPE: PRT
<213> ORGANISM: Homo sapiens

<400> SEQUENCE: 70

Ala Ser Thr Lys Gly Pro Ser Val Phe Pro Leu Ala Pro Cys Ser Arg
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Thr Cys Asn Val Asn His Lys Pro Ser Asn Thr Lys Val Asp Lys
                85                  90                  95

Arg Val Glu Leu Lys Thr Pro Leu Gly Asp Thr Thr His Thr Cys Pro
                100                 105                 110

Arg Cys Pro Glu Pro Lys Ser Cys Asp Thr Pro Pro Cys Pro Arg
            115                 120                 125

Cys Pro Glu Pro Lys Ser Cys Asp Thr Pro Pro Cys Pro Arg Cys
        130                 135                 140

Pro Glu Pro Lys Ser Cys Asp Thr Pro Pro Cys Pro Arg Cys Pro
145                 150                 155                 160

Ala Pro Glu Leu Leu Gly Gly Pro Ser Val Phe Leu Phe Pro Pro Lys
                165                 170                 175

Pro Lys Asp Thr Leu Met Ile Ser Arg Thr Pro Glu Val Thr Cys Val
            180                 185                 190

Val Val Asp Val Ser His Glu Asp Pro Glu Val Gln Phe Lys Trp Tyr
        195                 200                 205

Val Asp Gly Val Glu Val His Asn Ala Lys Thr Lys Pro Arg Glu Glu
    210                 215                 220

Gln Tyr Asn Ser Thr Phe Arg Val Val Ser Val Leu Thr Val Leu His
225                 230                 235                 240

Gln Asp Trp Leu Asn Gly Lys Glu Tyr Lys Cys Lys Val Ser Asn Lys
                245                 250                 255

Ala Leu Pro Ala Pro Ile Glu Lys Thr Ile Ser Lys Thr Lys Gly Gln
            260                 265                 270

Pro Arg Glu Pro Gln Val Tyr Thr Leu Pro Pro Ser Arg Glu Glu Met
        275                 280                 285

Thr Lys Asn Gln Val Ser Leu Thr Cys Leu Val Lys Gly Phe Tyr Pro
    290                 295                 300

Ser Asp Ile Ala Val Glu Trp Glu Ser Asn Gly Gln Pro Glu Asn Asn
305                 310                 315                 320

Tyr Asn Thr Thr Pro Pro Met Leu Asp Ser Asp Gly Ser Phe Phe Leu
                325                 330                 335
```

```
Tyr Ser Lys Leu Thr Val Asp Lys Ser Arg Trp Gln Gln Gly Asn Ile
            340                 345                 350

Phe Ser Cys Ser Val Met His Glu Ala Leu His Asn Arg Phe Thr Gln
            355                 360                 365

Lys Ser Leu Ser Leu Ser Pro
            370             375

<210> SEQ ID NO 71
<211> LENGTH: 375
<212> TYPE: PRT
<213> ORGANISM: Homo sapiens

<400> SEQUENCE: 71

Ala Ser Thr Lys Gly Pro Ser Val Phe Pro Leu Ala Pro Cys Ser Arg
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Thr Cys Asn Val Asn His Lys Pro Ser Asn Thr Lys Val Asp Lys
                85                  90                  95

Arg Val Glu Leu Lys Thr Pro Leu Gly Asp Thr Thr His Thr Cys Pro
            100                 105                 110

Arg Cys Pro Glu Pro Lys Ser Cys Asp Thr Pro Pro Pro Cys Pro Arg
        115                 120                 125

Cys Pro Glu Pro Lys Ser Cys Asp Thr Pro Pro Pro Cys Pro Arg Cys
    130                 135                 140

Pro Glu Pro Lys Ser Cys Asp Thr Pro Pro Pro Cys Pro Arg Cys Pro
145                 150                 155                 160

Ala Pro Glu Leu Leu Gly Gly Pro Ser Val Phe Leu Phe Pro Pro Lys
                165                 170                 175

Pro Lys Asp Thr Leu Met Ile Ser Arg Thr Pro Glu Val Thr Cys Val
            180                 185                 190

Val Val Asp Val Ser His Glu Asp Pro Glu Val Gln Phe Lys Trp Tyr
        195                 200                 205

Val Asp Gly Val Glu Val His Asn Ala Lys Thr Lys Pro Arg Glu Glu
    210                 215                 220

Gln Tyr Asn Ser Thr Phe Arg Val Val Ser Val Leu Thr Val Val His
225                 230                 235                 240

Gln Asp Trp Leu Asn Gly Lys Glu Tyr Lys Cys Lys Val Ser Asn Lys
                245                 250                 255

Ala Leu Pro Ala Pro Ile Glu Lys Thr Ile Ser Lys Thr Lys Gly Gln
            260                 265                 270

Pro Arg Glu Pro Gln Val Tyr Thr Leu Pro Pro Ser Arg Glu Glu Met
        275                 280                 285

Thr Lys Asn Gln Val Ser Leu Thr Cys Leu Val Lys Gly Phe Tyr Pro
    290                 295                 300

Ser Asp Ile Ala Val Glu Trp Glu Ser Ser Gly Gln Pro Glu Asn Asn
305                 310                 315                 320

Tyr Asn Thr Thr Pro Pro Met Leu Asp Ser Asp Gly Ser Phe Phe Leu
                325                 330                 335
```

```
Tyr Ser Lys Leu Thr Val Asp Lys Ser Arg Trp Gln Gln Gly Asn Ile
            340                 345                 350

Phe Ser Cys Ser Val Met His Glu Ala Leu His Asn Arg Phe Thr Gln
            355                 360                 365

Lys Ser Leu Ser Leu Ser Pro
            370             375

<210> SEQ ID NO 72
<211> LENGTH: 375
<212> TYPE: PRT
<213> ORGANISM: Homo sapiens

<400> SEQUENCE: 72

Ala Ser Thr Lys Gly Pro Ser Val Phe Pro Leu Ala Pro Cys Ser Arg
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Thr Cys Asn Val Asn His Lys Pro Ser Asn Thr Lys Val Asp Lys
                85                  90                  95

Arg Val Glu Leu Lys Thr Pro Leu Gly Asp Thr Thr His Thr Cys Pro
            100                 105                 110

Arg Cys Pro Glu Pro Lys Ser Cys Asp Thr Pro Pro Cys Pro Arg
        115                 120                 125

Cys Pro Glu Pro Lys Ser Cys Asp Thr Pro Pro Cys Pro Arg Cys
    130                 135                 140

Pro Glu Pro Lys Ser Cys Asp Thr Pro Pro Cys Pro Arg Cys Pro
145                 150                 155                 160

Ala Pro Glu Leu Leu Gly Gly Pro Ser Val Phe Leu Phe Pro Pro Lys
                165                 170                 175

Pro Lys Asp Thr Leu Met Ile Ser Arg Thr Pro Glu Val Thr Cys Val
            180                 185                 190

Val Val Asp Val Ser His Glu Asp Pro Glu Val Gln Phe Lys Trp Tyr
        195                 200                 205

Val Asp Gly Val Glu Val His Asn Ala Lys Thr Lys Pro Arg Glu Glu
    210                 215                 220

Gln Tyr Asn Ser Thr Phe Arg Val Val Ser Val Leu Thr Val Leu His
225                 230                 235                 240

Gln Asp Trp Leu Asn Gly Lys Glu Tyr Lys Cys Lys Val Ser Asn Lys
                245                 250                 255

Ala Leu Pro Ala Pro Ile Glu Lys Thr Ile Ser Lys Thr Lys Gly Gln
            260                 265                 270

Pro Arg Glu Pro Gln Val Tyr Thr Leu Pro Pro Ser Arg Glu Glu Met
        275                 280                 285

Thr Lys Asn Gln Val Ser Leu Thr Cys Leu Val Lys Gly Phe Tyr Pro
    290                 295                 300

Ser Asp Ile Ala Val Glu Trp Glu Ser Ser Gly Gln Pro Glu Asn Asn
305                 310                 315                 320

Tyr Asn Thr Thr Pro Pro Met Leu Asp Ser Asp Gly Ser Phe Phe Leu
```

```
                        325                 330                 335
        Tyr Ser Lys Leu Thr Val Asp Lys Ser Arg Trp Gln Gln Gly Asn Ile
                    340                 345                 350

Phe Ser Cys Ser Val Met His Glu Ala Leu His Asn Arg Phe Thr Gln
                    355                 360                 365

Lys Ser Leu Ser Leu Ser Pro
                    370                 375

<210> SEQ ID NO 73
<211> LENGTH: 375
<212> TYPE: PRT
<213> ORGANISM: Homo sapiens

<400> SEQUENCE: 73

Ala Ser Thr Lys Gly Pro Ser Val Phe Pro Leu Ala Pro Cys Ser Arg
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Thr Cys Asn Val Asn His Lys Pro Ser Asn Thr Lys Val Asp Lys
                85                  90                  95

Arg Val Glu Leu Lys Thr Pro Leu Gly Asp Thr Thr His Thr Cys Pro
            100                 105                 110

Arg Cys Pro Glu Pro Lys Ser Cys Asp Thr Pro Pro Pro Cys Pro Arg
        115                 120                 125

Cys Pro Glu Pro Lys Ser Cys Asp Thr Pro Pro Pro Cys Pro Arg Cys
    130                 135                 140

Pro Glu Pro Lys Ser Cys Asp Thr Pro Pro Pro Cys Pro Arg Cys Pro
145                 150                 155                 160

Ala Pro Glu Leu Leu Gly Gly Pro Ser Val Phe Leu Phe Pro Pro Lys
                165                 170                 175

Pro Lys Asp Thr Leu Met Ile Ser Arg Thr Pro Glu Val Thr Cys Val
            180                 185                 190

Val Val Asp Val Ser His Glu Asp Pro Glu Val Gln Phe Lys Trp Tyr
        195                 200                 205

Val Asp Gly Val Glu Val His Asn Ala Lys Thr Lys Pro Arg Glu Glu
    210                 215                 220

Gln Phe Asn Ser Thr Phe Arg Val Val Ser Val Leu Thr Val Leu His
225                 230                 235                 240

Gln Asp Trp Leu Asn Gly Lys Glu Tyr Lys Cys Lys Val Ser Asn Lys
                245                 250                 255

Ala Leu Pro Ala Pro Ile Glu Lys Thr Ile Ser Lys Thr Lys Gly Gln
            260                 265                 270

Pro Arg Glu Pro Gln Val Tyr Thr Leu Pro Pro Ser Arg Glu Glu Met
        275                 280                 285

Thr Lys Asn Gln Val Ser Leu Thr Cys Leu Val Lys Gly Phe Tyr Pro
    290                 295                 300

Ser Asp Ile Ala Val Glu Trp Glu Ser Ser Gly Gln Pro Glu Asn Asn
305                 310                 315                 320
```

```
Tyr Asn Thr Thr Pro Pro Met Leu Asp Ser Asp Gly Ser Phe Phe Leu
                325                 330                 335

Tyr Ser Lys Leu Thr Val Asp Lys Ser Arg Trp Gln Gln Gly Asn Ile
            340                 345                 350

Phe Ser Cys Ser Val Met His Glu Ala Leu His Asn Arg Phe Thr Gln
        355                 360                 365

Lys Ser Leu Ser Leu Ser Pro
370             375

<210> SEQ ID NO 74
<211> LENGTH: 375
<212> TYPE: PRT
<213> ORGANISM: Homo sapiens

<400> SEQUENCE: 74

Ala Ser Thr Lys Gly Pro Ser Val Phe Pro Leu Ala Pro Cys Ser Arg
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Thr Cys Asn Val Asn His Lys Pro Ser Asn Thr Lys Val Asp Lys
                85                  90                  95

Arg Val Glu Leu Lys Thr Pro Leu Gly Asp Thr Thr His Thr Cys Pro
            100                 105                 110

Arg Cys Pro Glu Pro Lys Ser Cys Asp Thr Pro Pro Cys Pro Arg
        115                 120                 125

Cys Pro Glu Pro Lys Ser Cys Asp Thr Pro Pro Cys Pro Arg Cys
    130                 135                 140

Pro Glu Pro Lys Ser Cys Asp Thr Pro Pro Cys Pro Arg Cys Pro
145                 150                 155                 160

Ala Pro Glu Leu Leu Gly Gly Pro Ser Val Phe Leu Phe Pro Pro Lys
                165                 170                 175

Pro Lys Asp Thr Leu Met Ile Ser Arg Thr Pro Glu Val Thr Cys Val
            180                 185                 190

Val Val Asp Val Ser His Glu Asp Pro Glu Val Gln Phe Lys Trp Tyr
        195                 200                 205

Val Asp Gly Val Glu Val His Asn Ala Lys Thr Lys Pro Arg Glu Glu
    210                 215                 220

Gln Phe Asn Ser Thr Phe Arg Val Val Ser Val Leu Thr Val Leu His
225                 230                 235                 240

Gln Asp Trp Leu Asn Gly Lys Glu Tyr Lys Cys Lys Val Ser Asn Lys
                245                 250                 255

Ala Leu Pro Ala Pro Ile Glu Lys Thr Ile Ser Lys Thr Lys Gly Gln
            260                 265                 270

Pro Arg Glu Pro Gln Val Tyr Thr Leu Pro Pro Ser Arg Glu Glu Met
        275                 280                 285

Thr Lys Asn Gln Val Ser Leu Thr Cys Leu Val Lys Gly Phe Tyr Pro
    290                 295                 300

Ser Asp Ile Ala Val Glu Trp Glu Ser Ser Gly Gln Pro Glu Asn Asn
305                 310                 315                 320
```

```
Tyr Asn Thr Thr Pro Pro Met Leu Asp Ser Asp Gly Ser Phe Phe Leu
                325                 330                 335

Tyr Ser Lys Leu Thr Val Asp Lys Ser Arg Trp Gln Gln Gly Asn Ile
            340                 345                 350

Phe Ser Cys Ser Val Met His Glu Ala Leu His Asn Arg Phe Thr Gln
            355                 360                 365

Lys Ser Leu Ser Leu Ser Pro
    370                 375

<210> SEQ ID NO 75
<211> LENGTH: 375
<212> TYPE: PRT
<213> ORGANISM: Homo sapiens

<400> SEQUENCE: 75

Ala Ser Thr Lys Gly Pro Ser Val Phe Pro Leu Ala Pro Cys Ser Arg
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Thr Cys Asn Val Asn His Lys Pro Ser Asn Thr Lys Val Asp Lys
                85                  90                  95

Arg Val Glu Leu Lys Thr Pro Leu Gly Asp Thr Thr His Thr Cys Pro
            100                 105                 110

Arg Cys Pro Glu Pro Lys Ser Cys Asp Thr Pro Pro Pro Cys Pro Arg
        115                 120                 125

Cys Pro Glu Pro Lys Ser Cys Asp Thr Pro Pro Pro Cys Pro Arg Cys
    130                 135                 140

Pro Glu Pro Lys Ser Cys Asp Thr Pro Pro Pro Cys Pro Arg Cys Pro
145                 150                 155                 160

Ala Pro Glu Leu Leu Gly Gly Pro Ser Val Phe Leu Phe Pro Pro Lys
                165                 170                 175

Pro Lys Asp Thr Leu Met Ile Ser Arg Thr Pro Glu Val Thr Cys Val
            180                 185                 190

Val Val Asp Val Ser His Glu Asp Pro Glu Val Gln Phe Lys Trp Tyr
        195                 200                 205

Val Asp Gly Val Glu Val His Asn Ala Lys Thr Lys Pro Arg Glu Glu
    210                 215                 220

Gln Tyr Asn Ser Thr Phe Arg Val Val Ser Val Leu Thr Val Leu His
225                 230                 235                 240

Gln Asp Trp Leu Asn Gly Lys Glu Tyr Lys Cys Lys Val Ser Asn Lys
                245                 250                 255

Ala Leu Pro Ala Pro Ile Glu Lys Thr Ile Ser Lys Thr Lys Gly Gln
            260                 265                 270

Pro Arg Glu Pro Gln Val Tyr Thr Leu Pro Pro Ser Arg Glu Glu Met
        275                 280                 285

Thr Lys Asn Gln Val Ser Leu Thr Cys Leu Val Lys Gly Phe Tyr Pro
    290                 295                 300

Ser Asp Ile Ala Val Glu Trp Glu Ser Ser Gly Gln Pro Glu Asn Asn
```

```
                305                 310                 315                 320
Tyr Lys Thr Thr Pro Pro Met Leu Asp Ser Asp Gly Ser Phe Phe Leu
                325                 330                 335

Tyr Ser Lys Leu Thr Val Asp Lys Ser Arg Trp Gln Glu Gly Asn Ile
                340                 345                 350

Phe Ser Cys Ser Val Met His Glu Ala Leu His Asn Arg Phe Thr Gln
                355                 360                 365

Lys Ser Leu Ser Leu Ser Pro
                370                 375

<210> SEQ ID NO 76
<211> LENGTH: 375
<212> TYPE: PRT
<213> ORGANISM: Homo sapiens

<400> SEQUENCE: 76

Ala Ser Thr Lys Gly Pro Ser Val Phe Pro Leu Ala Pro Cys Ser Arg
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Thr Cys Asn Val Asn His Lys Pro Ser Asn Thr Lys Val Asp Lys
                85                  90                  95

Arg Val Glu Leu Lys Thr Pro Leu Gly Asp Thr Thr His Thr Cys Pro
            100                 105                 110

Arg Cys Pro Glu Pro Lys Ser Cys Asp Thr Pro Pro Pro Cys Pro Arg
        115                 120                 125

Cys Pro Glu Pro Lys Ser Cys Asp Thr Pro Pro Pro Cys Pro Arg Cys
    130                 135                 140

Pro Glu Pro Lys Ser Cys Asp Thr Pro Pro Pro Cys Pro Arg Cys Pro
145                 150                 155                 160

Ala Pro Glu Leu Leu Gly Gly Pro Ser Val Phe Leu Phe Pro Pro Lys
                165                 170                 175

Pro Lys Asp Thr Leu Met Ile Ser Arg Thr Pro Glu Val Thr Cys Val
            180                 185                 190

Val Val Asp Val Ser His Glu Asp Pro Glu Val Gln Phe Lys Trp Tyr
        195                 200                 205

Val Asp Gly Val Glu Val His Asn Ala Lys Thr Lys Leu Arg Glu Glu
    210                 215                 220

Gln Tyr Asn Ser Thr Phe Arg Val Val Ser Val Leu Thr Val Leu His
225                 230                 235                 240

Gln Asp Trp Leu Asn Gly Lys Glu Tyr Lys Cys Lys Val Ser Asn Lys
                245                 250                 255

Ala Leu Pro Ala Pro Ile Glu Lys Thr Ile Ser Lys Thr Lys Gly Gln
            260                 265                 270

Pro Arg Glu Pro Gln Val Tyr Thr Leu Pro Pro Ser Arg Glu Glu Met
        275                 280                 285

Thr Lys Asn Gln Val Ser Leu Thr Cys Leu Val Lys Gly Phe Tyr Pro
    290                 295                 300
```

```
Ser Asp Ile Ala Val Glu Trp Glu Ser Asn Gly Gln Pro Glu Asn Asn
305                 310                 315                 320

Tyr Asn Thr Thr Pro Pro Met Leu Asp Ser Asp Gly Ser Phe Phe Leu
                325                 330                 335

Tyr Ser Lys Leu Thr Val Asp Lys Ser Arg Trp Gln Gln Gly Asn Ile
                340                 345                 350

Phe Ser Cys Ser Val Met His Glu Ala Leu His Asn Arg Tyr Thr Gln
                355                 360                 365

Lys Ser Leu Ser Leu Ser Pro
                370                 375

<210> SEQ ID NO 77
<211> LENGTH: 375
<212> TYPE: PRT
<213> ORGANISM: Homo sapiens

<400> SEQUENCE: 77

Ala Ser Thr Lys Gly Pro Ser Val Phe Pro Leu Ala Pro Cys Ser Arg
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Thr Cys Asn Val Asn His Lys Pro Ser Asn Thr Lys Val Asp Lys
                85                  90                  95

Arg Val Glu Leu Lys Thr Pro Leu Gly Asp Thr Thr His Thr Cys Pro
            100                 105                 110

Arg Cys Pro Glu Pro Lys Ser Cys Asp Thr Pro Pro Pro Cys Pro Arg
        115                 120                 125

Cys Pro Glu Pro Lys Ser Cys Asp Thr Pro Pro Pro Cys Pro Arg Cys
    130                 135                 140

Pro Glu Pro Lys Ser Cys Asp Thr Pro Pro Pro Cys Pro Arg Cys Pro
145                 150                 155                 160

Ala Pro Glu Leu Leu Gly Gly Pro Ser Val Phe Leu Phe Pro Pro Lys
                165                 170                 175

Pro Lys Asp Thr Leu Met Ile Ser Arg Thr Pro Glu Val Thr Cys Val
            180                 185                 190

Val Val Asp Val Ser His Glu Asp Pro Glu Val Gln Phe Lys Trp Tyr
        195                 200                 205

Val Asp Gly Val Glu Val His Asn Ala Lys Thr Lys Leu Arg Glu Glu
    210                 215                 220

Gln Tyr Asn Ser Thr Phe Arg Val Val Ser Val Leu Thr Val Leu His
225                 230                 235                 240

Gln Asp Trp Leu Asn Gly Lys Glu Tyr Lys Cys Lys Val Ser Asn Lys
                245                 250                 255

Ala Leu Pro Ala Pro Ile Glu Lys Thr Ile Ser Lys Thr Lys Gly Gln
            260                 265                 270

Pro Arg Glu Pro Gln Val Tyr Thr Leu Pro Pro Ser Arg Glu Glu Met
        275                 280                 285

Thr Lys Asn Gln Val Ser Leu Thr Cys Leu Val Lys Gly Phe Tyr Pro
    290                 295                 300
```

```
Ser Asp Ile Ala Val Glu Trp Glu Ser Asn Gly Gln Pro Glu Asn Asn
305                 310                 315                 320

Tyr Lys Thr Thr Pro Met Leu Asp Ser Asp Gly Ser Phe Phe Leu
            325                 330                 335

Tyr Ser Lys Leu Thr Val Asp Lys Ser Arg Trp Gln Gln Gly Asn Ile
        340                 345                 350

Phe Ser Cys Ser Val Met His Glu Ala Leu His Asn Arg Tyr Thr Gln
            355                 360                 365

Lys Ser Leu Ser Leu Ser Pro
370                 375

<210> SEQ ID NO 78
<211> LENGTH: 375
<212> TYPE: PRT
<213> ORGANISM: Homo sapiens

<400> SEQUENCE: 78

Ala Ser Thr Lys Gly Pro Ser Val Phe Pro Leu Ala Pro Cys Ser Arg
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Thr Cys Asn Val Asn His Lys Pro Ser Asn Thr Lys Val Asp Lys
                85                  90                  95

Arg Val Glu Leu Lys Thr Pro Leu Gly Asp Thr Thr His Thr Cys Pro
            100                 105                 110

Arg Cys Pro Glu Pro Lys Ser Cys Asp Thr Pro Pro Pro Cys Pro Arg
        115                 120                 125

Cys Pro Glu Pro Lys Ser Cys Asp Thr Pro Pro Pro Cys Pro Arg Cys
    130                 135                 140

Pro Glu Pro Lys Ser Cys Asp Thr Pro Pro Pro Cys Pro Arg Cys Pro
145                 150                 155                 160

Ala Pro Glu Leu Leu Gly Gly Pro Ser Val Phe Leu Phe Pro Pro Lys
                165                 170                 175

Pro Lys Asp Thr Leu Met Ile Ser Arg Thr Pro Glu Val Thr Cys Val
            180                 185                 190

Val Val Asp Val Ser His Glu Asp Pro Glu Val Gln Phe Lys Trp Tyr
        195                 200                 205

Val Asp Gly Val Glu Val His Asn Ala Lys Thr Lys Leu Arg Glu Glu
    210                 215                 220

Gln Tyr Asn Ser Thr Phe Arg Val Val Ser Val Leu Thr Val Leu His
225                 230                 235                 240

Gln Asp Trp Leu Asn Gly Lys Glu Tyr Lys Cys Lys Val Ser Asn Lys
                245                 250                 255

Ala Leu Pro Ala Pro Ile Glu Lys Thr Ile Ser Lys Ala Lys Gly Gln
            260                 265                 270

Pro Arg Glu Pro Gln Val Tyr Thr Leu Pro Pro Ser Arg Glu Glu Met
        275                 280                 285

Thr Lys Asn Gln Val Ser Leu Thr Cys Leu Val Lys Gly Phe Tyr Pro
```

```
                    290                 295                 300
Ser Asp Ile Ala Val Glu Trp Glu Ser Asn Gly Gln Pro Glu Asn Asn
305                 310                 315                 320

Tyr Asn Thr Thr Pro Pro Met Leu Asp Ser Asp Gly Ser Phe Phe Leu
                325                 330                 335

Tyr Ser Lys Leu Thr Val Asp Lys Ser Arg Trp Gln Gln Gly Asn Ile
                340                 345                 350

Phe Ser Cys Ser Val Met His Glu Ala Leu His Asn Arg Tyr Thr Gln
                355                 360                 365

Lys Ser Leu Ser Leu Ser Pro
                370                 375

<210> SEQ ID NO 79
<211> LENGTH: 375
<212> TYPE: PRT
<213> ORGANISM: Homo sapiens

<400> SEQUENCE: 79

Ala Ser Thr Lys Gly Pro Ser Val Phe Pro Leu Ala Pro Cys Ser Arg
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
                35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Asn Phe Gly Thr Gln Thr
65                  70                  75                  80

Tyr Thr Cys Asn Val Asn His Lys Pro Ser Asn Thr Lys Val Asp Lys
                85                  90                  95

Arg Val Glu Leu Lys Thr Pro Leu Gly Asp Thr Thr His Thr Cys Pro
                100                 105                 110

Arg Cys Pro Glu Pro Lys Ser Cys Asp Thr Pro Pro Pro Cys Pro Arg
                115                 120                 125

Cys Pro Glu Pro Lys Ser Cys Asp Thr Pro Pro Pro Cys Pro Arg Cys
        130                 135                 140

Pro Glu Pro Lys Ser Cys Asp Thr Pro Pro Pro Cys Pro Arg Cys Pro
145                 150                 155                 160

Ala Pro Glu Leu Leu Gly Gly Pro Ser Val Phe Leu Phe Pro Pro Lys
                165                 170                 175

Pro Lys Asp Thr Leu Met Ile Ser Arg Thr Pro Glu Val Thr Cys Val
                180                 185                 190

Val Val Asp Val Ser His Glu Asp Pro Glu Val Gln Phe Lys Trp Tyr
                195                 200                 205

Val Asp Gly Val Glu Val His Asn Ala Lys Thr Lys Pro Arg Glu Glu
        210                 215                 220

Gln Tyr Asn Ser Thr Phe Arg Val Val Ser Val Leu Thr Val Leu His
225                 230                 235                 240

Gln Asp Trp Leu Asn Gly Lys Glu Tyr Lys Cys Lys Val Ser Asn Lys
                245                 250                 255

Ala Leu Pro Ala Pro Ile Glu Lys Thr Ile Ser Lys Thr Lys Gly Gln
                260                 265                 270

Pro Arg Glu Pro Gln Val Tyr Thr Leu Pro Pro Ser Arg Glu Glu Met
                275                 280                 285
```

```
Thr Lys Asn Gln Val Ser Leu Thr Cys Leu Val Lys Gly Phe Tyr Pro
    290                 295                 300

Ser Asp Ile Ala Met Glu Trp Glu Ser Ser Gly Gln Pro Glu Asn Asn
305                 310                 315                 320

Tyr Lys Thr Thr Pro Pro Val Leu Asp Ser Asp Gly Ser Phe Phe Leu
                325                 330                 335

Tyr Ser Lys Leu Thr Val Asp Lys Ser Arg Trp Gln Gln Gly Asn Ile
            340                 345                 350

Phe Ser Cys Ser Val Met His Glu Ala Leu His Asn His Tyr Thr Gln
        355                 360                 365

Lys Ser Leu Ser Leu Ser Pro
    370                 375

<210> SEQ ID NO 80
<211> LENGTH: 375
<212> TYPE: PRT
<213> ORGANISM: Homo sapiens

<400> SEQUENCE: 80

Ala Ser Thr Lys Gly Pro Ser Val Phe Pro Leu Ala Pro Cys Ser Arg
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Tyr Ser Gly Leu Tyr Ser
    50                  55                  60

Leu Ser Ser Val Val Thr Val Pro Ser Ser Ser Leu Gly Thr Gln Thr
65                  70                  75                  80

Tyr Thr Cys Asn Val Asn His Lys Pro Ser Asn Thr Lys Val Asp Lys
                85                  90                  95

Arg Val Glu Leu Lys Thr Pro Leu Gly Asp Thr Thr His Thr Cys Pro
            100                 105                 110

Arg Cys Pro Glu Pro Lys Ser Cys Asp Thr Pro Pro Pro Cys Pro Arg
        115                 120                 125

Cys Pro Glu Pro Lys Ser Cys Asp Thr Pro Pro Pro Cys Pro Arg Cys
    130                 135                 140

Pro Glu Pro Lys Ser Cys Asp Thr Pro Pro Pro Cys Pro Arg Cys Pro
145                 150                 155                 160

Ala Pro Glu Leu Leu Gly Gly Pro Ser Val Phe Leu Phe Pro Pro Lys
                165                 170                 175

Pro Lys Asp Thr Leu Met Ile Ser Arg Thr Pro Glu Val Thr Cys Val
            180                 185                 190

Val Val Asp Val Ser His Glu Asp Pro Glu Val Gln Phe Lys Trp Tyr
        195                 200                 205

Val Asp Gly Val Glu Val His Asn Ala Lys Thr Lys Pro Trp Glu Glu
    210                 215                 220

Gln Tyr Asn Ser Thr Phe Arg Val Val Ser Val Leu Thr Val Leu His
225                 230                 235                 240

Gln Asp Trp Leu Asn Gly Lys Glu Tyr Lys Cys Lys Val Ser Asn Lys
                245                 250                 255

Ala Leu Pro Ala Pro Ile Glu Lys Thr Ile Ser Lys Thr Lys Gly Gln
            260                 265                 270

Pro Arg Glu Pro Gln Val Tyr Thr Leu Pro Pro Ser Arg Glu Glu Met
        275                 280                 285
```

```
Thr Lys Asn Gln Val Ser Leu Thr Cys Leu Val Lys Gly Phe Tyr Pro
    290                 295                 300

Ser Asp Ile Ala Met Glu Trp Glu Ser Ser Gly Gln Pro Glu Asn Asn
305                 310                 315                 320

Tyr Lys Thr Thr Pro Pro Val Leu Asp Ser Asp Gly Ser Phe Phe Leu
                325                 330                 335

Tyr Ser Lys Leu Thr Val Asp Lys Ser Arg Trp Gln Gln Gly Asn Ile
            340                 345                 350

Phe Ser Cys Ser Val Met His Glu Ala Leu His Asn His Tyr Thr Gln
        355                 360                 365

Lys Ser Leu Ser Leu Ser Pro
    370                 375

<210> SEQ ID NO 81
<211> LENGTH: 375
<212> TYPE: PRT
<213> ORGANISM: Homo sapiens

<400> SEQUENCE: 81

Ala Ser Thr Lys Gly Pro Ser Val Phe Pro Leu Ala Pro Cys Ser Arg
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Thr Cys Asn Val Asn His Lys Pro Ser Asn Thr Lys Val Asp Lys
                85                  90                  95

Arg Val Glu Leu Lys Thr Pro Leu Gly Asp Thr Thr His Thr Cys Pro
            100                 105                 110

Arg Cys Pro Glu Pro Lys Ser Cys Asp Thr Pro Pro Pro Cys Pro Arg
        115                 120                 125

Cys Pro Glu Pro Lys Ser Cys Asp Thr Pro Pro Pro Cys Pro Arg Cys
    130                 135                 140

Pro Glu Pro Lys Ser Cys Asp Thr Pro Pro Pro Cys Pro Arg Cys Pro
145                 150                 155                 160

Ala Pro Glu Leu Leu Gly Gly Pro Ser Val Phe Leu Phe Pro Pro Lys
                165                 170                 175

Pro Lys Asp Thr Leu Met Ile Ser Arg Thr Pro Glu Val Thr Cys Val
            180                 185                 190

Val Val Asp Val Ser His Glu Asp Pro Glu Val Gln Phe Lys Trp Tyr
        195                 200                 205

Val Asp Gly Val Glu Val His Asn Ala Lys Thr Lys Pro Trp Glu Glu
    210                 215                 220

Gln Tyr Asn Ser Thr Phe Arg Val Val Ser Val Leu Thr Val Leu His
225                 230                 235                 240

Gln Asp Trp Leu Asn Gly Lys Glu Tyr Lys Cys Lys Val Ser Asn Lys
                245                 250                 255

Ala Leu Pro Ala Pro Ile Glu Lys Thr Ile Ser Lys Thr Lys Gly Gln
            260                 265                 270

Pro Arg Glu Pro Gln Val Tyr Thr Leu Pro Pro Ser Arg Glu Glu Met
```

|     |     | 275 |     |     |     | 280 |     |     |     | 285 |     |
| --- | --- | --- | --- | --- | --- | --- | --- | --- | --- | --- | --- |

Thr Lys Asn Gln Val Ser Leu Thr Cys Leu Val Lys Gly Phe Tyr Pro
            290                 295                 300

Ser Asp Ile Ala Met Glu Trp Glu Ser Ser Gly Gln Pro Glu Asn Asn
305                 310                 315                 320

Tyr Lys Thr Thr Pro Pro Val Leu Asp Ser Asp Gly Ser Phe Phe Leu
                    325                 330                 335

Tyr Ser Lys Leu Thr Val Asp Lys Ser Arg Trp Gln Gln Gly Asn Ile
            340                 345                 350

Phe Ser Cys Ser Val Met His Glu Ala Leu His Asn His Tyr Thr Gln
            355                 360                 365

Lys Ser Leu Ser Leu Ser Pro
            370                 375

<210> SEQ ID NO 82
<211> LENGTH: 325
<212> TYPE: PRT
<213> ORGANISM: Homo sapiens

<400> SEQUENCE: 82

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
            275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu
            325

<210> SEQ ID NO 83
<211> LENGTH: 227
<212> TYPE: PRT
<213> ORGANISM: Homo sapiens

<400> SEQUENCE: 83

Glu Ser Lys Tyr Gly Pro Pro Cys Pro Ser Cys Pro Ala Pro Glu Phe
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Val His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu
225

<210> SEQ ID NO 84
<211> LENGTH: 227
<212> TYPE: PRT
<213> ORGANISM: Homo sapiens

<400> SEQUENCE: 84

Glu Ser Lys Tyr Gly Pro Pro Cys Pro Ser Cys Pro Ala Pro Glu Phe
1               5                   10                  15

Leu Gly Gly Pro Ser Val Phe Leu Phe Pro Pro Lys Pro Lys Asp Thr
            20                  25                  30

```
Leu Met Ile Ser Arg Thr Pro Glu Val Thr Cys Val Val Asp Val
        35                  40                  45

Ser Gln Glu Asp Pro Glu Val Gln Phe Asn Trp Tyr Val Asp Gly Val
 50                  55                  60

Glu Val His Asn Ala Lys Thr Lys Pro Arg Glu Glu Gln Phe Asn Ser
 65                  70                  75                  80

Thr Tyr Arg Val Val Ser Val Leu Thr Val Leu His Gln Asp Trp Leu
                 85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Lys Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu
225

<210> SEQ ID NO 85
<211> LENGTH: 325
<212> TYPE: PRT
<213> ORGANISM: Homo sapiens

<400> SEQUENCE: 85

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175
```

```
Asn Ser Thr Tyr Arg Val Val Ser Val Leu Thr Val Leu His Gln Asp
            180             185             190

Trp Leu Asn Gly Lys Glu Tyr Lys Cys Lys Val Ser Asn Lys Gly Leu
        195             200             205

Pro Ser Ser Ile Glu Lys Thr Ile Ser Lys Ala Lys Gly Gln Pro Arg
    210             215             220

Glu Pro Gln Val Tyr Thr Leu Pro Pro Ser Gln Glu Glu Met Thr Lys
225             230             235             240

Asn Gln Val Ser Leu Thr Cys Leu Val Lys Gly Phe Tyr Pro Ser Asp
            245             250             255

Ile Ala Val Glu Trp Glu Ser Asn Gly Gln Pro Glu Asn Asn Tyr Lys
            260             265             270

Thr Thr Pro Pro Val Leu Asp Ser Asp Gly Ser Phe Phe Leu Tyr Ser
        275             280             285

Lys Leu Thr Val Asp Lys Ser Arg Trp Gln Gln Gly Asn Val Phe Ser
        290             295             300

Cys Ser Val Met His Glu Ala Leu His Asn His Tyr Thr Gln Lys Ser
305             310             315             320

Leu Ser Leu Ser Leu
                325
```